US007252998B2

(12) United States Patent
Skerra et al.

(10) Patent No.: US 7,252,998 B2
(45) Date of Patent: Aug. 7, 2007

(54) MUTEINS OF HUMAN NEUTROPHIL GELATINASE-ASSOCIATED LIPOCALIN AND RELATED PROTEINS

(75) Inventors: Arne Skerra, Freising (DE); Steffen Schlehuber, Freising (DE)

(73) Assignee: Pieris AG, Freising-Weihenstephan (DE)

( * ) Notice: Subject to any disclaimer, the term of this patent is extended or adjusted under 35 U.S.C. 154(b) by 415 days.

(21) Appl. No.: 10/490,953

(22) PCT Filed: Sep. 18, 2002

(86) PCT No.: PCT/EP02/10490

§ 371 (c)(1),
(2), (4) Date: Sep. 28, 2004

(87) PCT Pub. No.: WO03/029463

PCT Pub. Date: Apr. 10, 2003

(65) Prior Publication Data
US 2006/0088908 A1    Apr. 27, 2006

(30) Foreign Application Priority Data
Sep. 27, 2001  (WO) ...................... PCT/EP01/11213
Apr. 16, 2002  (WO) ...................... PCT/EP02/04223

(51) Int. Cl.
G01N 33/68 (2006.01)
C12N 15/01 (2006.01)
(52) U.S. Cl. ...................... 435/440; 530/350
(58) Field of Classification Search ...................... None
See application file for complete search history.

(56) References Cited

U.S. PATENT DOCUMENTS

| 5,849,576 A | 12/1998 | Skerra et al. |
| 6,099,517 A | 8/2000 | Daugherty |
| 6,103,493 A | 8/2000 | Skerra et al. |
| 6,123,936 A | 9/2000 | Platz et al. |
| 2006/0058510 A1* | 3/2006 | Skerra et al. ............ 530/350 |

FOREIGN PATENT DOCUMENTS

| DE | 44 17 598 A1 | 12/1995 |
| DE | 196 41 876 A1 | 4/1998 |
| DE | 197 42 706 A1 | 4/1999 |
| DE | 199 26 068 C1 | 1/2001 |
| WO | WO 96 23879 A | 8/1996 |
| WO | WO 98/16873 A1 | 4/1998 |
| WO | WO 99 16873 A | 4/1999 |
| WO | WO 99/16873 A1 | 4/1999 |
| WO | WO 00 75308 A | 12/2000 |
| WO | WO 00/75308 A1 | 12/2000 |

OTHER PUBLICATIONS

J.R. Bundgaard et al., "Molecular Cloning and Expression of A cDNA Encode NGAL: A Limpcalin Expressed in Human Neutrophils," *Biochemical and Biophysical Research Communications*, Aug. 15, 1994, pp. 1468-1475, vol. 202, No. 3, XP002036694.
Beck, et al., "Nucleotide Sequence and Genome Organisation of Filamentous Bacteriophages f1 and fd," Gene, vol. 16, pp. 35-58, 1981.
Coles, et al., "The Solution Structure and Dynamics of Human Neutrophil Gelatinase-associated Lipocalin," J. Mol. Biol., vol. 289, pp. 139-157, 1999.
Fitzgerald, Kevin, "In Vitro Display Technologies—New Tools for Drug Discovery," Reviews, vol. 5, No. 6, pp. 253-258, Jun. 2000.
Flower, Darren R., "The Lipocalin Protein Family: Structure and Function," Biochem. J., vol. 318, pp. 1-14, 1996.
Goetz, et al., "Ligand Preference Inferred from the Structure of Neutrophil Gelatinase Associated Lipocalin," Biochemistry, vol. 39, pp. 1935-1941, 2000.
Hengen, Paul N., "Methods and Reagents," Trends Biochem. Sci., vol. 21, pp. 75-76, 1996.
Hoess, Ronald H., "Phage Display of Peptides and Protein Domains," Structural Biology, vol. 3, pp. 572-279, 1993.
Holzfeind, et al., "Structural Organization of the Gene Encoding the Human Lipocalin Tear Prealbumin and Synthesis of the Recombinant Protein in *Escherichia coli*," Gene, vol. 139, pp. 177-183, 1994.
Kjeldsen, et al., "Human Neutrophil Gelatinase-Associated Lipocalin and Homologous Proteins in Rat and Mouse," Biochimica et Biophysica Acta, vol. 1482, pp. 272-283, 2000.
Kraulis, et al., "The Serum Albumin-Binding Domain of Streptococcal Protein G is a Three-Helical Bundle: A Heteronuclear NMR Study," FEBS Letters, vol. 378, pp. 190-194, 1996.
Lohrengel, et al., "Expression and Purification of Woodchuck Tumour Necrosis Factor Alpha," Cytokine, vol. 12, No. 6, pp. 573-577, Jun. 2000.
Low, et al., "Mimicking Somatic Hypermutation: Affinity Maturation of Antibodies Displayed on Bacteriophage Using a Bacterial Mutator Strain," J. Mol. Biol., vol. 260, pp. 359-368, 1996.

(Continued)

Primary Examiner—Robert A Wax
(74) Attorney, Agent, or Firm—Foley & Lardner LLP

(57) ABSTRACT

Disclosed is a method for generating a mutein of a protein selected from the group consisting of human neutrophil gelatinase-associated lipocalin (hNGAL), rat $\alpha_2$-microglobulin-related protein (A2m) and mouse 24p3/uterocalin (24p3), said mutein having detectable affinity to a given target. The method comprises the step of subjecting the protein to mutagenesis at one or more of the sequence positions which correspond to the sequence positions 33 to 54, 66 to 83, 94 to 106, and 123 to 136 of hNGAL, resulting in one or more mutein(s) of the protein. Also disclosed are muteins obtainable by this method.

16 Claims, 12 Drawing Sheets

OTHER PUBLICATIONS

Pervaiz, et al., "Homology and Structure-Function Correlations Between $\alpha_1$-Acid Glycoprotein and Serum Retinol-Binding Protein and Its Relatives," 1987, Department of Biochemistry, University of Miami School of Medicine.

Roberts, Richard W., "Totally In Vitro Protein Selection Using mRNA-Protein Fusions and Ribosome Display," Current Opinion in Chemical Biology, vol. 3, pp. 268-273, 1999.

Schmidt, et al., "Molecular Interaction Between the Strep-Tab Affinity Peptide and Its Cognate Target, Streptavidin," J. Mol. Biol., vol. 255, pp. 753-766, 1996.

Schoepfer, Ralf, "The pRSET Family of T7 Promoter Expression Vectors for Escherichia coli," Gene, vol. 124, pp. 83-85, 1993.

Tulasne, et al., "C-Terminal Peptide of Thrombospondin-1 Includes Platelet Aggregation Through the Fc Receptor γ-Chain-Associated Signaling Pathway and by Agglutination," Blood, vol. 98, No. 12, pp. 3346-3352, Dec. 1, 2001.

Voss, et al., "Mutagenesis of a Flexible Loop in Streptavidin Leads to Higher Affinity for the Strep-Tag II Peptide and Improved Performance in Recombinant Protein Purification," Protein Engineering, vol. 10, No. 8, pp. 975-982, 1997.

Wells, et al., "Rapid Evolution of Peptide and Protein Binding Properties In Vitro," Current Opinion in Structural Biology, vol. 2, pp. 597-604, 1992.

Papiz, et al., "The Structure of Beta-Lactoglobulin and Its Simillarity to Plasma Retinol-Binding Protein," Nature, vol. 324, pp. 383-385, 1986.

Skerra, et al., "Filter Screening of Antibody Fab Fragments Secreted From Individual Bacterial Colonies: Specific Detection of Antigen Binding with a Two-Membrane System," Anal. Biochem., vol. 196, pp. 151-155, 1991.

Yanisch-Perron, et al., "Improved M13 Phage Cloning Vectors and Host Strains: Nucleotide Sequences of the M13mp18 and pUC19 Vector," Gene, vol. 33, pp. 103-119, 1985.

Fling and Gregerson, "Peptide and Protein Molecular Weight Determination by Electrophoresis Using a High-Molarity Tris Buffer System Without Urea," Anal. Biochem., vol. 155, pp. 83-88, 1986.

Wang, et al., "Molecular Cloning of the Complementary DNA for Human Tumor Necrosis Factor," Science, vol. 228, pp. 149-154, 1985.

Beste et al. "Small antibody-like proteins with prescribed ligand specificities derived from the lipocalin fold", Proc. Natl. Acad. Sci. USA, vol. 96, pp. 1898-1903, Mar. 1999.

Chan et al., "The primary structure of rat $\alpha$ 2μ globulin-related protein", Nucleic Acids Research, vol. 16, No. 23, pp. 11368, 1998.

A. Skerra, "Lipocalins as a scaffold", Elsevier Science B.V., Biochimica et Biophysica Acta 1482, pp. 337-350, 2000.

Paine et al., "The Lipocalin website", Elsevier Science B.V., Biochimica et Biophysica Acta 1482, pp. 351-352, 2000.

Schlehuber et al., "A Novel Type of Receptor Protein, Based on the Lipocalin Scaffold, with Specificity for Digoxigenin", J. Mol. Biol. (2000) 297, pp. 1105-1120.

Stoesz et al.< "Overexpression of neu-related lipocalin (NRL) in neu-initiated but not ras or chemically initiated rat mammary carcinomas", Oncogene (1995), 11, pp. 2233-2241.

* cited by examiner

1. PCR

2. PCR

SEQUENCE LISTING

```
<160> NUMBER OF SEQ ID NOS: 39

<210> SEQ ID NO 1
<211> LENGTH: 71
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, g or t
<220> FEATURE:
<221> NAME/KEY: modified_base
<222> LOCATION: (26)..(27)
<223> OTHER INFORMATION: a, c, g or t
<220> FEATURE:
<221> NAME/KEY: modified_base
<222> LOCATION: (32)..(33)
<223> OTHER INFORMATION: a, c, g or t
<220> FEATURE:
<221> NAME/KEY: modified_base
<222> LOCATION: (38)..(39)
<223> OTHER INFORMATION: a, c, g or t
<220> FEATURE:
<221> NAME/KEY: modified_base
<222> LOCATION: (41)..(42)
<223> OTHER INFORMATION: a, c, g or t
<220> FEATURE:
<221> NAME/KEY: modified_base
<222> LOCATION: (47)..(48)
<223> OTHER INFORMATION: a, c, g or t
<220> FEATURE:
<221> NAME/KEY: modified_base
<222> LOCATION: (50)..(51)
<223> OTHER INFORMATION: a, c, g or t

<400> SEQUENCE: 1
ggtaggtctc gcagggaatn nkattnnkag annkgacnnk nnkccgnnkn nkatgtatgc    60
caccatctat g                                                        71
```

<210> SEQ ID NO 2
<211> LENGTH: 77
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (31)..(32)
<223> OTHER INFORMATION: a, c, g or t
<220> FEATURE:
<221> NAME/KEY: modified_base
<222> LOCATION: (37)..(38)
<223> OTHER INFORMATION: a, c, g or t
<220> FEATURE:
<221> NAME/KEY: modified_base
<222> LOCATION: (49)..(50)
<223> OTHER INFORMATION: a, c, g or t
<220> FEATURE:
<221> NAME/KEY: modified_base
<222> LOCATION: (52)..(53)
<223> OTHER INFORMATION: a, c, g or t
<220> FEATURE:
<221> NAME/KEY: modified_base
<222> LOCATION: (58)..(59)
<223> OTHER INFORMATION: a, c, g or t

<400> SEQUENCE: 2
ggctgggaac ctggaacaaa agtcctgatm nngtamnnac acttcttmnn mnnaaamnng    60
acggaggtga cattgta                                                  77

<210> SEQ ID NO 3
<211> LENGTH: 79
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (53)..(54)
<223> OTHER INFORMATION: a, c, g or t
<220> FEATURE:
<221> NAME/KEY: modified_base
<222> LOCATION: (56)..(57)
<223> OTHER INFORMATION: a, c, g or t
<220> FEATURE:
<221> NAME/KEY: modified_base
<222> LOCATION: (59)..(60)
<223> OTHER INFORMATION: a, c, g or t

<400> SEQUENCE: 3
tgttccaggt tcccagccag gcgagttcac gctgggcaac attaagagtt acnnknnkkn    60
kacgagttac ctcgtccga                                                79

<210> SEQ ID NO 4
<211> LENGTH: 77
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (33)..(34)
<223> OTHER INFORMATION: a, c, g or t
<220> FEATURE:
<221> NAME/KEY: modified_base
<222> LOCATION: (39)..(40)
<223> OTHER INFORMATION: a, c, g or t
<220> FEATURE:
<221> NAME/KEY: modified_base
<222> LOCATION: (45)..(46)
<223> OTHER INFORMATION: a, c, g or t
<220> FEATURE:
<221> NAME/KEY: modified_base
<222> LOCATION: (48)..(49)
<223> OTHER INFORMATION: a, c, g or t
<220> FEATURE:
<221> NAME/KEY: modified_base
<222> LOCATION: (54)..(55)
<223> OTHER INFORMATION: a, c, g or t

<400> SEQUENCE: 4
ccttggttct cccgtagatg gtaatcttga amnnctcmnn gttmnnmnna acmnncttaa        60
agaacaccat agcatgc                                                      77

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttccaggac aaccaattcc atgggaagtg gtatgtggta ggtctcgcag ggaa             54

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cctttagttc cgaagccagc tccttggttc tcccgtaga                              39

<210> SEQ ID NO 7
<211> LENGTH: 1231
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(84)
<220> FEATURE:
<221> NAME/KEY: sig_peptide
<222> LOCATION: (22)..(84)
<220> FEATURE:
<221> NAME/KEY: CDS
<222> LOCATION: (85)..(618)
<223> OTHER INFORMATION: mature hNGAL
<220> FEATURE:
<221> NAME/KEY: mat_peptide
<222> LOCATION: (85)..(1221)
<223> OTHER INFORMATION: fusion protein of modified hNGAL, Strep-tag II
      and fragment of phage coat protein pIII
<220> FEATURE:
<221> NAME/KEY: CDS
<222> LOCATION: (619)..(648)
<223> OTHER INFORMATION: Strep-tag II affinity tag
<220> FEATURE:
<221> NAME/KEY: CDS
<222> LOCATION: (649)..(651)
<223> OTHER INFORMATION: amber stop codon
<220> FEATURE:
<221> NAME/KEY: CDS
<222> LOCATION: (652)..(1221)
<223> OTHER INFORMATION: codes for amino acids 217-406 of coat protein -continued pIII

<400> SEQUENCE: 7

```
tctagataac gagggcaaaa a atg aaa aag aca gct atc gcg att gca gtg      51
                         Met Lys Lys Thr Ala Ile Ala Ile Ala Val
                          -20             -15 gca ctg gct ggt ttc gct acc gta gcg cag gcc cag gac tcc acc tca      99
Ala Leu Ala Gly Phe Ala Thr Val Ala Gln Ala Gln Asp Ser Thr Ser
    -10              -5              -1   1               5 gac ctg atc cca gcc cca cct ctg agc aag gtc cct ctg cag cag aac     147
Asp Leu Ile Pro Ala Pro Pro Leu Ser Lys Val Pro Leu Gln Gln Asn
                10              15              20 ttc cag gac aac caa ttc cat ggg aag tgg tat ctg gta ggt ctc gca     195
Phe Gln Asp Asn Gln Phe His Gly Lys Trp Tyr Leu Val Gly Leu Ala
            25              30              35 ggg aat gca att ctc aga gaa gac aaa gac ccg caa aag atg tat gcc     243
Gly Asn Ala Ile Leu Arg Glu Asp Lys Asp Pro Gln Lys Met Tyr Ala
        40              45              50 acc atc tat gag ctg aaa gaa gac aag agc tac aat gtc acc tcc gtc     291
Thr Ile Tyr Glu Leu Lys Glu Asp Lys Ser Tyr Asn Val Thr Ser Val
    55              60              65 ctg ttt agg aaa aag aag tgt gac tac tgg atc agg act ttt gtt cca     339
Leu Phe Arg Lys Lys Lys Cys Asp Tyr Trp Ile Arg Thr Phe Val Pro
70              75              80              85 ggt tgc cag ccc ggc gag ttc acg ctg ggc aac att aag agt tac cct     387
Gly Cys Gln Pro Gly Glu Phe Thr Leu Gly Asn Ile Lys Ser Tyr Pro
            90              95             100 gga tta acg agt tac ctc gtc cga gtg gtg agc acc aac tac aac cag     435
Gly Leu Thr Ser Tyr Leu Val Arg Val Val Ser Thr Asn Tyr Asn Gln
        105             110             115 cat gct atg gtg ttc ttt aag aaa gtt tct caa aac agg gag tac ttc     483
His Ala Met Val Phe Phe Lys Lys Val Ser Gln Asn Arg Glu Tyr Phe
    120             125             130 aag att acc atc tac ggg aga acc aag gag ctg gct tcg gaa cta aag     531
Lys Ile Thr Ile Tyr Gly Arg Thr Lys Glu Leu Ala Ser Glu Leu Lys
135             140             145 gag aac ttc atc cgc ttc tct aaa tct ctg ggc ctc cct gaa aac cac     579
Glu Asn Phe Ile Arg Phe Ser Lys Ser Leu Gly Leu Pro Glu Asn His
150             155             160             165 atc gtc ttc cct gtc cca atc gac cag tgt atc gac ggc agc gct tgg     627
Ile Val Phe Pro Val Pro Ile Asp Gln Cys Ile Asp Gly Ser Ala Trp
            170             175             180 tcc cac ccg cag ttc gaa aaa tag gct ggc ggc ggc tct ggt ggt ggt     675
Ser His Pro Gln Phe Glu Lys Gln Ala Gly Gly Gly Ser Gly Gly Gly
        185             190             195 tct ggc ggc ggc tct gag ggt ggt ggc tct gag ggt ggc ggt tct gag     723
Ser Gly Gly Gly Ser Glu Gly Gly Gly Ser Glu Gly Gly Gly Ser Glu
    200             205             210 ggt ggc ggc tct gag gga ggc ggt tcc ggt ggt ggc tct ggt tcc ggt     771
Gly Gly Gly Ser Glu Gly Gly Gly Ser Gly Gly Gly Ser Gly Ser Gly
215             220             225 gat ttt gat tat gaa aag atg gca aac gct aat aag ggg gct atg acc     819
Asp Phe Asp Tyr Glu Lys Met Ala Asn Ala Asn Lys Gly Ala Met Thr
230             235             240             245 gaa aat gcc gat gaa aac gcg cta cag tct gac gct aaa ggc aaa ctt     867
Glu Asn Ala Asp Glu Asn Ala Leu Gln Ser Asp Ala Lys Gly Lys Leu
            250             255             260 gat tct gtc gct act gat tac ggt gct gct atc gat ggt ttc att ggt     915
Asp Ser Val Ala Thr Asp Tyr Gly Ala Ala Ile Asp Gly Phe Ile Gly
        265             270             275
```

-continued

```
gac gtt tcc ggc ctt gct aat ggt aat ggt gct act ggt gat ttt gct      963
Asp Val Ser Gly Leu Ala Asn Gly Asn Gly Ala Thr Gly Asp Phe Ala
            280                 285                 290 ggc tct aat tcc caa atg gct caa gtc ggt gac ggt gat aat tca cct     1011
Gly Ser Asn Ser Gln Met Ala Gln Val Gly Asp Gly Asp Asn Ser Pro
        295                 300                 305 tta atg aat aat ttc cgt caa tat tta cct tcc ctc cct caa tcg gtt     1059
Leu Met Asn Asn Phe Arg Gln Tyr Leu Pro Ser Leu Pro Gln Ser Val
310                 315                 320                 325 gaa tgt cgc cct ttt gtc ttt ggc gct ggt aaa cca tat gaa ttt tct     1107
Glu Cys Arg Pro Phe Val Phe Gly Ala Gly Lys Pro Tyr Glu Phe Ser
                330                 335                 340 att gat tgt gac aaa ata aac tta ttc cgt ggt gtc ttt gcg ttt ctt     1155
Ile Asp Cys Asp Lys Ile Asn Leu Phe Arg Gly Val Phe Ala Phe Leu
                345                 350                 355 tta tat gtt gcc acc ttt atg tat gta ttt tct acg ttt gct aac ata     1203
Leu Tyr Val Ala Thr Phe Met Tyr Val Phe Ser Thr Phe Ala Asn Ile
        360                 365                 370 ctg cgt aat aag gag tct taataagctt                                  1231
Leu Arg Asn Lys Glu Ser
    375
```

<210> SEQ ID NO 8
<211> LENGTH: 1231
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(84)
<220> FEATURE:
<221> NAME/KEY: sig_peptide
<222> LOCATION: (22)..(84)
<220> FEATURE:
<221> NAME/KEY: CDS
<222> LOCATION: (85)..(618)
<223> OTHER INFORMATION: mature hNGAL
<220> FEATURE:
<221> NAME/KEY: mat_peptide
<222> LOCATION: (85)..(1221)
<223> OTHER INFORMATION: fusion protein of hNGAL, Strep-tag II and
      fragment of phage coat protein pIII
<220> FEATURE:
<221> NAME/KEY: CDS
<222> LOCATION: (619)..(648)
<223> OTHER INFORMATION: Strep-tag II affinity tag
<220> FEATURE:
<221> NAME/KEY: CDS
<222> LOCATION: (649)..(651)
<223> OTHER INFORMATION: amber stop codon
<220> FEATURE:
<221> NAME/KEY: CDS
<222> LOCATION: (652)..(1221)
<223> OTHER INFORMATION: codes for amino acids 217-406 of coat protein
      pIII

<400> SEQUENCE: 8

```
tctagataac gagggcaaaa a atg aaa aag aca gct atc gcg att gca gtg       51
                        Met Lys Lys Thr Ala Ile Ala Ile Ala Val
                            -20                 -15 gca ctg gct ggt ttc gct acc gta gcg cag gcc cag gac tcc acc tca       99
Ala Leu Ala Gly Phe Ala Thr Val Ala Gln Ala Gln Asp Ser Thr Ser
    -10                 -5              -1   1                   5 gac ctg atc cca gcc cca cct ctg agc aag gtc cct ctg cag cag aac      147
Asp Leu Ile Pro Ala Pro Pro Leu Ser Lys Val Pro Leu Gln Gln Asn
            10                  15                  20
```

| | |
|---|---|
| ttc cag gac aac caa ttc cag ggg aag tgg tat ctg gta ggt ctc gca<br>Phe Gln Asp Asn Gln Phe Gln Gly Lys Trp Tyr Leu Val Gly Leu Ala<br>25                          30                      35 | 195 |
| ggg aat gca att ctc aga gaa gac aaa gac ccg caa aag atg tat gcc<br>Gly Asn Ala Ile Leu Arg Glu Asp Lys Asp Pro Gln Lys Met Tyr Ala<br>      40                       45                     50 | 243 |
| acc atc tat gag ctg aaa gaa gac aag agc tac aat gtc acc tcc gtc<br>Thr Ile Tyr Glu Leu Lys Glu Asp Lys Ser Tyr Asn Val Thr Ser Val<br>55                          60                      65 | 291 |
| ctg ttt agg aaa aag aag tgt gac tac tgg atc agg act ttt gtt cca<br>Leu Phe Arg Lys Lys Lys Cys Asp Tyr Trp Ile Arg Thr Phe Val Pro<br>70                        75                     80                     85 | 339 |
| ggt tgc cag ccc ggc gag ttc acg ctg ggc aac att aag agt tac cct<br>Gly Cys Gln Pro Gly Glu Phe Thr Leu Gly Asn Ile Lys Ser Tyr Pro<br>                    90                     95                    100 | 387 |
| gga tta acg agt tac ctc gtc cga gtg gtg agc acc aac tac aac cag<br>Gly Leu Thr Ser Tyr Leu Val Arg Val Val Ser Thr Asn Tyr Asn Gln<br>                105                   110                  115 | 435 |
| cat gct atg gtg ttc ttt aag aaa gtt tct caa aac agg gag tac ttc<br>His Ala Met Val Phe Phe Lys Lys Val Ser Gln Asn Arg Glu Tyr Phe<br>         120                   125                  130 | 483 |
| aag att acc atc tac ggg aga acc aag gag ctg cct tcg gaa cta aag<br>Lys Ile Thr Ile Tyr Gly Arg Thr Lys Glu Leu Pro Ser Glu Leu Lys<br>135                        140                   145 | 531 |
| gag aac ttc atc cgc ttc tcc aaa tct ctg ggc ctc cct gaa aac cac<br>Glu Asn Phe Ile Arg Phe Ser Lys Ser Leu Gly Leu Pro Glu Asn His<br>150                        155                   160                 165 | 579 |
| atc gtc ttc cct gtc cca atc gac cag tgt atc gac ggc agc gct tgg<br>Ile Val Phe Pro Val Pro Ile Asp Gln Cys Ile Asp Gly Ser Ala Trp<br>                  170                   175                  180 | 627 |
| tcc cac ccg cag ttc gaa aaa tag gct ggc ggc ggc tct ggt ggt ggt<br>Ser His Pro Gln Phe Glu Lys Gln Ala Gly Gly Gly Ser Gly Gly Gly<br>                185                   190                  195 | 675 |
| tct ggc ggc ggc tct gag ggt ggt ggc tct gag ggt ggc ggt tct gag<br>Ser Gly Gly Gly Ser Glu Gly Gly Gly Ser Glu Gly Gly Gly Ser Glu<br>         200                   205                  210 | 723 |
| ggt ggc ggc tct gag gga ggc ggt tcc ggt ggt ggc tct ggt tcc ggt<br>Gly Gly Gly Ser Glu Gly Gly Gly Ser Gly Gly Gly Ser Gly Ser Gly<br>         215                   220                  225 | 771 |
| gat ttt gat tat gaa aag atg gca aac gct aat aag ggg gct atg acc<br>Asp Phe Asp Tyr Glu Lys Met Ala Asn Ala Asn Lys Gly Ala Met Thr<br>230                        235                   240                 245 | 819 |
| gaa aat gcc gat gaa aac gcg cta cag tct gac gct aaa ggc aaa ctt<br>Glu Asn Ala Asp Glu Asn Ala Leu Gln Ser Asp Ala Lys Gly Lys Leu<br>                250                   255                  260 | 867 |
| gat tct gtc gct act gat tac ggt gct gct atc gat ggt ttc att ggt<br>Asp Ser Val Ala Thr Asp Tyr Gly Ala Ala Ile Asp Gly Phe Ile Gly<br>         265                   270                  275 | 915 |
| gac gtt tcc ggc ctt gct aat ggt aat ggt gct act ggt gat ttt gct<br>Asp Val Ser Gly Leu Ala Asn Gly Asn Gly Ala Thr Gly Asp Phe Ala<br>         280                   285                  290 | 963 |
| ggc tct aat tcc caa atg gct caa gtc ggt gac ggt gat aat tca cct<br>Gly Ser Asn Ser Gln Met Ala Gln Val Gly Asp Gly Asp Asn Ser Pro<br>295                        300                   305 | 1011 |
| tta atg aat aat ttc cgt caa tat tta cct tcc ctc cct caa tcg gtt<br>Leu Met Asn Asn Phe Arg Gln Tyr Leu Pro Ser Leu Pro Gln Ser Val<br>310                        315                   320                 325 | 1059 |
| gaa tgt cgc cct ttt gtc ttt ggc gct ggt aaa cca tat gaa ttt tct<br>Glu Cys Arg Pro Phe Val Phe Gly Ala Gly Lys Pro Tyr Glu Phe Ser | 1107 |

-continued

```
                       330                 335                 340
att gat tgt gac aaa ata aac tta ttc cgt ggt gtc ttt gcg ttt ctt      1155
Ile Asp Cys Asp Lys Ile Asn Leu Phe Arg Gly Val Phe Ala Phe Leu
            345                 350                 355 tta tat gtt gcc acc ttt atg tat gta ttt tct acg ttt gct aac ata      1203
Leu Tyr Val Ala Thr Phe Met Tyr Val Phe Ser Thr Phe Ala Asn Ile
        360                 365                 370 ctg cgt aat aag gag tct taataagctt                                   1231
Leu Arg Asn Lys Glu Ser
    375
```

<210> SEQ ID NO 9
<211> LENGTH: 805
<212> TYPE: DNA
<213> ORGANISM: Artificial Sequence
<220> FEATURE:
<223> OTHER INFORMATION: Description of Artificial Sequence: Synthetic nucleotide sequence
<220> FEATURE:
<221> NAME/KEY: CDS
<222> LOCATION: (22)..(84)
<220> FEATURE:
<221> NAME/KEY: sig_peptide
<222> LOCATION: (22)..(84)
<220> FEATURE:
<221> NAME/KEY: CDS
<222> LOCATION: (85)..(618)
<223> OTHER INFORMATION: mature hNGAL
<220> FEATURE:
<221> NAME/KEY: mat_peptide
<222> LOCATION: (85)..(795)
<223> OTHER INFORMATION: fusion protein of modified hNGAL, Strep-tag II and albumin binding domain
<220> FEATURE:
<221> NAME/KEY: CDS
<222> LOCATION: (619)..(648)
<223> OTHER INFORMATION: Strep-tag II affinity tag
<220> FEATURE:
<221> NAME/KEY: CDS
<222> LOCATION: (649)..(795)
<223> OTHER INFORMATION: albumin binding domain of Protein G

<400> SEQUENCE: 9

```
tctagataac gagggcaaaa a atg aaa aag aca gct atc gcg att gca gtg       51
                        Met Lys Lys Thr Ala Ile Ala Ile Ala Val
                            -20                 -15 gca ctg gct ggt ttc gct acc gta gcg cag gcc cag gac tcc acc tca       99
Ala Leu Ala Gly Phe Ala Thr Val Ala Gln Ala Gln Asp Ser Thr Ser
    -10                 -5              -1   1               5 gac ctg atc cca gcc cca cct ctg agc aag gtc cct ctg cag cag aac      147
Asp Leu Ile Pro Ala Pro Pro Leu Ser Lys Val Pro Leu Gln Gln Asn
                10                  15                  20 ttc cag gac aac caa ttc cag ggg aag tgg tat ctg gta ggt ctc gca      195
Phe Gln Asp Asn Gln Phe Gln Gly Lys Trp Tyr Leu Val Gly Leu Ala
            25                  30                  35 ggg aat gca att ctc aga gaa gac aaa gac ccg caa aag atg tat gcc      243
Gly Asn Ala Ile Leu Arg Glu Asp Lys Asp Pro Gln Lys Met Tyr Ala
        40                  45                  50 acc atc tat gag ctg aaa gaa gac aag agc tac aat gtc acc tcc gtc      291
Thr Ile Tyr Glu Leu Lys Glu Asp Lys Ser Tyr Asn Val Thr Ser Val
    55                  60                  65 ctg ttt agg aaa aag aag tgt gac tac tgg atc agg act ttt gtt cca      339
Leu Phe Arg Lys Lys Lys Cys Asp Tyr Trp Ile Arg Thr Phe Val Pro
70                  75                  80                  85 ggt tgc cag ccc ggc gag ttc acg ctg ggc aac att aag agt tac cct      387
Gly Cys Gln Pro Gly Glu Phe Thr Leu Gly Asn Ile Lys Ser Tyr Pro
                90                  95                 100
```

-continued

```
gga tta acg agt tac ctc gtc cga gtg gtg agc acc aac tac aac cag      435
Gly Leu Thr Ser Tyr Leu Val Arg Val Val Ser Thr Asn Tyr Asn Gln
            105                 110                 115 cat gct atg gtg ttc ttt aag aaa gtt tct caa aac agg gag tac ttc      483
His Ala Met Val Phe Phe Lys Lys Val Ser Gln Asn Arg Glu Tyr Phe
        120                 125                 130 aag att acc atc tac ggg aga acc aag gag ctg cct tcg gaa cta aag      531
Lys Ile Thr Ile Tyr Gly Arg Thr Lys Glu Leu Pro Ser Glu Leu Lys
    135                 140                 145 gag aac ttc atc cgc ttc tcc aaa tct ctg ggc ctc cct gaa aac cac      579
Glu Asn Phe Ile Arg Phe Ser Lys Ser Leu Gly Leu Pro Glu Asn His
150                 155                 160                 165 atc gtc ttc cct gtc cca atc gac cag tgt atc gac ggc agc gct tgg      627
Ile Val Phe Pro Val Pro Ile Asp Gln Cys Ile Asp Gly Ser Ala Trp
                170                 175                 180 tcc cac ccg cag ttc gaa aaa cca gct agc ctg gct gaa gct aaa gtt      675
Ser His Pro Gln Phe Glu Lys Pro Ala Ser Leu Ala Glu Ala Lys Val
            185                 190                 195 ctg gct aac cgt gaa ctg gac aaa tac ggt gtt tcc gac tac tac aaa      723
Leu Ala Asn Arg Glu Leu Asp Lys Tyr Gly Val Ser Asp Tyr Tyr Lys
        200                 205                 210 aac ctc atc aac aac gct aaa acc gtt gaa ggt gtt aaa gct ctg atc      771
Asn Leu Ile Asn Asn Ala Lys Thr Val Glu Gly Val Lys Ala Leu Ile
    215                 220                 225 gac gaa att ctc gca gca ctg ccg taataagctt                           805
Asp Glu Ile Leu Ala Ala Leu Pro
230                 235

<210> SEQ ID NO 10
<211> LENGTH: 580
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(84)
<220> FEATURE:
<221> NAME/KEY: sig_peptide
<222> LOCATION: (22)..(84)
<220> FEATURE:
<221> NAME/KEY: CDS
<222> LOCATION: (85)..(543)
<223> OTHER INFORMATION: mature human tear Lipocalin
<220> FEATURE:
<221> NAME/KEY: mat_peptide
<222> LOCATION: (85)..(570)
<223> OTHER INFORMATION: fusion protein of modified human tear Lipocalin
      and Strep-tag II
<220> FEATURE:
<221> NAME/KEY: CDS
<222> LOCATION: (544)..(570)
<223> OTHER INFORMATION: Strep-tag II affinity tag

<400> SEQUENCE: 10
tctagataac gagggcaaaa a atg aaa aag aca gct atc gcg att gca gtg      51
                        Met Lys Lys Thr Ala Ile Ala Ile Ala Val
                            -20                 -15 gca ctg gct ggt ttc gct acc gta gcg cag gcc gcc tca gac gag gag      99
Ala Leu Ala Gly Phe Ala Thr Val Ala Gln Ala Ala Ser Asp Glu Glu
        -10                 -5          -1  1               5 att cag gat gtg tca ggg acg tgg tat ctg aag gcc atg acg gtg gac     147
Ile Gln Asp Val Ser Gly Thr Trp Tyr Leu Lys Ala Met Thr Val Asp
            10                  15                  20
```

-continued

```
agg gag ttc cct gag atg aat ctg gaa tcg gtg aca ccc atg acc ctc        195
Arg Glu Phe Pro Glu Met Asn Leu Glu Ser Val Thr Pro Met Thr Leu
             25                  30                  35 acg acc ctg gaa ggg ggc aac ctg gaa gcc aag gtc acc atg ctg ata        243
Thr Thr Leu Glu Gly Gly Asn Leu Glu Ala Lys Val Thr Met Leu Ile
         40                  45                  50 agt ggc cgg tgc cag gag gtg aag gcc gtc ctg gag aaa act gac gag        291
Ser Gly Arg Cys Gln Glu Val Lys Ala Val Leu Glu Lys Thr Asp Glu
     55                  60                  65 ccg gga aaa tac acg gcc gac ggg ggc aag cac gtg gca tac atc atc        339
Pro Gly Lys Tyr Thr Ala Asp Gly Gly Lys His Val Ala Tyr Ile Ile
 70                  75                  80                  85 agg tcg cac gtg aag gac cac tac atc ttt tac tct gag ggc gag ctc        387
Arg Ser His Val Lys Asp His Tyr Ile Phe Tyr Ser Glu Gly Glu Leu
                 90                  95                 100 cac ggg aag ccg gtc cga cgg gtg aag ctc gtg ggc aga gac ccc aag        435
His Gly Lys Pro Val Arg Arg Val Lys Leu Val Gly Arg Asp Pro Lys
            105                 110                 115 aac aac ctg gaa gcc ttg gag gac ttt gag aaa gcc gca gga gcc cgc        483
Asn Asn Leu Glu Ala Leu Glu Asp Phe Glu Lys Ala Ala Gly Ala Arg
        120                 125                 130 gga ctc agc acg gag agc atc ctc atc ccc agg cag agc gaa acc tgc        531
Gly Leu Ser Thr Glu Ser Ile Leu Ile Pro Arg Gln Ser Glu Thr Cys
    135                 140                 145 tct cca ggg agc gct tgg tct cac ccg cag ttc gaa aaa taataagctt        580
Ser Pro Gly Ser Ala Trp Ser His Pro Gln Phe Glu Lys
150                 155                 160
```

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 11 ccactccta tcagtgat                                                     18

<210> SEQ ID NO 12
<211> LENGTH: 537
<212> TYPE: DNA
<213> ORGANISM: Artificial Sequence
<220> FEATURE:
<223> OTHER INFORMATION: Description of Artificial Sequence: Synthetic nucleotide sequence
<220> FEATURE:
<221> NAME/KEY: CDS
<222> LOCATION: (1)..(537)
<223> OTHER INFORMATION: Mutein Tipca

<400> SEQUENCE: 12

```
cag gac tcc acc tca gac ctg atc cca gcc cca cct ctg agc aag gtc         48
Gln Asp Ser Thr Ser Asp Leu Ile Pro Ala Pro Pro Leu Ser Lys Val
  1               5                  10                  15 cct ctg cag cag aac ttc cag gac aac caa ttc cat ggg aag tgg tat         96
Pro Leu Gln Gln Asn Phe Gln Asp Asn Gln Phe His Gly Lys Trp Tyr
             20                  25                  30 gtg gta ggt ctc gca ggg aat tgt att gtg aga cag gac ctt ctg ccg        144
Val Val Gly Leu Ala Gly Asn Cys Ile Val Arg Gln Asp Leu Leu Pro
         35                  40                  45 tct atg atg tat gcc acc atc tat gag ctg aaa gaa gac aag agc tac        192
Ser Met Met Tyr Ala Thr Ile Tyr Glu Leu Lys Glu Asp Lys Ser Tyr
     50                  55                  60
```

-continued

```
aat gtc acc tcc gtc tta ttt atg gat aag aag tgt cgg tac tat atc      240
Asn Val Thr Ser Val Leu Phe Met Asp Lys Lys Cys Arg Tyr Tyr Ile
 65              70                  75                  80 agg act ttt gtt cca ggt tcc cag ccg ggc gag ttc acg ctg ggc aac      288
Arg Thr Phe Val Pro Gly Ser Gln Pro Gly Glu Phe Thr Leu Gly Asn
                 85                  90                  95 att aag agt tac ggt att gtt acg agt tac ctc gtc cga gtg gtg agc      336
Ile Lys Ser Tyr Gly Ile Val Thr Ser Tyr Leu Val Arg Val Val Ser
            100                 105                 110 acc aac tac aac cag cat gct atg gtg ttc ttt aag tcg gtt atg acg      384
Thr Asn Tyr Asn Gln His Ala Met Val Phe Phe Lys Ser Val Met Thr
        115                 120                 125 aac tag gag gcg ttc aag att acc atc tac ggg aga acc aag gag ctg      432
Asn Gln Glu Ala Phe Lys Ile Thr Ile Tyr Gly Arg Thr Lys Glu Leu
    130                 135                 140 gct tcg gaa cta aag gag aac ttc atc cgc ttc tct aaa tct ctg ggc      480
Ala Ser Glu Leu Lys Glu Asn Phe Ile Arg Phe Ser Lys Ser Leu Gly
145                 150                 155                 160 ctc cct gaa aac cac atc gtc ttc cct gtc cca atc gac cag tgt atc      528
Leu Pro Glu Asn His Ile Val Phe Pro Val Pro Ile Asp Gln Cys Ile
                165                 170                 175 gac ggc agc                                                          537
Asp Gly Ser
```

<210> SEQ ID NO 13
<211> LENGTH: 400
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: SIGNAL
<222> LOCATION: (-21)..(-1)
<220> FEATURE:
<221> NAME/KEY: CHAIN
<222> LOCATION: (1)..(379)
<223> OTHER INFORMATION: fusion protein of modified hNGAL, Strep-tag II
      and fragment of phage coat protein pIII
<220> FEATURE:
<221> NAME/KEY: MISC_FEATURE
<222> LOCATION: (1)..(178)
<223> OTHER INFORMATION: mature hNGAL
<220> FEATURE:
<221> NAME/KEY: MISC_FEATURE
<222> LOCATION: (179)..(188)
<223> OTHER INFORMATION: Strep-tag II affinity tag
<220> FEATURE:
<221> NAME/KEY: MISC_FEATURE
<222> LOCATION: (189)
<223> OTHER INFORMATION: amber stop codon
<220> FEATURE:
<221> NAME/KEY: MISC_FEATURE
<222> LOCATION: (190)..(379)
<223> OTHER INFORMATION: amino acids 217-406 of coat protein pIII

<400> SEQUENCE: 13

```
Met Lys Lys Thr Ala Ile Ala Ile Ala Val Ala Leu Ala Gly Phe Ala
    -20                 -15                 -10

Thr Val Ala Gln Ala Gln Asp Ser Thr Ser Asp Leu Ile Pro Ala Pro
 -5              -1   1               5                  10

Pro Leu Ser Lys Val Pro Leu Gln Gln Asn Phe Gln Asp Asn Gln Phe
                15                  20                  25

His Gly Lys Trp Tyr Leu Val Gly Leu Ala Gly Asn Ala Ile Leu Arg
            30                  35                  40
```

```
Glu Asp Lys Asp Pro Gln Lys Met Tyr Ala Thr Ile Tyr Glu Leu Lys
    45                  50                  55

Glu Asp Lys Ser Tyr Asn Val Thr Ser Val Leu Phe Arg Lys Lys Lys
60                  65                  70                  75

Cys Asp Tyr Trp Ile Arg Thr Phe Val Pro Gly Cys Gln Pro Gly Glu
                80                  85                  90

Phe Thr Leu Gly Asn Ile Lys Ser Tyr Pro Gly Leu Thr Ser Tyr Leu
            95                  100                 105

Val Arg Val Val Ser Thr Asn Tyr Asn Gln His Ala Met Val Phe Phe
            110                 115                 120

Lys Lys Val Ser Gln Asn Arg Glu Tyr Phe Lys Ile Thr Ile Tyr Gly
    125                 130                 135

Arg Thr Lys Glu Leu Ala Ser Glu Leu Lys Glu Asn Phe Ile Arg Phe
140                 145                 150                 155

Ser Lys Ser Leu Gly Leu Pro Glu Asn His Ile Val Phe Pro Val Pro
                160                 165                 170

Ile Asp Gln Cys Ile Asp Gly Ser Ala Trp Ser His Pro Gln Phe Glu
            175                 180                 185

Lys Gln Ala Gly Gly Gly Ser Gly Gly Ser Gly Gly Gly Ser Glu
    190                 195                 200

Gly Gly Gly Ser Glu Gly Gly Ser Glu Gly Gly Ser Glu Gly
    205                 210                 215

Gly Gly Ser Gly Gly Ser Gly Ser Gly Asp Phe Asp Tyr Glu Lys
220                 225                 230                 235

Met Ala Asn Ala Asn Lys Gly Ala Met Thr Glu Asn Ala Asp Glu Asn
                240                 245                 250

Ala Leu Gln Ser Asp Ala Lys Gly Lys Leu Asp Ser Val Ala Thr Asp
            255                 260                 265

Tyr Gly Ala Ala Ile Asp Gly Phe Ile Gly Asp Val Ser Gly Leu Ala
        270                 275                 280

Asn Gly Asn Gly Ala Thr Gly Asp Phe Ala Gly Ser Asn Ser Gln Met
        285                 290                 295

Ala Gln Val Gly Asp Gly Asp Asn Ser Pro Leu Met Asn Asn Phe Arg
300                 305                 310                 315

Gln Tyr Leu Pro Ser Leu Pro Gln Ser Val Glu Cys Arg Pro Phe Val
            320                 325                 330

Phe Gly Ala Gly Lys Pro Tyr Glu Phe Ser Ile Asp Cys Asp Lys Ile
        335                 340                 345

Asn Leu Phe Arg Gly Val Phe Ala Phe Leu Leu Tyr Val Ala Thr Phe
    350                 355                 360

Met Tyr Val Phe Ser Thr Phe Ala Asn Ile Leu Arg Asn Lys Glu Ser
    365                 370                 375
```

<210> SEQ ID NO 14
<211> LENGTH: 400
<212> TYPE: PRT
<213> ORGANISM: Artificial Sequence
<220> FEATURE:
<223> OTHER INFORMATION: Description of Artificial Sequence: Synthetic amino acid sequence
<220> FEATURE:
<221> NAME/KEY: SIGNAL
<222> LOCATION: (-21)..(-1)
<220> FEATURE:
<221> NAME/KEY: CHAIN
<222> LOCATION: (1)..(379)
<223> OTHER INFORMATION: fusion protein of hNGAL, Strep-tag II and fragment of phage coat protein pIII

```
<220> FEATURE:
<221> NAME/KEY: MISC_FEATURE
<222> LOCATION: (1)..(178)
<223> OTHER INFORMATION: mature hNGAL
<220> FEATURE:
<221> NAME/KEY: MISC_FEATURE
<222> LOCATION: (179)..(188)
<223> OTHER INFORMATION: Strep-tag II affinity tag
<220> FEATURE:
<221> NAME/KEY: MISC_FEATURE
<222> LOCATION: (189)
<223> OTHER INFORMATION: amber stop codon
<220> FEATURE:
<221> NAME/KEY: MISC_FEATURE
<222> LOCATION: (190)..(379)
<223> OTHER INFORMATION: amino acids 217-406 of coat protein pIII

<400> SEQUENCE: 14

Met Lys Lys Thr Ala Ile Ala Ile Ala Val Ala Leu Ala Gly Phe Ala
    -20             -15                 -10

Thr Val Ala Gln Ala Gln Asp Ser Thr Ser Asp Leu Ile Pro Ala Pro
 -5          -1   1              5                  10

Pro Leu Ser Lys Val Pro Leu Gln Gln Asn Phe Gln Asp Asn Gln Phe
            15              20                  25

Gln Gly Lys Trp Tyr Leu Val Gly Leu Ala Gly Asn Ala Ile Leu Arg
            30              35              40

Glu Asp Lys Asp Pro Gln Lys Met Tyr Ala Thr Ile Tyr Glu Leu Lys
 45              50                  55

Glu Asp Lys Ser Tyr Asn Val Thr Ser Val Leu Phe Arg Lys Lys Lys
 60              65              70                      75

Cys Asp Tyr Trp Ile Arg Thr Phe Val Pro Gly Cys Gln Pro Gly Glu
                80              85                  90

Phe Thr Leu Gly Asn Ile Lys Ser Tyr Pro Gly Leu Thr Ser Tyr Leu
             95             100                 105

Val Arg Val Val Ser Thr Asn Tyr Asn Gln His Ala Met Val Phe Phe
             110            115                 120

Lys Lys Val Ser Gln Asn Arg Glu Tyr Phe Lys Ile Thr Ile Tyr Gly
             125            130                 135

Arg Thr Lys Glu Leu Pro Ser Glu Leu Lys Glu Asn Phe Ile Arg Phe
140              145                 150                 155

Ser Lys Ser Leu Gly Leu Pro Glu Asn His Ile Val Phe Pro Val Pro
                 160                 165                 170

Ile Asp Gln Cys Ile Asp Gly Ser Ala Trp Ser His Pro Gln Phe Glu
             175                 180                 185

Lys Gln Ala Gly Gly Gly Ser Gly Gly Gly Ser Gly Gly Gly Ser Glu
             190                 195                 200

Gly Gly Gly Ser Glu Gly Gly Gly Ser Glu Gly Gly Gly Ser Glu Gly
             205                 210                 215

Gly Gly Ser Gly Gly Gly Ser Gly Ser Gly Asp Phe Asp Tyr Glu Lys
220                 225                 230                 235

Met Ala Asn Ala Asn Lys Gly Ala Met Thr Glu Asn Ala Asp Glu Asn
                 240                 245                 250

Ala Leu Gln Ser Asp Ala Lys Gly Lys Leu Asp Ser Val Ala Thr Asp
             255                 260                 265

Tyr Gly Ala Ala Ile Asp Gly Phe Ile Gly Asp Val Ser Gly Leu Ala
             270                 275                 280

Asn Gly Asn Gly Ala Thr Gly Asp Phe Ala Gly Ser Asn Ser Gln Met
     285                 290                 295
```

```
Ala Gln Val Gly Asp Gly Asp Asn Ser Pro Leu Met Asn Asn Phe Arg
300                 305                 310                 315

Gln Tyr Leu Pro Ser Leu Pro Gln Ser Val Glu Cys Arg Pro Phe Val
            320                 325                 330

Phe Gly Ala Gly Lys Pro Tyr Glu Phe Ser Ile Asp Cys Asp Lys Ile
                335                 340                 345

Asn Leu Phe Arg Gly Val Phe Ala Phe Leu Leu Tyr Val Ala Thr Phe
            350                 355                 360

Met Tyr Val Phe Ser Thr Phe Ala Asn Ile Leu Arg Asn Lys Glu Ser
            365                 370                 375

<210> SEQ ID NO 15
<211> LENGTH: 258
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: SIGNAL
<222> LOCATION: (-21)..(-1)
<220> FEATURE:
<221> NAME/KEY: CHAIN
<222> LOCATION: (1)..(237)
<223> OTHER INFORMATION: fusion protein of modified hNGAL, Strep-tag II
      and albumin binding domain
<220> FEATURE:
<221> NAME/KEY: MISC_FEATURE
<222> LOCATION: (1)..(178)
<223> OTHER INFORMATION: mature hNGAL
<220> FEATURE:
<221> NAME/KEY: MISC_FEATURE
<222> LOCATION: (179)..(188)
<223> OTHER INFORMATION: Strep-tag II affinity tag
<220> FEATURE:
<221> NAME/KEY: MISC_FEATURE
<222> LOCATION: (189)..(237)
<223> OTHER INFORMATION: albumin binding domain of Protein G

<400> SEQUENCE: 15

Met Lys Lys Thr Ala Ile Ala Ile Ala Val Ala Leu Ala Gly Phe Ala
    -20                 -15                 -10

Thr Val Ala Gln Ala Gln Asp Ser Thr Ser Asp Leu Ile Pro Ala Pro
-5              -1  1               5                   10

Pro Leu Ser Lys Val Pro Leu Gln Gln Asn Phe Gln Asp Asn Gln Phe
            15                  20                  25

Gln Gly Lys Trp Tyr Leu Val Gly Leu Ala Gly Asn Ala Ile Leu Arg
        30                  35                  40

Glu Asp Lys Asp Pro Gln Lys Met Tyr Ala Thr Ile Tyr Glu Leu Lys
45                  50                  55

Glu Asp Lys Ser Tyr Asn Val Thr Ser Val Leu Phe Arg Lys Lys Lys
60                  65                  70                  75

Cys Asp Tyr Trp Ile Arg Thr Phe Val Pro Gly Cys Gln Pro Gly Glu
                80                  85                  90

Phe Thr Leu Gly Asn Ile Lys Ser Tyr Pro Gly Leu Thr Ser Tyr Leu
            95                  100                 105

Val Arg Val Val Ser Thr Asn Tyr Asn Gln His Ala Met Val Phe Phe
        110                 115                 120

Lys Lys Val Ser Gln Asn Arg Glu Tyr Phe Lys Ile Thr Ile Tyr Gly
    125                 130                 135

Arg Thr Lys Glu Leu Pro Ser Glu Leu Lys Glu Asn Phe Ile Arg Phe
140                 145                 150                 155
```

```
Ser Lys Ser Leu Gly Leu Pro Glu Asn His Ile Val Phe Pro Val Pro
            160                 165                 170

Ile Asp Gln Cys Ile Asp Gly Ser Ala Trp Ser His Pro Gln Phe Glu
            175                 180                 185

Lys Pro Ala Ser Leu Ala Glu Ala Lys Val Leu Ala Asn Arg Glu Leu
            190                 195                 200

Asp Lys Tyr Gly Val Ser Asp Tyr Tyr Lys Asn Leu Ile Asn Asn Ala
            205                 210                 215

Lys Thr Val Glu Gly Val Lys Ala Leu Ile Asp Glu Ile Leu Ala Ala
220                 225                 230                 235

Leu Pro

<210> SEQ ID NO 16
<211> LENGTH: 183
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: SIGNAL
<222> LOCATION: (-21)..(-1)
<220> FEATURE:
<221> NAME/KEY: MISC_FEATURE
<222> LOCATION: (1)..(152)
<223> OTHER INFORMATION: mature human tear Lipocalin
<220> FEATURE:
<221> NAME/KEY: MISC_FEATURE
<222> LOCATION: (153)..(162)
<223> OTHER INFORMATION: Strep-tag II affinity tag

<400> SEQUENCE: 16

Met Lys Lys Thr Ala Ile Ala Ile Ala Val Ala Leu Ala Gly Phe Ala
    -20                 -15                 -10

Thr Val Ala Gln Ala Ala Ser Asp Glu Glu Ile Gln Asp Val Ser Gly
-5              -1   1               5                   10

Thr Trp Tyr Leu Lys Ala Met Thr Val Asp Arg Glu Phe Pro Glu Met
            15                  20                  25

Asn Leu Glu Ser Val Thr Pro Met Thr Leu Thr Thr Leu Glu Gly Gly
            30                  35                  40

Asn Leu Glu Ala Lys Val Thr Met Leu Ile Ser Gly Arg Cys Gln Glu
            45                  50                  55

Val Lys Ala Val Leu Glu Lys Thr Asp Glu Pro Gly Lys Tyr Thr Ala
60                  65                  70                  75

Asp Gly Gly Lys His Val Ala Tyr Ile Ile Arg Ser His Val Lys Asp
                80                  85                  90

His Tyr Ile Phe Tyr Ser Glu Gly Glu Leu His Gly Lys Pro Val Arg
            95                  100                 105

Arg Val Lys Leu Val Gly Arg Asp Pro Lys Asn Asn Leu Glu Ala Leu
            110                 115                 120

Glu Asp Phe Glu Lys Ala Ala Gly Ala Arg Gly Leu Ser Thr Glu Ser
            125                 130                 135

Ile Leu Ile Pro Arg Gln Ser Glu Thr Cys Ser Pro Gly Ser Ala Trp
140                 145                 150                 155

Ser His Pro Gln Phe Glu Lys
                160

<210> SEQ ID NO 17
<211> LENGTH: 179
<212> TYPE: PRT
```

```
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MISC_FEATURE
<222> LOCATION: (1)..(179)
<223> OTHER INFORMATION: Mutein Tipca

<400> SEQUENCE: 17

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Cys Ile Val Arg Gln Asp Leu Leu Pro
        35                  40                  45

Ser Met Met Tyr Ala Thr Ile Tyr Glu Leu Lys Glu Asp Lys Ser Tyr
    50                  55                  60

Asn Val Thr Ser Val Leu Phe Met Asp Lys Lys Cys Arg Tyr Tyr Ile
65                  70                  75                  80

Arg Thr Phe Val Pro Gly Ser Gln Pro Gly Glu Phe Thr Leu Gly Asn
                85                  90                  95

Ile Lys Ser Tyr Gly Ile Val Thr Ser Tyr Leu Val Arg Val Val Ser
            100                 105                 110

Thr Asn Tyr Asn Gln His Ala Met Val Phe Phe Lys Ser Val Met Thr
        115                 120                 125

Asn Gln Glu Ala Phe Lys Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide derived from human thrombospondin 1
<220> FEATURE:
<221> NAME/KEY: MOD_RES
<222> LOCATION: (9)..(10)
<223> OTHER INFORMATION: Amino caproic acid
<220> FEATURE:
<221> NAME/KEY: MOD_RES
<222> LOCATION: (11)
<223> OTHER INFORMATION: biotinylation

<400> SEQUENCE: 18

Arg Phe Tyr Val Val Met Trp Lys Xaa Xaa Lys
1               5                   10

<210> SEQ ID NO 19
<211> LENGTH: 1231
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(84)
```

```
<220> FEATURE:
<221> NAME/KEY: sig_peptide
<222> LOCATION: (22)..(84)
<220> FEATURE:
<221> NAME/KEY: CDS
<222> LOCATION: (85)..(618)
<223> OTHER INFORMATION: mature hNGAL
<220> FEATURE:
<221> NAME/KEY: mat_peptide
<222> LOCATION: (85)..(1221)
<223> OTHER INFORMATION: fusion protein of modified hNGAL, Strep-tag II
      and fragment of phage coat protein pIII
<220> FEATURE:
<221> NAME/KEY: CDS
<222> LOCATION: (619)..(648)
<223> OTHER INFORMATION: Strep-tag II affinity tag
<220> FEATURE:
<221> NAME/KEY: CDS
<222> LOCATION: (649)..(651)
<223> OTHER INFORMATION: amber stop codon
<220> FEATURE:
<221> NAME/KEY: CDS
<222> LOCATION: (652)..(1221)
<223> OTHER INFORMATION: codes for amino acids 217-406 of coat protein
      pIII

<400> SEQUENCE: 19
tctagataac gagggcaaaa a atg aaa aag aca gct atc gcg att gca gtg       51
                         Met Lys Lys Thr Ala Ile Ala Ile Ala Val
                          -20                 -15 gct ctg gct ggc ttc gct acc gta gcg cag gcc cag gac tcc acc tca       99
Ala Leu Ala Gly Phe Ala Thr Val Ala Gln Ala Gln Asp Ser Thr Ser
    -10                  -5              -1  1               5 gac ctg atc cca gcc cca cct ctg agc aag gtc cct ctg cag cag aac      147
Asp Leu Ile Pro Ala Pro Pro Leu Ser Lys Val Pro Leu Gln Gln Asn
                 10                  15                  20 ttc cag gac aac caa ttc cat ggg aag tgg tat ctg gta ggt ctc gca      195
Phe Gln Asp Asn Gln Phe His Gly Lys Trp Tyr Leu Val Gly Leu Ala
             25                  30                  35 ggg aat gca att ctc aga gaa gac aaa gac ccg caa aag atg tat gcc      243
Gly Asn Ala Ile Leu Arg Glu Asp Lys Asp Pro Gln Lys Met Tyr Ala
         40                  45                  50 acc atc tat gag ctg aaa gaa gac aag agc tac aat gtc acc tcc gtc      291
Thr Ile Tyr Glu Leu Lys Glu Asp Lys Ser Tyr Asn Val Thr Ser Val
     55                  60                  65 ctg ttt agg aaa aag aag tgt gac tac tgg atc agg act ttt gtt cca      339
Leu Phe Arg Lys Lys Lys Cys Asp Tyr Trp Ile Arg Thr Phe Val Pro
 70                  75                  80                  85 ggt tcc cag cca ggc gag ttc acg ctg ggc aac att aag agt tac cct      387
Gly Ser Gln Pro Gly Glu Phe Thr Leu Gly Asn Ile Lys Ser Tyr Pro
                 90                  95                 100 gga tta acg agt tac ctc gtc cga gtg gtg agc acc aac tac aac cag      435
Gly Leu Thr Ser Tyr Leu Val Arg Val Val Ser Thr Asn Tyr Asn Gln
            105                 110                 115 cat gct atg gtg ttc ttt aag aaa gtt tct caa aac agg gag tac ttc      483
His Ala Met Val Phe Phe Lys Lys Val Ser Gln Asn Arg Glu Tyr Phe
        120                 125                 130 aag att acc atc tac ggg aga acc aag gag ctg gct tcg gaa cta aag      531
Lys Ile Thr Ile Tyr Gly Arg Thr Lys Glu Leu Ala Ser Glu Leu Lys
    135                 140                 145 gag aac ttc atc cgc ttc tct aaa tct ctg ggc ctc cct gaa aac cac      579
Glu Asn Phe Ile Arg Phe Ser Lys Ser Leu Gly Leu Pro Glu Asn His
150                 155                 160                 165 atc gtc ttc cct gtc cca atc gac cag tgt atc gac ggc agc gct tgg      627
Ile Val Phe Pro Val Pro Ile Asp Gln Cys Ile Asp Gly Ser Ala Trp
                170                 175                 180
```

```
tcc cac ccg cag ttc gaa aaa tag gct ggc ggc ggt tct ggt ggt ggt        675
Ser His Pro Gln Phe Glu Lys Gln Ala Gly Gly Gly Ser Gly Gly Gly
        185                 190                 195 tct ggc ggc ggc tct gag ggt ggt ggc tct gag ggt ggc ggt tct gag        723
Ser Gly Gly Gly Ser Glu Gly Gly Gly Ser Glu Gly Gly Gly Ser Glu
200                 205                 210 ggt ggc ggc tct gag gga ggc ggt tcc ggt ggt ggc tct ggt tcc ggt        771
Gly Gly Gly Ser Glu Gly Gly Gly Ser Gly Gly Gly Ser Gly Ser Gly
        215                 220                 225 gat ttt gat tat gaa aag atg gca aac gct aat aag ggg gct atg acc        819
Asp Phe Asp Tyr Glu Lys Met Ala Asn Ala Asn Lys Gly Ala Met Thr
230                 235                 240                 245 gaa aat gcc gat gaa aac gcg cta cag tct gac gct aaa ggc aaa ctt        867
Glu Asn Ala Asp Glu Asn Ala Leu Gln Ser Asp Ala Lys Gly Lys Leu
        250                 255                 260 gat tct gtc gct act gat tac ggt gct gct atc gat ggt ttc att ggt        915
Asp Ser Val Ala Thr Asp Tyr Gly Ala Ala Ile Asp Gly Phe Ile Gly
265                 270                 275 gac gtt tcc ggc ctt gct aat ggt aat ggt gct act ggt gat ttt gct        963
Asp Val Ser Gly Leu Ala Asn Gly Asn Gly Ala Thr Gly Asp Phe Ala
        280                 285                 290 ggc tct aat tcc caa atg gct caa gtc ggt gac ggt gat aat tca cct       1011
Gly Ser Asn Ser Gln Met Ala Gln Val Gly Asp Gly Asp Asn Ser Pro
295                 300                 305 tta atg aat aat ttc cgt caa tat tta cct tcc ctc cct caa tcg gtt       1059
Leu Met Asn Asn Phe Arg Gln Tyr Leu Pro Ser Leu Pro Gln Ser Val
310                 315                 320                 325 gaa tgt cgc cct ttt gtc ttt ggc gct ggt aaa cca tat gaa ttt tct       1107
Glu Cys Arg Pro Phe Val Phe Gly Ala Gly Lys Pro Tyr Glu Phe Ser
        330                 335                 340 att gat tgt gac aaa ata aac tta ttc cgt ggt gtc ttt gcg ttt ctt       1155
Ile Asp Cys Asp Lys Ile Asn Leu Phe Arg Gly Val Phe Ala Phe Leu
                345                 350                 355 tta tat gtt gcc acc ttt atg tat gta ttt tct acg ttt gct aac ata       1203
Leu Tyr Val Ala Thr Phe Met Tyr Val Phe Ser Thr Phe Ala Asn Ile
        360                 365                 370 ctg cgt aat aag gag tct taataagctt                                    1231
Leu Arg Asn Lys Glu Ser
        375
```

<210> SEQ ID NO 20
<211> LENGTH: 400
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: SIGNAL
<222> LOCATION: (-21)..(-1)
<220> FEATURE:
<221> NAME/KEY: CHAIN
<222> LOCATION: (1)..(379)
<223> OTHER INFORMATION: fusion protein of modified hNGAL, Strep-tag II
      and fragment of phage coat protein pIII
<220> FEATURE:
<221> NAME/KEY: MISC_FEATURE
<222> LOCATION: (1)..(178)
<223> OTHER INFORMATION: mature modified hNGAL
<220> FEATURE:
<221> NAME/KEY: MISC_FEATURE
<222> LOCATION: (179)..(188)
<223> OTHER INFORMATION: Strep-tag II affinity tag
<220> FEATURE:
<221> NAME/KEY: MISC_FEATURE -continued

```
<222> LOCATION: (189)
<223> OTHER INFORMATION: amber stop codon
<220> FEATURE:
<221> NAME/KEY: MISC_FEATURE
<222> LOCATION: (190)..(379)
<223> OTHER INFORMATION: amino acids 217-406 of coat protein pIII

<400> SEQUENCE: 20
```

Met Lys Lys Thr Ala Ile Ala Ile Ala Val Ala Leu Ala Gly Phe Ala
    -20                 -15                 -10

Thr Val Ala Gln Ala Gln Asp Ser Thr Ser Asp Leu Ile Pro Ala Pro
-5              -1  1               5                   10

Pro Leu Ser Lys Val Pro Leu Gln Gln Asn Phe Gln Asp Asn Gln Phe
            15                  20                  25

His Gly Lys Trp Tyr Leu Val Gly Leu Ala Gly Asn Ala Ile Leu Arg
            30                  35                  40

Glu Asp Lys Asp Pro Gln Lys Met Tyr Ala Thr Ile Tyr Glu Leu Lys
            45                  50                  55

Glu Asp Lys Ser Tyr Asn Val Thr Ser Val Leu Phe Arg Lys Lys Lys
60              65                  70                  75

Cys Asp Tyr Trp Ile Arg Thr Phe Val Pro Gly Ser Gln Pro Gly Glu
                80                  85                  90

Phe Thr Leu Gly Asn Ile Lys Ser Tyr Pro Gly Leu Thr Ser Tyr Leu
                95                  100                 105

Val Arg Val Val Ser Thr Asn Tyr Asn Gln His Ala Met Val Phe Phe
            110                 115                 120

Lys Lys Val Ser Gln Asn Arg Glu Tyr Phe Lys Ile Thr Ile Tyr Gly
            125                 130                 135

Arg Thr Lys Glu Leu Ala Ser Glu Leu Lys Glu Asn Phe Ile Arg Phe
140                 145                 150                 155

Ser Lys Ser Leu Gly Leu Pro Glu Asn His Ile Val Phe Pro Val Pro
                160                 165                 170

Ile Asp Gln Cys Ile Asp Gly Ser Ala Trp Ser His Pro Gln Phe Glu
                175                 180                 185

Lys Gln Ala Gly Gly Ser Gly Gly Ser Gly Gly Ser Glu
            190                 195                 200

Gly Gly Gly Ser Glu Gly Gly Ser Glu Gly Gly Ser Glu Gly
    205                 210                 215

Gly Gly Ser Gly Gly Ser Gly Ser Gly Asp Phe Asp Tyr Glu Lys
220                 225                 230                 235

Met Ala Asn Ala Asn Lys Gly Ala Met Thr Glu Asn Ala Asp Glu Asn
            240                 245                 250

Ala Leu Gln Ser Asp Ala Lys Gly Lys Leu Asp Ser Val Ala Thr Asp
            255                 260                 265

Tyr Gly Ala Ala Ile Asp Gly Phe Ile Gly Asp Val Ser Gly Leu Ala
            270                 275                 280

Asn Gly Asn Gly Ala Thr Gly Asp Phe Ala Gly Ser Asn Ser Gln Met
            285                 290                 295

Ala Gln Val Gly Asp Gly Asp Asn Ser Pro Leu Met Asn Asn Phe Arg
300                 305                 310                 315

Gln Tyr Leu Pro Ser Leu Pro Gln Ser Val Glu Cys Arg Pro Phe Val
                320                 325                 330

Phe Gly Ala Gly Lys Pro Tyr Glu Phe Ser Ile Asp Cys Asp Lys Ile
            335                 340                 345

Asn Leu Phe Arg Gly Val Phe Ala Phe Leu Leu Tyr Val Ala Thr Phe

Met Tyr Val Phe Ser Thr Phe Ala Asn Ile Leu Arg Asn Lys Glu Ser
365                 370                 375

<210> SEQ ID NO 21
<211> LENGTH: 658
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (22)..(84)
<220> FEATURE:
<221> NAME/KEY: sig_peptide
<222> LOCATION: (22)..(84)
<220> FEATURE:
<221> NAME/KEY: CDS
<222> LOCATION: (85)..(618)
<223> OTHER INFORMATION: mature hNGAL
<220> FEATURE:
<221> NAME/KEY: mat_peptide
<222> LOCATION: (85)..(648)
<223> OTHER INFORMATION: fusion protein of modified hNGAL and Strep-tag
      II
<220> FEATURE:
<221> NAME/KEY: CDS
<222> LOCATION: (619)..(648)
<223> OTHER INFORMATION: Strep-tag II affinity tag

<400> SEQUENCE: 21

```
tctagataac gagggcaaaa a atg aaa aag aca gct atc gcg att gca gtg         51
                         Met Lys Lys Thr Ala Ile Ala Ile Ala Val
                             -20                 -15 gct ctg gct ggc ttc gct acc gta gcg cag gcc cag gac tcc acc tca         99
Ala Leu Ala Gly Phe Ala Thr Val Ala Gln Ala Gln Asp Ser Thr Ser
    -10                 -5              -1  1               5 gac ctg atc cca gcc cca cct ctg agc aag gtc cct ctg cag cag aac        147
Asp Leu Ile Pro Ala Pro Pro Leu Ser Lys Val Pro Leu Gln Gln Asn
                10              15                  20 ttc cag gac aac caa ttc cag ggg aag tgg tat ctg gta ggt ctc gca        195
Phe Gln Asp Asn Gln Phe Gln Gly Lys Trp Tyr Leu Val Gly Leu Ala
            25                  30                  35 ggg aat gca att ctc aga gaa gac aaa gac ccg caa aag atg tat gcc        243
Gly Asn Ala Ile Leu Arg Glu Asp Lys Asp Pro Gln Lys Met Tyr Ala
        40                  45                  50 acc atc tat gag ctg aaa gaa gac aag agc tac aat gtc acc tcc gtc        291
Thr Ile Tyr Glu Leu Lys Glu Asp Lys Ser Tyr Asn Val Thr Ser Val
    55                  60                  65 ctg ttt agg aaa aag aag tgt gac tac tgg atc agg act ttt gtt cca        339
Leu Phe Arg Lys Lys Lys Cys Asp Tyr Trp Ile Arg Thr Phe Val Pro
70                  75                  80                  85 ggt tcc cag cca ggc gag ttc acg ctg ggc aac att aag agt tac cct        387
Gly Ser Gln Pro Gly Glu Phe Thr Leu Gly Asn Ile Lys Ser Tyr Pro
                90                  95                  100 gga tta acg agt tac ctc gtc cga gtg gtg agc acc aac tac aac cag        435
Gly Leu Thr Ser Tyr Leu Val Arg Val Val Ser Thr Asn Tyr Asn Gln
            105                 110                 115 cat gct atg gtg ttc ttt aag aaa gtt tct caa aac agg gag tac ttc        483
His Ala Met Val Phe Phe Lys Lys Val Ser Gln Asn Arg Glu Tyr Phe
        120                 125                 130 aag att acc atc tac ggg aga acc aag gag ctg cct tcg gaa cta aag        531
Lys Ile Thr Ile Tyr Gly Arg Thr Lys Glu Leu Pro Ser Glu Leu Lys
    135                 140                 145
```

```
gag aac ttc atc cgc ttc tcc aaa tct ctg ggc ctc cct gaa aac cac    579
Glu Asn Phe Ile Arg Phe Ser Lys Ser Leu Gly Leu Pro Glu Asn His
150                 155                 160                 165 atc gtc ttc cct gtc cca atc gac cag tgt atc gac ggc agc gct tgg    627
Ile Val Phe Pro Val Pro Ile Asp Gln Cys Ile Asp Gly Ser Ala Trp
                170                 175                 180 tcc cac ccg cag ttc gaa aaa taataagctt                              658
Ser His Pro Gln Phe Glu Lys
                185

<210> SEQ ID NO 22
<211> LENGTH: 209
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: SIGNAL
<222> LOCATION: (-21)..(-1)
<220> FEATURE:
<221> NAME/KEY: CHAIN
<222> LOCATION: (1)..(188)
<223> OTHER INFORMATION: fusion protein of modified hNGAL and Strep-tag
      II
<220> FEATURE:
<221> NAME/KEY: MISC_FEATURE
<222> LOCATION: (1)..(178)
<223> OTHER INFORMATION: mature modified hNGAL
<220> FEATURE:
<221> NAME/KEY: MISC_FEATURE
<222> LOCATION: (179)..(188)
<223> OTHER INFORMATION: Strep-tag II affinity tag

<400> SEQUENCE: 22

Met Lys Lys Thr Ala Ile Ala Ile Ala Val Ala Leu Ala Gly Phe Ala
    -20                 -15                 -10

Thr Val Ala Gln Ala Gln Asp Ser Thr Ser Asp Leu Ile Pro Ala Pro
 -5              -1   1               5                  10

Pro Leu Ser Lys Val Pro Leu Gln Gln Asn Phe Gln Asp Asn Gln Phe
                15                  20                  25

Gln Gly Lys Trp Tyr Leu Val Gly Leu Ala Gly Asn Ala Ile Leu Arg
            30                  35                  40

Glu Asp Lys Asp Pro Gln Lys Met Tyr Ala Thr Ile Tyr Glu Leu Lys
45                  50                  55

Glu Asp Lys Ser Tyr Asn Val Thr Ser Val Leu Phe Arg Lys Lys Lys
60                  65                  70                  75

Cys Asp Tyr Trp Ile Arg Thr Phe Val Pro Gly Ser Gln Pro Gly Glu
                80                  85                  90

Phe Thr Leu Gly Asn Ile Lys Ser Tyr Pro Gly Leu Thr Ser Tyr Leu
                95                  100                 105

Val Arg Val Val Ser Thr Asn Tyr Asn Gln His Ala Met Val Phe Phe
            110                 115                 120

Lys Lys Val Ser Gln Asn Arg Glu Tyr Phe Lys Ile Thr Ile Tyr Gly
            125                 130                 135

Arg Thr Lys Glu Leu Pro Ser Glu Leu Lys Glu Asn Phe Ile Arg Phe
140                 145                 150                 155

Ser Lys Ser Leu Gly Leu Pro Glu Asn His Ile Val Phe Pro Val Pro
                160                 165                 170

Ile Asp Gln Cys Ile Asp Gly Ser Ala Trp Ser His Pro Gln Phe Glu
            175                 180                 185

Lys
```

<210> SEQ ID NO 23
<211> LENGTH: 534
<212> TYPE: DNA
<213> ORGANISM: Artificial Sequence
<220> FEATURE:
<223> OTHER INFORMATION: Description of Artificial Sequence: Synthetic nucleotide sequence
<220> FEATURE:
<221> NAME/KEY: CDS
<222> LOCATION: (1)..(534)
<223> OTHER INFORMATION: Mutein RFY-B

<400> SEQUENCE: 23

| cag | gac | tcc | acc | tca | gac | ctg | atc | cca | gcc | cca | cct | ctg | agc | aag | gtc | 48 |
|---|---|---|---|---|---|---|---|---|---|---|---|---|---|---|---|---|
| Gln | Asp | Ser | Thr | Ser | Asp | Leu | Ile | Pro | Ala | Pro | Pro | Leu | Ser | Lys | Val | |
| 1 | | | | 5 | | | | | 10 | | | | | 15 | | |

| cct | ctg | cag | cag | aac | ttc | cag | gac | aac | caa | ttc | cag | ggg | aag | tgg | tat | 96 |
|---|---|---|---|---|---|---|---|---|---|---|---|---|---|---|---|---|
| Pro | Leu | Gln | Gln | Asn | Phe | Gln | Asp | Asn | Gln | Phe | Gln | Gly | Lys | Trp | Tyr | |
| | | | 20 | | | | | 25 | | | | | 30 | | | |

| ctg | gta | ggt | ctc | gca | ggg | aat | ggg | att | acg | aga | tat | gac | cgg | ctg | ccg | 144 |
|---|---|---|---|---|---|---|---|---|---|---|---|---|---|---|---|---|
| Leu | Val | Gly | Leu | Ala | Gly | Asn | Gly | Ile | Thr | Arg | Tyr | Asp | Arg | Leu | Pro | |
| | | 35 | | | | | 40 | | | | | 45 | | | | |

| tct | gtg | atg | tat | gcc | acc | atc | tat | gag | ctg | aaa | gaa | gac | aag | agc | tac | 192 |
|---|---|---|---|---|---|---|---|---|---|---|---|---|---|---|---|---|
| Ser | Val | Met | Tyr | Ala | Thr | Ile | Tyr | Glu | Leu | Lys | Glu | Asp | Lys | Ser | Tyr | |
| 50 | | | | | 55 | | | | | 60 | | | | | | |

| aat | gtc | acc | tcc | gtc | gat | ttt | tgg | gct | aag | aag | tgt | aat | tac | aag | atc | 240 |
|---|---|---|---|---|---|---|---|---|---|---|---|---|---|---|---|---|
| Asn | Val | Thr | Ser | Val | Asp | Phe | Trp | Ala | Lys | Lys | Cys | Asn | Tyr | Lys | Ile | |
| 65 | | | | | 70 | | | | | 75 | | | | | 80 | |

| agg | act | ttt | gtt | cca | ggt | tcc | cag | cca | ggc | gag | ttc | acg | ctg | ggc | aac | 288 |
|---|---|---|---|---|---|---|---|---|---|---|---|---|---|---|---|---|
| Arg | Thr | Phe | Val | Pro | Gly | Ser | Gln | Pro | Gly | Glu | Phe | Thr | Leu | Gly | Asn | |
| | | | | 85 | | | | | 90 | | | | | 95 | | |

| att | aag | agt | tac | gat | ctg | ctt | acg | agt | ttc | ctc | gtc | cga | gtg | gtg | agc | 336 |
|---|---|---|---|---|---|---|---|---|---|---|---|---|---|---|---|---|
| Ile | Lys | Ser | Tyr | Asp | Leu | Leu | Thr | Ser | Phe | Leu | Val | Arg | Val | Val | Ser | |
| | | | 100 | | | | | 105 | | | | | 110 | | | |

| acc | aac | tac | aac | cag | cat | gct | atg | gtg | ttc | ttt | aag | ccg | gtt | ggg | ggg | 384 |
|---|---|---|---|---|---|---|---|---|---|---|---|---|---|---|---|---|
| Thr | Asn | Tyr | Asn | Gln | His | Ala | Met | Val | Phe | Phe | Lys | Pro | Val | Gly | Gly | |
| | | 115 | | | | | 120 | | | | | 125 | | | | |

| aac | att | gag | tgg | ttc | aag | att | acc | atc | tac | ggg | aga | acc | aag | gag | ctg | 432 |
|---|---|---|---|---|---|---|---|---|---|---|---|---|---|---|---|---|
| Asn | Ile | Glu | Trp | Phe | Lys | Ile | Thr | Ile | Tyr | Gly | Arg | Thr | Lys | Glu | Leu | |
| 130 | | | | | 135 | | | | | 140 | | | | | | |

| cct | tcg | gaa | cta | aag | gag | aac | ttc | atc | cgc | ttc | tcc | aaa | tct | ctg | ggc | 480 |
|---|---|---|---|---|---|---|---|---|---|---|---|---|---|---|---|---|
| Pro | Ser | Glu | Leu | Lys | Glu | Asn | Phe | Ile | Arg | Phe | Ser | Lys | Ser | Leu | Gly | |
| 145 | | | | | 150 | | | | | 155 | | | | | 160 | |

| ctc | cct | gaa | aac | cac | atc | gtc | ttc | cct | gtc | cca | atc | gac | cag | tgt | atc | 528 |
|---|---|---|---|---|---|---|---|---|---|---|---|---|---|---|---|---|
| Leu | Pro | Glu | Asn | His | Ile | Val | Phe | Pro | Val | Pro | Ile | Asp | Gln | Cys | Ile | |
| | | | | 165 | | | | | 170 | | | | | 175 | | |

| gac | ggc | | | | | | | | | | | | | | | 534 |
|---|---|---|---|---|---|---|---|---|---|---|---|---|---|---|---|---|
| Asp | Gly | | | | | | | | | | | | | | | |

<210> SEQ ID NO 24
<211> LENGTH: 178
<212> TYPE: PRT
<213> ORGANISM: Artificial Sequence
<220> FEATURE:
<223> OTHER INFORMATION: Description of Artificial Sequence: Synthetic amino acid sequence
<220> FEATURE:
<221> NAME/KEY: MISC_FEATURE
<222> LOCATION: (1)..(178)
<223> OTHER INFORMATION: Mutein RFY-B

<400> SEQUENCE: 24

Gln Asp Ser Thr Ser Asp Leu Ile Pro Ala Pro Pro Leu Ser Lys Val

```
              1               5                  10                 15
Pro Leu Gln Gln Asn Phe Gln Asp Asn Gln Phe Gln Gly Lys Trp Tyr
                20                  25                  30

Leu Val Gly Leu Ala Gly Asn Gly Ile Thr Arg Tyr Asp Arg Leu Pro
                35                  40                  45

Ser Val Met Tyr Ala Thr Ile Tyr Glu Leu Lys Glu Asp Lys Ser Tyr
 50                      55                  60

Asn Val Thr Ser Val Asp Phe Trp Ala Lys Lys Cys Asn Tyr Lys Ile
 65                      70                  75                  80

Arg Thr Phe Val Pro Gly Ser Gln Pro Gly Glu Phe Thr Leu Gly Asn
                85                  90                  95

Ile Lys Ser Tyr Asp Leu Leu Thr Ser Phe Leu Val Arg Val Val Ser
                100                 105                 110

Thr Asn Tyr Asn Gln His Ala Met Val Phe Phe Lys Pro Val Gly Gly
                115                 120                 125

Asn Ile Glu Trp Phe Lys Ile Thr Ile Tyr Gly Arg Thr Lys Glu Leu
                130                 135                 140

Pro Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 25
<211> LENGTH: 534
<212> TYPE: DNA
<213> ORGANISM: Artificial Sequence
<220> FEATURE:
<223> OTHER INFORMATION: Description of Artificial Sequence: Synthetic nucleotide sequence
<220> FEATURE:
<221> NAME/KEY: CDS
<222> LOCATION: (1)..(534)
<223> OTHER INFORMATION: Mutein RFY-C

<400> SEQUENCE: 25

```
cag gac tcc acc tca gac ctg atc cca gcc cca cct ctg agc aag gtc        48
Gln Asp Ser Thr Ser Asp Leu Ile Pro Ala Pro Pro Leu Ser Lys Val
 1               5                  10                  15 cct ctg cag cag aac ttc cag gac aac caa ttc cag ggg aag tgg tat        96
Pro Leu Gln Gln Asn Phe Gln Asp Asn Gln Phe Gln Gly Lys Trp Tyr
                20                  25                  30 ctg gta ggt ctc gca ggg aat ggg att cat aga ctg gac aat gtt ccg       144
Leu Val Gly Leu Ala Gly Asn Gly Ile His Arg Leu Asp Asn Val Pro
            35                  40                  45 cct aat atg tat gcc acc atc tat gag ctg aaa gaa gac aag agc tac       192
Pro Asn Met Tyr Ala Thr Ile Tyr Glu Leu Lys Glu Asp Lys Ser Tyr
 50                  55                  60 aat gtc acc tcc gtc gat ttt ctt atg aag aag tgt ccg tac ttt atc       240
Asn Val Thr Ser Val Asp Phe Leu Met Lys Lys Cys Pro Tyr Phe Ile
 65                  70                  75                  80 agg act ttt gtt cca ggt tcc cag cca ggc gag ttc acg ctg ggc aac       288
Arg Thr Phe Val Pro Gly Ser Gln Pro Gly Glu Phe Thr Leu Gly Asn
                85                  90                  95 att aag agt tac ccg ttt ctt acg agt ttc ctc gtc cga gtg gtg agc       336
Ile Lys Ser Tyr Pro Phe Leu Thr Ser Phe Leu Val Arg Val Val Ser
                100                 105                 110 acc aac tac aac cag cat gct atg gtg ttc ttt aag aat gtt cct agg       384
Thr Asn Tyr Asn Gln His Ala Met Val Phe Phe Lys Asn Val Pro Arg
```

```
aac tat gag gag ttc aag att acc atc tac ggg aga acc aag gag ctg      432
Asn Tyr Glu Glu Phe Lys Ile Thr Ile Tyr Gly Arg Thr Lys Glu Leu
        130                 135                 140 cct tcg gaa cta aag gag aac ttc atc cgc ttc tcc aaa tct ctg ggc      480
Pro Ser Glu Leu Lys Glu Asn Phe Ile Arg Phe Ser Lys Ser Leu Gly
145                 150                 155                 160 ctc cct gaa aac cac atc gtc ttc cct gtc cca atc gac cag tgt atc      528
Leu Pro Glu Asn His Ile Val Phe Pro Val Pro Ile Asp Gln Cys Ile
                165                 170                 175 gac ggc                                                               534
Asp Gly
```

<210> SEQ ID NO 26
<211> LENGTH: 178
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MISC_FEATURE
<222> LOCATION: (1)..(178)
<223> OTHER INFORMATION: Mutein RFY-C

<400> SEQUENCE: 26

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Leu Val Gly Leu Ala Gly Asn Gly Ile His Arg Leu Asp Asn Val Pro
        35                  40                  45

Pro Asn Met Tyr Ala Thr Ile Tyr Glu Leu Lys Glu Asp Lys Ser Tyr
    50                  55                  60

Asn Val Thr Ser Val Asp Phe Leu Met Lys Lys Cys Pro Tyr Phe Ile
65                  70                  75                  80

Arg Thr Phe Val Pro Gly Ser Gln Pro Gly Glu Phe Thr Leu Gly Asn
                85                  90                  95

Ile Lys Ser Tyr Pro Phe Leu Thr Ser Phe Leu Val Arg Val Val Ser
            100                 105                 110

Thr Asn Tyr Asn Gln His Ala Met Val Phe Lys Asn Val Pro Arg
        115                 120                 125

Asn Tyr Glu Glu Phe Lys Ile Thr Ile Tyr Gly Arg Thr Lys Glu Leu
    130                 135                 140

Pro Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 27
<211> LENGTH: 534
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (1)..(534)
<223> OTHER INFORMATION: Mutein RFY-E

<400> SEQUENCE: 27

| | | | | | | | | | | | | | | | | |
|---|---|---|---|---|---|---|---|---|---|---|---|---|---|---|---|---|
| cag | gac | tcc | acc | tca | gac | ctg | atc | cca | gcc | cca | cct | ctg | agc | aag | gtc | 48 |
| Gln | Asp | Ser | Thr | Ser | Asp | Leu | Ile | Pro | Ala | Pro | Pro | Leu | Ser | Lys | Val | |
| 1 | | | | 5 | | | | | 10 | | | | | 15 | | |
| cct | ctg | cag | cag | aac | ttc | cag | gac | aac | caa | ttc | cag | ggg | aag | tgg | tat | 96 |
| Pro | Leu | Gln | Gln | Asn | Phe | Gln | Asp | Asn | Gln | Phe | Gln | Gly | Lys | Trp | Tyr | |
| | | | 20 | | | | | 25 | | | | | 30 | | | |
| ctg | gta | ggt | ctc | gca | ggg | aat | ggg | att | acg | aga | gtt | gac | acg | ctg | ccg | 144 |
| Leu | Val | Gly | Leu | Ala | Gly | Asn | Gly | Ile | Thr | Arg | Val | Asp | Thr | Leu | Pro | |
| | | | 35 | | | | | 40 | | | | | 45 | | | |
| tct | cgg | atg | tat | gcc | acc | atc | tat | gag | ctg | aaa | gaa | gac | aag | agc | tac | 192 |
| Ser | Arg | Met | Tyr | Ala | Thr | Ile | Tyr | Glu | Leu | Lys | Glu | Asp | Lys | Ser | Tyr | |
| 50 | | | | | 55 | | | | | 60 | | | | | | |
| aat | gtc | acc | tcc | gtc | cct | ttt | atg | ggt | aag | aag | tgt | aag | tac | aag | atc | 240 |
| Asn | Val | Thr | Ser | Val | Pro | Phe | Met | Gly | Lys | Lys | Cys | Lys | Tyr | Lys | Ile | |
| 65 | | | | | 70 | | | | | 75 | | | | | 80 | |
| agg | act | ttt | gtt | cca | ggt | tcc | cag | cca | ggc | gag | ttc | acg | ctg | ggc | aac | 288 |
| Arg | Thr | Phe | Val | Pro | Gly | Ser | Gln | Pro | Gly | Glu | Phe | Thr | Leu | Gly | Asn | |
| | | | | 85 | | | | | 90 | | | | | 95 | | |
| att | aag | agt | tac | atg | tcg | aat | acg | agt | ttc | ctc | gtc | cga | gtg | gtg | agc | 336 |
| Ile | Lys | Ser | Tyr | Met | Ser | Asn | Thr | Ser | Phe | Leu | Val | Arg | Val | Val | Ser | |
| | | | 100 | | | | | 105 | | | | | 110 | | | |
| acc | aac | tac | aac | cag | cat | gct | atg | gtg | ttc | ttt | aag | cag | gtt | cat | aag | 384 |
| Thr | Asn | Tyr | Asn | Gln | His | Ala | Met | Val | Phe | Phe | Lys | Gln | Val | His | Lys | |
| | | | 115 | | | | | 120 | | | | | 125 | | | |
| aac | cct | gag | tct | ttc | aag | att | acc | atc | tac | ggg | aga | acc | aag | gag | ctg | 432 |
| Asn | Pro | Glu | Ser | Phe | Lys | Ile | Thr | Ile | Tyr | Gly | Arg | Thr | Lys | Glu | Leu | |
| 130 | | | | | 135 | | | | | 140 | | | | | | |
| cct | tcg | gaa | cta | aag | gag | aac | ttc | atc | cgc | ttc | tcc | aaa | tct | ctg | ggc | 480 |
| Pro | Ser | Glu | Leu | Lys | Glu | Asn | Phe | Ile | Arg | Phe | Ser | Lys | Ser | Leu | Gly | |
| 145 | | | | | 150 | | | | | 155 | | | | | 160 | |
| ctc | cct | gaa | aac | cac | atc | gtc | ttc | cct | gtc | cca | atc | gac | cag | tgt | atc | 528 |
| Leu | Pro | Glu | Asn | His | Ile | Val | Phe | Pro | Val | Pro | Ile | Asp | Gln | Cys | Ile | |
| | | | | 165 | | | | | 170 | | | | | 175 | | |
| gac | ggc | | | | | | | | | | | | | | | 534 |
| Asp | Gly | | | | | | | | | | | | | | | |

<210> SEQ ID NO 28
<211> LENGTH: 178
<212> TYPE: PRT
<213> ORGANISM: Artificial Sequence
<220> FEATURE:
<223> OTHER INFORMATION: Description of Artificial Sequence: Synthetic
    amino acid sequence
<220> FEATURE:
<221> NAME/KEY: MISC_FEATURE
<222> LOCATION: (1)..(178)
<223> OTHER INFORMATION: Mutein RFY-E

<400> SEQUENCE: 28

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Leu Val Gly Leu Ala Gly Asn Gly Ile Thr Arg Val Asp Thr Leu Pro
        35                  40                  45

Ser Arg Met Tyr Ala Thr Ile Tyr Glu Leu Lys Glu Asp Lys Ser Tyr
    50                  55                  60

Asn Val Thr Ser Val Pro Phe Met Gly Lys Lys Cys Lys Tyr Lys Ile
65                  70                  75                  80

Arg Thr Phe Val Pro Gly Ser Gln Pro Gly Glu Phe Thr Leu Gly Asn
                85                  90                  95

Ile Lys Ser Tyr Met Ser Asn Thr Ser Phe Leu Val Arg Val Val Ser
            100                 105                 110

Thr Asn Tyr Asn Gln His Ala Met Val Phe Phe Lys Gln Val His Lys
        115                 120                 125

Asn Pro Glu Ser Phe Lys Ile Thr Ile Tyr Gly Arg Thr Lys Glu Leu
    130                 135                 140

Pro Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 29
<211> LENGTH: 77
<212> TYPE: PRT
<213> ORGANISM: Homo sapiens
<220> FEATURE:
<221> NAME/KEY: MISC_FEATURE
<222> LOCATION: (1)..(77)
<223> OTHER INFORMATION: recombinant human interleukin-8

<400> SEQUENCE: 29

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser
65                  70                  75

<210> SEQ ID NO 30
<211> LENGTH: 534
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (1)..(534)
<223> OTHER INFORMATION: Mutein N4

<400> SEQUENCE: 30 cag gac tcc acc tca gac ctg atc cca gcc cca cct ctg agc aag gtc      48
Gln Asp Ser Thr Ser Asp Leu Ile Pro Ala Pro Pro Leu Ser Lys Val
1               5                   10                  15 cct ctg cag cag aac ttc cag gac aac caa ttc cag ggg aag tgg tat      96
Pro Leu Gln Gln Asn Phe Gln Asp Asn Gln Phe Gln Gly Lys Trp Tyr
            20                  25                  30 ctg gta ggt ctc gca ggg aat gat att tat aga gcg gac tct ttg ccg     144
Leu Val Gly Leu Ala Gly Asn Asp Ile Tyr Arg Ala Asp Ser Leu Pro
        35                  40                  45 ggt ttg atg tat gcc acc atc tat gag ctg aaa gaa gac aag agc tac     192
Gly Leu Met Tyr Ala Thr Ile Tyr Glu Leu Lys Glu Asp Lys Ser Tyr
    50                  55                  60

```
aat gtc acc tcc gtc gtt ttt tat gat aag aag tgt gtt tac tcg atc      240
Asn Val Thr Ser Val Val Phe Tyr Asp Lys Lys Cys Val Tyr Ser Ile
 65              70                  75                  80 agg act ttt gtt cca ggt tcc cag cca ggc gag ttc acg ctg ggc aac      288
Arg Thr Phe Val Pro Gly Ser Gln Pro Gly Glu Phe Thr Leu Gly Asn
                 85                  90                  95 att aag agt tac gag gct gtt acg agt ttc ctc gtc cga gtg gtg agc      336
Ile Lys Ser Tyr Glu Ala Val Thr Ser Phe Leu Val Arg Val Val Ser
            100                 105                 110 acc aac tac aac cag cat gct atg gtg ttc ttt aag gat gtt agg ccg      384
Thr Asn Tyr Asn Gln His Ala Met Val Phe Phe Lys Asp Val Arg Pro
        115                 120                 125 aac agt gag gag ttc aag att acc atc tac ggg aga acc aag gag ctg      432
Asn Ser Glu Glu Phe Lys Ile Thr Ile Tyr Gly Arg Thr Lys Glu Leu
    130                 135                 140 cct tcg gaa cta aag gag aac ttc atc cgc ttc tcc aaa tct ctg ggc      480
Pro Ser Glu Leu Lys Glu Asn Phe Ile Arg Phe Ser Lys Ser Leu Gly
145                 150                 155                 160 ctc cct gaa aac cac atc gtc ttc cct gtc cca atc gac cag tgt atc      528
Leu Pro Glu Asn His Ile Val Phe Pro Val Pro Ile Asp Gln Cys Ile
                165                 170                 175 gac ggc                                                              534
Asp Gly <210> SEQ ID NO 31
<211> LENGTH: 522
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (4)..(42)
<223> OTHER INFORMATION: Affinity tag Arg-Gly-Ser-His(6)-Gly(3)
<220> FEATURE:
<221> NAME/KEY: mat_peptide
<222> LOCATION: (4)..(513)
<223> OTHER INFORMATION: fusion protein of tumor necrosis factor alpha
      and affinity tag
<220> FEATURE:
<221> NAME/KEY: CDS
<222> LOCATION: (43)..(513)
<223> OTHER INFORMATION: mature tumor necrosis factor alpha

<400> SEQUENCE: 31 cat atg aga gga tcg cat cac cat cac cat cac ggt ggc ggg gtc aga       48
    Met Arg Gly Ser His His His His His His Gly Gly Gly Val Arg
     1               5                  10                  15 tca tct tct cga acc ccg agt gac aag cct gta gcc cat gtt gta gca       96
Ser Ser Ser Arg Thr Pro Ser Asp Lys Pro Val Ala His Val Val Ala
                 20                  25                  30 aac cct caa gct gag ggg cag ctc cag tgg ctg aac cgc cgg gcc aat      144
Asn Pro Gln Ala Glu Gly Gln Leu Gln Trp Leu Asn Arg Arg Ala Asn
             35                  40                  45 gcc ctc ctg gcc aat ggc gtg gag ctg aga gat aac cag ctg gtg gtg      192
Ala Leu Leu Ala Asn Gly Val Glu Leu Arg Asp Asn Gln Leu Val Val
         50                  55                  60 cca tca gag ggc ctg tac ctc atc tac tcc cag gtc ctc ttc aag ggc      240
Pro Ser Glu Gly Leu Tyr Leu Ile Tyr Ser Gln Val Leu Phe Lys Gly
 65                  70                  75                  80 caa ggc tgc ccc tcc acc cat gtg ctc ctc acc cac acc atc agc cgc      288
Gln Gly Cys Pro Ser Thr His Val Leu Leu Thr His Thr Ile Ser Arg
 80                  85                  90                  95
```

```
atc gcc gtc tcc tac cag acc aag gtc aac ctc ctc tct gcc atc aag      336
Ile Ala Val Ser Tyr Gln Thr Lys Val Asn Leu Leu Ser Ala Ile Lys
            100                 105                 110 agc ccc tgc cag agg gag acc cca gag ggg gct gag gcc aag ccc tgg      384
Ser Pro Cys Gln Arg Glu Thr Pro Glu Gly Ala Glu Ala Lys Pro Trp
        115                 120                 125 tat gag ccc atc tat ctg gga ggg gtc ttc cag ctg gag aag ggt gac      432
Tyr Glu Pro Ile Tyr Leu Gly Gly Val Phe Gln Leu Glu Lys Gly Asp
            130                 135                 140 cga ctc agc gct gag atc aat cgg ccc gac tat ctc gac ttt gcc gag      480
Arg Leu Ser Ala Glu Ile Asn Arg Pro Asp Tyr Leu Asp Phe Ala Glu
        145                 150                 155 tct ggg cag gtc tac ttt ggg atc att gcc ctg tgaaagctt                522
Ser Gly Gln Val Tyr Phe Gly Ile Ile Ala Leu
160                 165                 170

<210> SEQ ID NO 32
<211> LENGTH: 531
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (1)..(531)
<223> OTHER INFORMATION: Mutein TNF-V1

<400> SEQUENCE: 32 cag gac tcc acc tca gac ctg atc cca gcc cca cct ctg agc aag gtc       48
Gln Asp Ser Thr Ser Asp Leu Ile

```
ggc                                                                                    531
Gly <210> SEQ ID NO 33
<211> LENGTH: 534
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (1)..(534)
<223> OTHER INFORMATION: Mutein TNF-V2

<400> SEQUENCE: 33 cag gac tcc acc tca gac ctg atc cca gcc cca cct ctg agc aag gtc     48
Gln Asp Ser Thr Ser Asp Leu Ile Pro Ala Pro Pro Leu Ser Lys Val
1               5                  10                  15 cct ctg cag cag aac ttc cag gac aac caa ttc cag ggg aag tgg tat     96
Pro Leu Gln Gln Asn Phe Gln Asp Asn Gln Phe Gln Gly Lys Trp Tyr
            20                  25                  30 ctg gta ggt ctc gca ggg aat ggt att ttt aga gtt gac ttt aat ccg    144
Leu Val Gly Leu Ala Gly Asn Gly Ile Phe Arg Val Asp Phe Asn Pro
        35                  40                  45 att tct atg tat gcc acc atc tat gag ctg aaa gaa gac aag agc tac    192
Ile Ser Met Tyr Ala Thr Ile Tyr Glu Leu Lys Glu Asp Lys Ser Tyr
50                  55                  60 aat gtc acc tcc gtc gat ttt gct aat aag aag tgt gcg tac cgg atc    240
Asn Val Thr Ser Val Asp Phe Ala Asn Lys Lys Cys Ala Tyr Arg Ile
65                  70                  75                  80 agg act ttt gtt cca ggt tcc cag cca ggc gag ttc acg ctg ggc aac    288
Arg Thr Phe Val Pro Gly Ser Gln Pro Gly Glu Phe Thr Leu Gly Asn
                85                  90                  95 att aag agt tac ggt aat gtg acg agt ttc ctc gtc cga gtg gtg agc    336
Ile Lys Ser Tyr Gly Asn Val Thr Ser Phe Leu Val Arg Val Val Ser
            100                 105                 110 acc aac tac aac cag cat gct atg gtg ttc ttt aag ggt gtt gat tcg    384
Thr Asn Tyr Asn Gln His Ala Met Val Phe Phe Lys Gly Val Asp Ser
        115                 120                 125 aac aat gag cgg ttc aag att acc atc tac ggg aga acc aag gag ctg    432
Asn Asn Glu Arg Phe Lys Ile Thr Ile Tyr Gly Arg Thr Lys Glu Leu
    130                 135                 140 cct tcg gaa cta aag gag aac ttc atc cgc ttc tcc aaa tct ctg ggc    480
Pro Ser Glu Leu Lys Glu Asn Phe Ile Arg Phe Ser Lys Ser Leu Gly
145                 150                 155                 160 ctc cct gaa aac cac atc gtc ttc cct gtc cca atc gac cag tgt atc    528
Leu Pro Glu Asn His Ile Val Phe Pro Val Pro Ile Asp Gln Cys Ile
                165                 170                 175 gac ggc                                                            534
Asp Gly

<210> SEQ ID NO 34
<211> LENGTH: 178
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MISC_FEATURE
<222> LOCATION: (1)..(178)
<223> OTHER INFORMATION: Mutein N4

<400> SEQUENCE: 34
```

-continued

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Leu Val Gly Leu Ala Gly Asn Asp Ile Tyr Arg Ala Asp Ser Leu Pro
        35                  40                  45

Gly Leu Met Tyr Ala Thr Ile Tyr Glu Leu Lys Glu Asp Lys Ser Tyr
    50                  55                  60

Asn Val Thr Ser Val Val Phe Tyr Asp Lys Lys Cys Val Tyr Ser Ile
65                  70                  75                  80

Arg Thr Phe Val Pro Gly Ser Gln Pro Gly Glu Phe Thr Leu Gly Asn
                85                  90                  95

Ile Lys Ser Tyr Glu Ala Val Thr Ser Phe Leu Val Arg Val Val Ser
            100                 105                 110

Thr Asn Tyr Asn Gln His Ala Met Val Phe Phe Lys Asp Val Arg Pro
        115                 120                 125

Asn Ser Glu Glu Phe Lys Ile Thr Ile Tyr Gly Arg Thr Lys Glu Leu
    130                 135                 140

Pro Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 35
<211> LENGTH: 170
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: CHAIN
<222> LOCATION: (1)..(170)
<223> OTHER INFORMATION: fusion protein of tumor necrosis factor alpha
      and affinity tag
<220> FEATURE:
<221> NAME/KEY: MISC_FEATURE
<222> LOCATION: (1)..(13)
<223> OTHER INFORMATION: Affinity tag Arg-Gly-Ser-His(6)-Gly(3)
<220> FEATURE:
<221> NAME/KEY: MISC_FEATURE
<222> LOCATION: (14)..(170)
<223> OTHER INFORMATION: mature tumor necrosis factor alpha

<400> SEQUENCE: 35

Met Arg Gly Ser His His His His His His Gly Gly Gly Val Arg Ser
1               5                   10                  15

Ser Ser Arg Thr Pro Ser Asp Lys Pro Val Ala His Val Val Ala Asn
            20                  25                  30

Pro Gln Ala Glu Gly Gln Leu Gln Trp Leu Asn Arg Arg Ala Asn Ala
        35                  40                  45

Leu Leu Ala Asn Gly Val Glu Leu Arg Asp Asn Gln Leu Val Val Pro
    50                  55                  60

Ser Glu Gly Leu Tyr Leu Ile Tyr Ser Gln Val Leu Phe Lys Gly Gln
65                  70                  75                  80

Gly Cys Pro Ser Thr His Val Leu Leu Thr His Thr Ile Ser Arg Ile
                85                  90                  95

Ala Val Ser Tyr Gln Thr Lys Val Asn Leu Leu Ser Ala Ile Lys Ser
```

```
                100                 105                 110
Pro Cys Gln Arg Glu Thr Pro Glu Gly Ala Glu Ala Lys Pro Trp Tyr
        115                 120                 125

Glu Pro Ile Tyr Leu Gly Gly Val Phe Gln Leu Glu Lys Gly Asp Arg
130                 135                 140

Leu Ser Ala Glu Ile Asn Arg Pro Asp Tyr Leu Asp Phe Ala Glu Ser
145                 150                 155                 160

Gly Gln Val Tyr Phe Gly Ile Ile Ala Leu
                165                 170

<210> SEQ ID NO 36
<211> LENGTH: 177
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MISC_FEATURE
<222> LOCATION: (1)..(177)
<223> OTHER INFORMATION: Mutein TNF-V1

<400> SEQUENCE: 36

Gln Asp Ser Thr Ser Asp Leu Ile Pro Ala Pro Pro Le

```
                                    -continued
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Leu Val Gly Leu Ala Gly Asn Gly Ile Phe Arg Val Asp Phe Asn Pro
            35                  40                  45

Ile Ser Met Tyr Ala Thr Ile Tyr Glu Leu Lys Glu Asp Lys Ser Tyr
        50                  55                  60

Asn Val Thr Ser Val Asp Phe Ala Asn Lys Lys Cys Ala Tyr Arg Ile
65                  70                  75                  80

Arg Thr Phe Val Pro Gly Ser Gln Pro Gly Glu Phe Thr Leu Gly Asn
                85                  90                  95

Ile Lys Ser Tyr Gly Asn Val Thr Ser Phe Leu Val Arg Val Val Ser
                100                 105                 110

Thr Asn Tyr Asn Gln His Ala Met Val Phe Phe Lys Gly Val Asp Ser
            115                 120                 125

Asn Asn Glu Arg Phe Lys Ile Thr Ile Tyr Gly Arg Thr Lys Glu Leu
        130                 135                 140

Pro Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 38

His His His His His His
1               5

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 39

Arg Gly Ser His His His His His His Gly Gly Gly
1               5                   10
```

MUTEINS OF HUMAN NEUTROPHIL GELATINASE-ASSOCIATED LIPOCALIN AND RELATED PROTEINS

The present invention refers to a method for generating a mutein of human neutrophil gelatinase-associated lipocalin (hNGAL), rat $\alpha_2$-microglobulin-related protein (A2m) or mouse 24p3/uterocalin (24p3), wherein this mutein has detectable affinity to a given target and to a mutein of each of these three proteins obtainable by this method. The invention also refers to nucleic acids encoding such muteins, a pharmaceutical composition comprising a mutein of the invention as well as to various uses of the mutein of human neutrophil gelatinase-associated lipocalin, rat $\alpha_2$-microglobulin-related protein (A2m) and mouse 24p3/uterocalin (24p3).

The lipocalins (Pervaiz and Brew, FASEB J. 1 (1987), 209-214) are a family of small, often monomeric secretory proteins which have been isolated from various organisms, and whose physiological role lies in the storage or in the transport of different targets, e.g. retinol or pheromones, as well as in more complex biological functions such as taste and olfaction or prostaglandin synthesis (reviewed, e.g., by Flower, Biochem. J. 318 (1996), 1-14). The lipocalins bear relatively little mutual sequence similarity and their relationship as a protein structural family was first elucidated by X-ray structural analysis (Sawyer et al., Nature 327 (1987), 659).

Typical targets of lipocalins are liphophilic substances of low molecular weight such as retinoids, fatty acids, cholesterols, prostaglandins, biliverdins, pheromones, tastants, and odorants (Flower, Biochem. J. 318 (1996), 1-14; see also Kjeldsen, Biochimica et Biophysica Acta, 1482 (2000), 272-283). A typical target for lipocalins is vitamin A in the case of the retinol-binding protein (Rbp) as well as β-lactoglobulin (Papiz et al., Nature 324 (1986), 383-385).

Antibodies, i.e. immunoglobulins, are a classical example for proteins which selectively bind targets by way of non-covalent interaction. These proteins play a crucial role as reagents in the fields of biotechnology, medicine, bioanalytics as well as in the biological and life sciences in general. Despite manyfold needs for binding proteins in conjunction with the recognition, binding or separation of ligands/targets, almost exclusively immunoglobulins are currently used for such purposes. The application of other proteins with defined ligand-binding characteristics, for example the lectins, has remained restricted to special cases.

Recently, members of the lipocalin family have become the subject of research concerning proteins having defined ligand binding properties. The German Offenlegungsschrift DE 197 42 706 and the international patent publication WO 99/16873 disclose the class of anticalins®; polypeptides which exhibit, like antibodies, specific binding characteristics for a given ligand (cf. also Beste et al., Proc. Natl. Acad. Sci. USA, 96 (1999) 1898-1903). Anticalins® are obtainable starting from polypeptides of the lipocalin family which are mutated in those four segments that correspond to the sequence positions of the linear polypeptide sequence comprising amino acid positions 28 to 45, 58 to 69, 86 to 99 and 114 to 129 of the Bilin-binding protein (Bbp).

In addition, the German patent DE 199 26 068, WO 00/75308 as well as Schlehuber et al., J. Mol. Biol. (2000), 1105-1120, describe muteins of the Bilin-binding protein such as the muteins DigA and DigA16 which specifically bind digoxigenin.

Even though the anticalin® technology has in principle been established and has presumably yielded a promising practical application in the digoxigenin-binding Bbp muteins described above, further improvements and practical applications are desirable. In view of the various potential applications for ligand or target-binding proteins in the field of life sciences, the generation of anticalins® based on alternative lipocalin scaffolds would be desirable simply for the reason to have more options for practical realisation.

Accordingly, it is an object of the invention to provide alternative lipocalin muteins having binding affinity to a given target.

This object is solved by the method and the muteins with the features of the present independent claims.

Such a method is a method for generating a mutein of a protein selected from the group consisting of human neutrophil gelatinase-associated lipocalin (hNGAL), rat $\alpha_2$-microglobulin-related protein (A2m) and mouse 24p3/uterocalin (24p3), said mutein having detectable affinity to a given target, comprising the step (a) of subjecting the protein to mutagenesis at one or more of the sequence positions which correspond to the sequence positions 33 to 54, 66 to 83, 94 to 106, and 123 to 136 of hNGAL, resulting in one or more mutein(s) of the protein.

The method preferably comprises a further step (b) of enriching at least one resulting mutein having binding affinity for a given target from the one or more mutein(s) by selection of and/or isolating said at least one mutein. Preferably, the mutagenesis results in a plurality of muteins of the protein, i.e. two or more muteins.

This means that the present invention is based on the finding that the human neutrophil gelatinase-associated lipocalin (hNGAL) and the homologous proteins thereof from rat (A2m) and mouse (24p3) provide suitable scaffolds for the generation of proteins having binding activity to a given target of interest. hNGAL has been identified as a member of the lipocalin family and its three dimensional structure has been solved by NMR (Coles et al., J. Mol. Biol. 289 (1999), 139-157) and by X-ray crystallography (Goetz et al., Biochemistry, 39 (2000), 1935-1941), but up to now neither its physiological function nor its natural target have been unambiguously identified (Kjeldsen et al., supra). Accordingly, the present invention provides for the first time a possible practical application not only for hNGAL but also for its homologues A2m and 24p3.

The amino acid positions in the proteins A2m and 24p3 which are subjected to mutagenesis in the method according to the invention are obtained from an alignment of the amino acid sequences of hNGAL, A2m, and 24p3. In the protein A2m, which has the same number of amino acid residues (178) as hNGAL, the sequence positions which are used for the mutagenesis are identical to the positions selected in hNGAL, namely sequence positions 33 to 54, 66 to 83, 94 to 106, and 123 to 136 of hNGAL. For 24p3, the corresponding sequence positions are the sequence positions 33 to 54, 66 to 85, 96 to 108, and 125 to 138. Thus, the amino acid positions which are subjected to mutagenesis are distributed across four sequence segments corresponding to four loops in the three-dimensional structure of hNGAL, A2m, and 24p3.

The number of the segments (loops) defined above which are used for mutagenesis can vary. It is not necessary to mutate all four of these loops altogether, for example in a concerted mutagenesis, but it is also possible to subject only two or three of the loops to generate a mutein having detectable affinity to a given target.

In a preferred embodiment of the method according to the invention, the respective protein, i.e. hNGAL, A2m or 24p3 is subjected to mutagenesis at one or more of the sequence positions which correspond to the sequence positions 40 to 50, 70 to 79, 101 to 103, and 125 to 132 of hNGAL. For example, if hNGAL is selected for the generation of a mutein, hNGAL is subjected to mutagenesis at one or more of the sequence positions 40 to 50, 70 to 79, 101 to 103 and 125 to 132.

In a more preferred embodiment of the method, the respective protein is subjected to mutagenesis at one or more of the sequence positions which correspond to the sequence positions 40, 42, 44, 46, 47, 49, 50, 70, 72, 73, 77, 79, 101, 102, 103, 125, 127, 128, 130, and 132 of hNGAL.

In particularly preferred embodiments, at least 10, more preferably at least 15 of the sequence positions 40, 42, 44, 46, 47, 49, 50, 70, 72, 73, 77, 79, 101, 102, 103, 125, 127, 128, 130, and 132 of hNGAL or A2m or of the corresponding positions of 24p3 are subjected to mutagenesis. In the most preferred embodiment, all of these 20 sequence positions are randomized, wherein it is preferred to allow all 20 naturally occurring amino acids to be incorporated into the polypeptide sequences at these positions.

This means that the present invention is based on the finding that muteins of hNGAL or its homologues A2m and 24p3 having detectable affinity to a given target can be obtained by mutagenesis, preferably random mutagenesis, of a total of 20 amino acid residues, namely the sequence positions 40, 42, 44, 46, 47, 49, 50, 70, 72, 73, 77, 79, 101, 102, 103, 125, 127, 128, 130, and 132 of hNGAL. This finding is particularly surprising for several reasons.

As noted, a set of 20 amino acids in total is randomized, i.e. subjected to mutagenesis, in this preferred embodiment of the method of the invention, whereas a total of only 16 amino acids was mutated in WO 99/16873. When random NNS or NNK codon mutagenesis is used for the complete randomization of these 20 amino acid positions (i.e. each of the 20 natural amino acid is allowed at each of these selected 20 positions), $32^{20}$ possible codon combinations exist. If 16 amino acid positions are used for the randomization, $32^{16}$ possible codon combinations exist. Accordingly, increasing the number of amino acids which are subjected to random mutagenesis by 4 (from 16 to 20) results in an increase by $32~10^6$ in the combinatorial complexity. However, the number of mutants which can be physically realized in the corresponding DNA-based library cannot be deliberately increased due to experimental limitations and is usually restricted to a value of about $1·10^9$ to $1·10^{10}$ according to the state of the art (Fitzgerald, Drug Discov. Today 5 (2000), 253-258). In one example of the present invention, a combinatorial DNA-based library containing just approximately $1·10^7$ sequence variants (muteins) was used.

Considering that the small accessible section of the combinatorial sequence space is further reduced by a factor of approximately $10^6$, it is surprising that it is possible at all to isolate from a combinatorial library containing just $1·10^7$ such muteins of hNGAL (or A2m or 24p3) which a) do not only fold into soluble proteins but b) even have a new ligand/target specificity.

In this respect it should be noted that the approach taken here is in contrast to the teachings of WO 99/16873. According to this reference it should be useful to maintain the total number of mutated amino acid positions within a single experiment as low as possible such that the collection of variants obtained by mutagenesis, i.e. the library, can in its totality or, at least in a representative selection therefrom, be realized as completely as possible.

It should finally be noted that it is also surprising that the present approach is successfully used for the production of a mutein having specific binding activity towards a protein epitope (cf. Examples 5, 15, for example).

The present invention is also directed to a mutein of human neutrophil gelatinase-associated lipocalin, rat $\alpha_2$-microglobulin-related protein (A2m) or mouse 24p3/uterocalin (24p3) having detectable affinity to a given target, which is obtainable by mutagenesis of the respective protein at those sequence positions which correspond to the sequence positions 33 to 54, 66 to 83, 94 to 106, and 123 to 136 of hNGAL. Muteins are preferred which are obtainable by subjecting the respective protein to mutagenesis at the positions which correspond to the sequence positions 40 to 50, 70 to 79, 101 to 103, and 125 to 132 of hNGAL.

Preferably such a mutein carries an amino acid substitution at 5 to 10, more preferably at 8 to 12 or most preferred at 10 to 18 or at 10 to 20 of the selected 20 sequence positions.

In one preferred embodiment, the mutein has the amino acid sequence of SEQ ID NO: 12. This mutein is also referred to as TlpcA.

The muteins of the invention are able to bind the desired target with a detectable affinity, i.e. with an affinity constant of preferably at least $10^5$ $M^{-1}$. Affinities lower than this are generally no longer measurable with common methods such as ELISA and are therefore of secondary importance for practical applications. Especially preferred are muteins which bind the desired target with an affinity of at least $10^6$ $M^{-1}$, corresponding to a dissociation constant for the complex of 1 µM. The binding affinity of a mutein to the desired target can be measured by the person skilled in the art by a multitude of methods, for example by fluorescence titration, by competition ELISA or by the technique of surface plasmon resonance.

The target (ligand) which is bound by the mutein can be any chemical moiety that, for example, can also be recognized and bound by an immunoglobulin. Accordingly, the target can be a chemical compound in free or conjugated form which exhibits features of a hapten, a hormone such as steroid hormones or any biopolymer or fragment thereof, for example, a peptide, a protein or protein domain, a peptide, an oligodeoxynucleotide, a nucleic acid, oligo- and polysaccharides or another macromolecule or conjugates thereof. In a preferred embodiment of the invention, the target is a protein.

The muteins of the invention can have the natural amino acid sequence of hNGAL, A2m or 24p3 outside the mutated segments, i.e. the regions of the amino acid positions 33 to 54, 66 to 83, 94 to 106 and 123 to 136 in the case of hNGAL. On the other hand, the muteins disclosed here can also contain amino acid mutations outside the positions subjected to mutagenesis compared to the wild-type protein as long as those mutations do not interfere with the binding activity and the folding of the mutein. This includes that, for example, mutations, substitutions, deletions, insertion of amino acid residues as well as N- and/or C-terminal additions can be introduced into the natural amino acid sequence of hNGAL, A2m or 24p3.

Such modifications of the amino acid sequence of the selected protein within or without the selected binding region include directed mutagenesis of single amino acid positions, for example in order to simplify the subcloning of the mutated lipocalin gene or its parts by incorporating cleavage sites for certain restriction enzymes. For example, the mutation Glu28 to His, and/or Thr145 to Ala can be introduced into the hNGAL gene in order to simplify the cloning of the mutated gene segment via two new BstXI restriction sites at these positions. Furthermore, mutations can be introduced within or without the four peptide loops in order to improve certain characteristics of the mutein of the protein chosen as scaffold, for example its folding stability or folding efficiency or its resistance to proteases.

In a preferred embodiment, for instance, Cys87 of hNGAL is exchanged to Ser or Ala, whereby its covalent crosslinking with other proteins such as gelatinase B (which might occur in in vivo applications of a mutein) can be prevented and its monomeric structure can be stabilized. Similarly, Cys residues which may occur as a result of the mutagenesis and selection of the mutein of the invention are not always crucial for the binding of the given target and may be substituted by Ser or Ala in order to prevent covalent bond formation or oxidation of the thiol group.

In a preferred mutein of hNGAL, Cys87 is substituted and/or the mutein carries one or both of the amino acid substitution Glu(28)->His, Thr(145)->Ala compared to hNGAL. In this respect, it should be noted that the present invention is also directed to a (recombinant) hNGAL having the natural amino acid sequences in which only Cys87 has been substituted for any other suitable amino acid. This hNGAL polypeptide can be produced using the methods described here for the production of the other muteins of the inventions (see Example 4), for example by use of the vector pHNGAL7.

The method of the present invention preferably comprises (in step (b)) (i) providing as the given target a compound which is selected from the group consisting of a chemical compound in free or conjugated form which exhibits features of an immunological hapten, a peptide, a protein or another macromolecule, (ii) contacting the plurality of muteins with said target in order to allow formation of complexes between said target and muteins having binding affinity for said target, and (iii) removing muteins having no or no substantial binding affinity.

No or no substantial binding affinity means under the used conditions, no complex is formed between the target and the plurality of muteins which are contacted with the target. It is clear to the person skilled in the art that complex formation is dependent on many factors such as concentration of the binding partners, concentration of compounds acting as competitors, ion strength of the buffers etc. The selection and enrichment is generally carried out under conditions which will allow isolation and enrichment of muteins having an affinity constant of at least $10^5$ $M^{-1}$ to the target. However, the washing and elution steps can be carried out under varying stringency. For example, if muteins having an affinity constant of at least $10^6$ $M^{-1}$ are to be isolated, washing and elution can be performed under increased stringency, i.e. more stringent conditions. A selection with respect to the kinetic characteristics is also possible. The selection can, for instance, be performed under conditions which favor complex formation of the target with muteins that show a slow dissociation from the target (receptor), or in other words a low $k_{off}$ rate.

The term "plurality" as used herein means that at least two muteins that differ from each other in their amino acid sequences are present. The upper limit of muteins generated by mutagenesis is usually restricted by the experimental conditions and is generally between $10^7$ and $10^{12}$.

The term "mutagenesis" as used herein means that the experimental conditions are chosen such that the amino acid naturally occurring at a sequence position of hNGAL, A2m or 24p3 can be substituted by at least one amino acid that is not present at this specific position in the respective natural polypeptide sequence. The term "mutagenesis" also includes to (additionally) modify the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of (the respective segment) of the wild-type protein. The term "random mutagenesis" means that no predetermined single amino acid (mutation) is present at a certain sequence position but that at least two amino acids can be incorporated into a selected sequence position during mutagenesis with a certain probability.

Such experimental conditions can, for example, be achieved by incorporating codons with a degenerate base composition in the structural gene for, e.g., hNGAL at those position which are to be mutated. For example, use of the codon NNK or NNS allows incorporation of all 20 amino acids plus the amber stop codon during mutagenesis, whereas the codon VVS limits the number of possibly incorporated amino acids to 14 since it excludes the amino acids Cys, Ile, Leu, Met, Phe, Tip, Tyr, Val from being incorporated into the selected position of the polypeptide sequence; use of the codon NMS, for example, restricts the number of possible amino acids to 11 at a selected sequence position since it excludes the amino acids Arg, Cys, Gly, Ile, Leu, Met, Phe, Trp, Val from being incorporated at a selected sequence position. In a preferred embodiment of the method of the invention, a random mutagenesis is carried out, in which at least 4, preferably 6, more preferably 8 to 12 or 8 to 15 amino acids are allowed to be incorporated into a selected sequence position of hNGAL, A2m or 24p3. In a particularly preferred embodiment, at least one sequence position is subjected to complete randomization, i.e. all 20 amino acids are allowed to be incorporated at this position during mutagenesis. From the above, it is also clear that the amino acid naturally present at a certain sequence position of the respective protein such as hNGAL can also be present in the mutein after having subjecting this position to mutagenesis.

In a preferred embodiment of the method of the invention, the target is a protein. The protein can be provided either in free or conjugated form or as a fusion protein for the selection of muteins.

In a preferred embodiment of the method of the invention, a nucleic acid coding for the plurality of muteins of the respective protein selected from hNGAL, A2m and 24p3 is used. This nucleic acid results from mutagenesis and it is operably fused at the 3' end with a gene coding for the coat protein pIII of a filamentous bacteriophage of the M13-family or for a fragment of this coat protein, in order to select at least one mutein for the binding of the given target.

The nucleic acid that results from mutagenesis can be obtained by use of PCR. In a preferred embodiment of the method of the invention, the generation of the nucleic acid coding for the mutated segments of the respective protein comprises the following two steps. First, two nucleic acid fragments, each of which codes for a part of the mutated protein are generated by PCR such that these fragments are partially overlapping. These fragments are employed with two flanking primers in a second amplification step in order to obtain the nucleic acid comprising the complete mutated structural gene (see FIG. 2 and Example 1 illustrating this two step procedure). Due to the overlap the full-length PCR product will be amplified in the course of this reaction, without that the addition of any additional nucleic acid is required. The two fragments can be obtained with a pair or pairs of suitable primers in two separate amplification reactions (see also FIG. 2 and Example 1, which shows that such two fragments are generated in PCR reactions A and B).

For some applications, it is useful to employ the inventive mutein of hNGAL, A2m or 24p3 in a labeled form. Accordingly, the invention also refers to a mutein of each of the three proteins used as scaffold here which is conjugated to a label selected from the group consisting of enzyme label, radioactive label, fluorescent label, chromogenic label, luminescent label, a hapten, biotin, digoxigenin, metal complexes, metals, and colloidal gold. The mutein can also be conjugated to an organic molecule. The term "organic molecule as used in the present application preferably means an organic molecule comprising at least two carbon atoms, but not more than 7 rotatable carbon bonds having a molecular weight between 100 and 2000 Dalton, preferably 1000 Dalton and a molecule including one or two metal atoms.

In general, it is possible to label the mutein with any appropriate chemical substance or enzyme, which directly or indirectly generates in a chemical, enzymatic or physical reaction a detectable compound or a signal that can be used for detection. An example for a physical reaction is the emission of fluorescence after excitation with radiation or the emission of X-rays by a radioactive label; alkaline phosphatase, horseradish peroxidase or β-galactosidase are examples of enzyme labels which catalyse the formation of chromogenic (colored) compounds which can then be detected. In general all labels which are used for antibodies, except those which exclusively used with the sugar moiety in the Fc part of immunoglobulins can also be used for conjugation to the muteins of the present invention. These conjugates can be prepared by means of methods known to the person skilled in the art.

One option which is particularly advantageous for practical applications of the muteins disclosed here, is the use of the muteins in the form of fusion proteins. In preferred embodiments of such a fusion protein an enzyme, a protein or a protein domain, a peptide, for example a peptide such as a signal sequence and/or an affinity tag is operably fused to the amino terminus or to the carboxy terminus of the mutein.

The fusion partner can be suitable to confer new characteristics on the mutein, for example enzymatic activity or affinity for other molecules such as proteins, macromolecules or low molecular weight targets. For example, fusions with enzymes which catalyse chromogenic or fluorogenic reactions (e.g. alkaline phosphatase, horseradish peroxidase, glutathione-S-transferase) or which can serve for the liberation of cytotoxic agents are possible. Further examples of fusion partners which can be advantageous in practice are binding domains such as the albumin-binding domain of protein G, protein A, antibody fragments, oligomerizing domains, toxins or also muteins of the invention or anticalins® with different or the same target specificity. A specific example for the latter would be a fusion protein comprising an hNGAL mutein of the present invention and the digoxigenin binding mutein DigA16 disclosed in the German Patent DE 199 26 068. Affinity tags such as the Strep-Tag® or the Strep-tag® II (Schmidt et al., J. Mol. Biol. 255 (1996), 753-766) or oligohistidine tags (e.g., His6-tags) or proteins such as glutathione-S-transferase which can be used for purification by affinity chromatography and/or for detection (e.g. using the specific affinity of the Strep-tag® for streptavidin) are further examples of preferred fusion partners. Proteins with chromogenic or fluorescent properties such as the green fluorescent protein (GFP) are suitable fusion partners, too.

The term fusion protein as used herein also includes muteins of the invention, for example muteins of hNGAL, that are equipped with a signal sequence. Signal sequences at the N-terminus of a polypeptide according to the invention can be suitable to direct the polypeptide to a specific cell compartment during the biosynthesis, for example into the periplasm of $E.\ coli$ or to the lumen of the eukaryotic cell or into the medium surrounding the cell. In so doing, the signal sequence is cleaved by a signal peptidase. It is also possible to use other targeting or signaling sequences which are necessarily located at the N-terminus of the polypeptide and which allow the localization thereof in specific cell compartments. A preferred signal sequence for secretion into the periplasm of $E.\ coli$ is the OmpA-signal sequence. A large number of further signal sequences is known in the art.

The invention is also directed to a nucleic acid molecule comprising a sequence encoding a mutein according to the invention or a fusion protein thereof. In a preferred embodiment the nucleic acid molecule comprise a nucleotide sequence encoding the mutein of SEQ ID NO. 12.

Since the degeneracy of the genetic code permits substitutions of certain codons by other codons which specify the same amino acid and hence give rise to the same protein, the invention is not limited to a specific nucleic acid molecule but includes all nucleic acid molecules comprising a nucleotide sequence coding for a mutein with the amino acid sequence according to the present invention.

The nucleic acid molecule comprising a nucleotide sequence encoding a mutein of any of hNGAL, A2m or 24p3 as disclosed here can be operably linked to a regulatory sequence to allow expression of the nucleic acid molecule in a host cell (in vivo) or its transcription and translation in a cell-free system (in vitro).

A nucleic acid molecule such a DNA is regarded to be "capable of expressing of a nucleic acid molecule or a coding nucleotide sequence" or capable "to allow expression of a nucleotide sequence" if it contains nucleotide sequences which contain transcriptional and translational information and if such sequences are "operably linked" to nucleotide sequences which encode the polypeptide. An operable linkage is a linkage in which the regulatory DNA sequences and the DNA sequences sought to be expressed are connected in such a way as to permit gene expression. The precise nature of the regulatory regions and elements needed for gene expression may vary from organism to organism, but shall, in general, include a promoter region which, in prokaryotes for example, contains both the promoter regulatory sequence that can comprise a transcriptional region functional in a cell and a transcriptional terminating region functional in a cell. Elements used for transcription or translation are promoters, enhancers, leader sequences, transcription initiation sites and transcripton termination sites, polyadenylation signals, ribosomal binding sites such the Shine-Dalgarno sequence and the like. These regulatory sequences and/or the mutein of the invention can be part of a vector. Accordingly, the invention also refers to a vector comprising a nucleic acid sequence coding for a mutein of hNGAL, A2m or 24p3 as disclosed here.

In a further embodiment, the invention also relates to a method for producing of a mutein of the invention or a fusion protein thereof. In this method the mutein or the fusion protein is produced starting from the nucleic acid encoding the mutein by means of genetic engineering methods in a bacterial or eukaryotic host organism and is isolated from this host organism or its culture. For this purpose a suitable host cell is usually first transformed with a vector comprising a nucleic acid molecule encoding, for instance, a NGAL mutein of the invention. The host cell, which can be any prokaryotic or eukaryotic host cell is then cultured under conditions which allow the biosynthesis of the polypeptide. The polypeptide is then usually recovered either from the cell or from the cultivation medium. Since each of human neutrophil gelatinase-associated lipocalin, A2m and 24p3 contain one structural disulfide bond it is preferred to direct the polypeptide into a cell compartment having an oxidizing thiol/disulfide redox milieu by use of a suitable signal sequence. Such an oxidizing milieu is present in the periplasm of bacteria such as E. coli or in the lumen of the endoplasm reticulum of a eukaryotic cell and usually favors the correct formation of the disulfide bonds. It is, however, also possible to produce a polypeptide of the invention in the cytosol of a host cell, preferably E. coli. In this case the polypeptide can, for instance, be produced in form of inclusion bodies, followed by renaturation in: vitro. A further option is the use of specifically mutated strains which have an oxidizing milieu in the cytosol and thus allow allow production of the native protein in the cytosol.

As evident from the above disclosure, the mutein of the present invention or a fusion or a conjugate thereof can be employed in many applications. In general, a mutein disclosed here can be used in all applications antibodies are used in, except those with specifically rely on the glycosylation of the Fc part.

A preferred use of the mutein is the detection of a target by a mutein of the invention or a fusion protein thereof, which comprises the steps of contacting the mutein with a sample suspected of containing the given target under suitable conditions, thereby allowing formation of a complex between the mutein and the given target, and determining the complexed mutein by a suitable signal. This signal can be caused by a label such as a fluorescent or chromogenic label as explained above. This signal can also be caused by the change of a physical properties which is caused by the binding, i.e. complex formation itself. An example of such a properties is plasmon surface resonance the value of which is changed during binding of binding partners from which one is immobilized on a surface such as a gold foil.

As noted above, a mutein disclosed here and its derivatives can be employed in many areas similar to antibodies or their fragments. A mutein is preferably used for binding to a solid phase, so that the target of the mutein or a conjugate or a fusion protein of this target can be immobilized or separated. Further preferred is the use of the mutein for labeling with an enzyme, an antibody or a radioactive substance or another group with a biochemical activity or with defined binding characteristics, so that the target of the mutein or a conjugate or a fusion protein of this target can be detected or brought in contact with it. Muteins of the invention can serve for example in the detection of chemical structures by means of established bioanalytic methods such as ELISA or Western Blot, in microscopy or immunosensorics. Here, the detection signal can either be generated directly by use of a suitable mutein conjugate or fusion protein or indirectly with detection of the bound mutein by means of an antibody directed against it or for example by using an affinity tag.

Numerous possible applications for a mutein of hNGAL, A2m or 24p3 also exist in medicine. In addition to its use in diagnostics, a mutant polypeptide of the invention which binds for example tissue- or tumor-specific cellular surface molecules can be prepared. Such a mutein can, for example, be employed in conjugated form or as a fusion protein for "tumor imaging" or directly for cancer therapy.

Another related and preferred use of a mutein described here is the target validation, i.e. the examination whether a polypeptide that is assumed to be involved in the development of a disease or disorder is indeed somehow causative of the disease or disorder. This use for validation of the protein as a pharmacological drug target takes advantage of the ability of a mutein of the present invention to specifically recognize a surface area of a protein in its native conformation, i.e. the ability of a mutein disclosed here to bind to a native epitope. In this respect, it is to be noted that this ability to bind to a native epitope has been reported only for a limited number of recombinant antibodies, irrespective whether they have been produced by the classical immunization protocol of Köhler and Milstein (Nature 256 (1975), 495-497) or by combinatorial techniques such as phage display. The use of a mutein for validation of a drug target does not only comprises the detection of a target which is a protein, but also detection of a target which is a protein domain, a peptide, a nucleic acid molecule, an organic molecule or a metal complex.

In a further aspect, the invention refers to a pharmaceutical composition comprising a mutein of human neutrophil gelatinase-associated lipocalin, rat $\alpha_2$-microglobulin-related protein (A2m) or mouse 24p3/uterocalin (24p3) according to the invention or a fusion protein thereof and a pharmaceutically acceptable carrier.

A mutein, for example a hNGAL mutein, of pharmaceutical interest can, for example, be a mutein having binding to tumour-specific cellular surfaces. It can also be a mutein which binds a specific drug and which serves as a "sustained release-release" form for this drug or a long-term storage of the drug in the body of a patient. Such a mutein can be administered by any therapeutically effective route for a proteinaceous pharmaceutical, e.g. parenterally, intranasally, rectally, buccally, or by inhalation via sprays or aerosols into the respiratory tract. Administration can occur in dosage unit formulations containing conventional non-toxic pharmaceutically acceptable carriers, adjuvants and vehicles as desired. The term "parenteral" embraces delivery modes such as subcutaneous, intravenous, intramuscular, instrasternal, intra-arterial injection and infusion techniques. Due to the low molecular weight, inhalation is one of the preferred ways of administering a pharmaceutically useful mutein of the invention.

Accordingly, the mutein of the present invention can be formulated into compositions using both known pharmaceutically acceptable ingredients and methods of preparation. See, e.g., Remington et al., Pharmaceutical Sciences, 15th Ed., Mack Pub., Easton (1975).

For inhalation the muteins of the invention can be first placed into a particulate dispersed form. This can be accomplished by preparing an aqueous aerosol or solid particles which contain the respective polypeptide. Ordinarily, an aqueous aerosol is made by formulating an aqueous solution or suspension of the desired polypeptide together with conventional pharmaceutically acceptable carriers and stabilizers. The carriers and stabilizers will vary depending upon the requirements for each polypeptide, they can include nonionic surfactants (such as Tweens, Pluronics or polyethylene glycol), innocuous proteins like serum albumin, sorbitan esters, oleic acid,ecithin, amino acids such as glycine, buffers, salts, sugars or sugar alcohols. The formulations also can include bronchodilating agents. The formulations will be sterile. Aerosols generally will be prepared from isotonic solutions. The particles optionally include normal lung surfactant proteins. Exemplary formulations for inhalation of proteins are disclosed in U.S. Pat. No. 6,099, 517, for example. Administration of dry powder compositions for inhalation of a mutein of the invention is also possible. Suitable dry-powder formulations are described in U.S. Pat. No. 6,123,936, for example.

One option for preparing pharmaceutical compositions suitable for inhalation includes to form aerosols of particles in an aqueous or non-aqueous, e.g. fluorocarbon propellant, suspension. Such particles include, for example, intramolecular aggregates of the polypeptides or liposomal or microcapsular-entrapped polypeptides. The aerosols should be free of lung irritants, i.e. substances which cause acute bronchoconstriction, coughing, pulmonary edema or tissue destruction. However, nonirritating absorption enhancing agents are suitable for use herein.

Suitable compositions for parenteral administration comprise pharmaceutically acceptable sterile aqueous or non aqueous solutions, dispersions, suspensions or emulsions, as well as sterile powders for reconstitution into sterile injectable solutions or into dispersions, immediately prior to use. Representative examples of suitable aqueous and non-aqueous carriers, diluents, solvents or vehicles include water, ethanol, polyols, e.g.,—glycerol, propylene glycol, polyethylene glycol—and suitable mixtures thereof, vegetable oils, e.g., olive oil, and injectable organic esters such as ethyl oleate. Fluidity may be maintained by various means including the use of coating materials such as lecithin, the maintenance of required particle size (in the case of dispersions) and surfactants.

The compositions may also contain adjuvants such as preservatives, wetting agents, emulsifying agents, dispersing agents, antibacterial and antifungal agents such as paraben, chlorobutanol, phenol and sorbic acid, isotonic agents such as sugars, sodium chloride, or agents which delay absorption such as aluminium monostearate and gelatin. The mutein may be incorporated into slow or sustained release or targeted delivery systems such as polymer matrices,ipo-somes and microspheres.

Injectable formulations can be sterilized by numerous means, including filtration through a bacteria-retaining filter, or by incorporating sterilizing agents in the form of sterile solid compositions which can be dissolved or dispersed in sterile water or other sterile injectable medium just prior to use.

The coding sequence for the each of the proteins used as scaffold here can serve as a starting point for mutagenesis of the peptide segments selected in the present invention. The coding sequence of hNGAL has been described by Bundgard et al., Biochem. Biophys. Res. Commun. 202 (1994), 1468-1475. The coding sequence of A2m and 24p3, respectively has been published by Chan et al., Nucleic Acid Res. 16 (1988) 11638; and Stoesz et al., Oncogene 11 (1995), 2233-2241, for example. For the mutagenesis of the amino acids in the four peptide loops, the person skilled in the art has at his disposal the various known methods for site-directed mutagenesis or for mutagenesis by means of the polymerase chain reaction. The mutagenesis method can, for example, be characterized in that mixtures of synthetic oligodeoxynucleotides, which bear a degenerate base composition at the desired positions, can be used for introduction of the mutations. The use of nucleotide building blocks with reduced base pair specificity, as for example inosine, is also an option for the introduction of mutations into the chosen sequence segment or amino acid positions. The procedure for mutagenesis of target-binding sites is simplified as compared to antibodies, since for hNGAL only four instead of six sequence segments—corresponding to the four above cited peptide loops—have to be manipulated for this purpose. A further possibility is the so-called triplet-mutagenesis. This method uses mixtures of different nucleotide triplets each of which codes for one amino acid for the incorporation into the coding sequence.

One of the various applicable methods for the introduction of mutations in the region of the four selected peptide loops of the scaffold proteins used here (i.e. in the case of hNGAL at sequence positions 33 to 54, 66 to 83, 94 to 106 and 123 to 136) is based on the use of four oligodeoxynucleotides, each of which is partially derived from one of the four corresponding sequence segments to be mutated. In the production of these oligodeoxynucleotides, the person skilled in the art can employ mixtures of nucleic acid building blocks for the synthesis of those nucleotide triplets which correspond to the amino acid positions to be mutated, so that codons or anticodons randomly arise for all amino acids or, according to the genetic code and to the composition of this mixture, for a selection of the desired amino acids at this position.

For example, the first oligodeoxynucleotide corresponds in its sequence—apart from the mutated positions—at least partially to the coding strand for the peptide loop, which is located in the polypeptide sequence of hNGAL at the most N-terminal position. Accordingly, the second oligodeoxynucleotide corresponds at least partially to the non-coding strand for the second sequence segment following in the polypeptide sequence. The third oligodeoxynucleotide corresponds in turn at least partially to the coding strand for the corresponding third sequence segment. Finally, the fourth oligodeoxynucleotide corresponds at least partially to the non-coding strand for the fourth sequence segment. A polymerase chain reaction can be performed with the respective first and second oligodeoxynucleotide and separately if needed, with the respective third and fourth oligodeoxynucleotide by using the nucleic acid which encodes the scaffold protein and/or its complementary strand as a template.

The amplification products of both of these reactions can be combined by various known methods into a nucleic acid which comprises the sequence from the first to the fourth sequence segments and which bears the mutations at the selected amino acid positions. To this end, both of the products can for example be subjected to a new polymerase chain reaction using flanking oligodeoxynucleotides as primers as well as one or more mediator nucleic acid molecules which contribute the sequence between the second and the third sequence segment. This procedure is schematically reproduced in FIG. 1. In the choice of the number of the oligodeoxynucleotides used for the mutagenesis and their arrangement within the gene sequence of protein used, the person skilled in the art has furthermore numerous alternatives at his disposal.

The nucleic acid molecules which code for the sequence region encompassing the four peptide loops of the protein used and which contain mutations at the selected positions defined above can be connected by ligation with the missing 5'- and 3'-sequences of a nucleic acid coding for hNGAL, for example, and/or the vector, and can be cloned in a known host organism. A multitude of procedures are at one's disposal for the ligation and the cloning. For example, in the course of an amplification, synthetic nucleic acid molecules with restriction endonuclease recognition sequences, which are also present at the corresponding positions in the nucleic acid sequence for hNGAL, can be attached at both ends of the nucleic acid to be cloned so that a ligation is made possible following hydrolysis with the corresponding restriction enzyme. The missing 5'- and 3'-sequences of a nucleic acid coding for the respective lipocalin used in the present invention can also be attached to the nucleic acid molecule comprising the mutated sequence positions via PCR.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains (Low et al., J. Mol. Biol. 260 (1996), 359-368). Such methods can also be used for the further optimization of the target affinity or target specificity of a mutein which has already been produced. Mutations which possibly occur outside the segments of the sequence positions 33 to 54, 66 to 83, 94 to 106 and 123 to 136 of hNGAL, for instance, can often be tolerated or can even prove advantageous, for example if they contribute to an improved folding efficiency or folding stability of the mutein.

After having brought the coding nucleic acid sequences that were subjected to mutagenesis to expression, the clones carrying the genetic information for the plurality of respective muteins which bind a given target can be selected from the library obtained. Known expression strategies and selection strategies can be employed for the selection of these clones. Methods of this kind have been described in the context of the production or the engineering of recombinant antibody fragments, such as the "phage display" technique (Hoess, Curr. Opin. Struct. Biol. 3 (1993), 572-579; Wells and Lowman, Curr. Opin. Struct. Biol. 2 (1992), 597-604) or "colony screening" methods (Skerra et al., Anal. Biochem. 196 (1991), 151-155) or "ribosome display" (Roberts, Curr. Opin. Chem. Biol. 3 (1999) 268-273).

An embodiment of the "phage display" technique (Hoess, supra; Wells and Lowman, supra; Kay et al., Phage Display of Peptides and Proteins—A Laboratory Manual (1996), Academic Press) is given here as an example of a selection method according to the invention for muteins with the desired binding characteristics. The various other possible embodiments of the "phage display" technique are hereby incorporated into the disclosure by reference. For the exemplary selection method, phasmids are produced which effect the expression of the mutated hNGAL structural gene as a fusion protein with a signal sequence at the N-terminus, preferably the OmpA-signal sequence, and with the coat protein pIII of the phage M13 (Model and Russel, in "The Bacteriophages", Vol. 2 (1988), Plenum Press, New York, 375-456) or fragments of this coat protein, which are incorporated into the phage coat, at the C-terminus. The C-terminal fragment ΔpIII of the phage coat protein, which contains only amino acids 217 to 406 of the natural coat protein pIII, is preferably used to produce the fusion proteins. Especially preferred is a C-terminal fragment from pIII in which the cysteine residue at position 201 is missing or is replaced by another amino acid.

The fusion protein can contain other components such as for example an affinity tag or an epitope sequence for an antibody which allows the immobilization or the later purification of the fusion protein or its parts. Furthermore, a stop codon can be located between the region coding for hNGAL or its mutein and the gene segment for the coat protein or its fragment, which stop codon, preferably an amber stop codon, is at least partially translated into an amino acid during translation in a suitable suppressor strain.

Phasmids here denote plasmids which carry the intergenetic region of a filamentous bacterial phage, such as for example M13 or fl (Beck and Zink, Gene 16 (1981), 35-58) or a functional part thereof, so that during superinfection of the bacterial cells with a helper phage, for example M13K07, VCS-M13 or R408, one strand of the circular phasmid DNA is packaged with coat proteins and is exported into the medium as so-called phagemid. On the one hand this phagemid has the hNGAL mutein encoded by the respective phasmid built into its surface as a fusion with the coat protein pIII or its fragment, wherein the signal sequence of the fusion protein is normally cleaved off. On the other hand it carries one or more copies of the native coat protein pIII from the helper phage and is thus capable of infecting a recipient generally a bacterial strain carrying an F- or F'-plasmid. In this way a physical coupling is ensured between the packaged nucleic acid carrying the genetic information for the respective hNGAL mutein, and the encoded protein which is at least partially presented in functional form on the surface of the phagemid.

The vector phNGAL5 (FIG. 1) can for example be used in the construction of the phasmid with the sequences coding for the hNGAL muteins. The nucleic acid coding for the peptide loops can, for example, be inserted into the vector phNGAL5 via both of the BstXI-restriction sites. Recombinant phasmids are incorporated by transformation into the E. coli strain, for example XL1-blue (Bullock et al., BioTechniques 5 (1987), 376-379) or TG1. In this way, clones are made which can produce many different hNGAL muteins as fusion proteins.

This library, i.e. the collection of the clones obtained, is subsequently superinfected in liquid culture according to known methods with an M13-helper phage. After this infection the incubation temperature of the culture can be reduced for production of the phagemids. Preferred incubation temperatures are those in which the optimal folding of the hNGAL mutein as a component of the fusion protein with the phage coat protein or its fragment is expected. During or after the infection phase the expression of the gene for the fusion protein with the hNGAL mutein can be induced in the bacterial cells, for example by addition of anhydrotetracycline. The induction conditions are chosen such that a substantial fraction of the phagemids produced presents at least one hNGAL mutein. The phagemids are isolated after a culture incubation phase of for example 6 to 8 hours. Various methods are known for isolation of the phagemids, such as for example precipitation with polyethylene glycol.

The isolated phasmids can be subjected to a selection by incubation with the desired target, wherein the target is present in a form allowing at least a temporary immobilization of those phagemids carrying muteins with the desired binding activity as fusion proteins in their coat. Among the various embodiments known to the person skilled in the art, the target can for example be conjugated with a carrier protein such as serum albumin and be bound via this carrier protein to a protein binding surface, for example polystyrene. Microtiter plates suitable for ELISA techniques or so-called "immuno-sticks" can preferably be used for this immobilization of the target. Alternatively, conjugates of the target can also be implemented with other binding groups such as for example biotin. The target can then be immobilized on surfaces which selectively bind this group, such as for example microtiter plates or paramagnetic particles coated with streptavidin or avidin.

Residual protein- or phagemid-binding sites present on the surfaces which are charged with targets can be saturated with blocking solutions known for ELISA-methods. The phagemids are for example subsequently brought in contact in a physiological buffer with the target immobilized on the surface. Unbound phagemids are removed by multiple washings. The phagemid particles remaining on the surface are subsequently eluted. For elution, the free target can be added as a solution. But the phagemids can also be eluted by addition of proteases or, for example, in the presence of acids, bases, detergents or chaotropic salts, or under moderately denaturing conditions. A preferred method is the elution using buffers of pH 2.2, wherein the eluate is subsequently neutralized.

Afterwards, E. coli cells are infected with the eluted phagemids using generally known methods. The nucleic acids can also be extracted from the eluted phagemids and be incorporated into the cells in another manner. Starting from the E. coli clones obtained in this way, phagemids are in turn generated by superinfection with M13-helper phages according to the method described above and the phagemids propagated in this way are once again subjected to a selection on the surface with the immobilized target. Multiple selection cycles are often necessary in order to obtain the phagemids with the muteins of the invention in enriched form. The number of selection cycles is preferably chosen such that in the subsequent functional analysis at least 0.1% of the clones studied produce muteins with detectable affinity for the given target. Depending on the size, i.e. the complexity of the library employed, 2 to 8 cycles are typically required to this end.

For the functional analysis of the selected muteins, an E. coli strain is infected with the phagemids obtained from the selection cycles and the corresponding double stranded phasmid DNA is isolated. Starting from this phasmid DNA or also from the single-stranded DNA extracted from the phagemids, the nucleic acid sequences of the selected muteins of the invention can be determined by the methods common for this purpose and the amino acid sequence can be derived therefrom. The mutated region or the sequence of the entire hNGAL mutein can be subcloned in another expression vector and expressed in a suitable host organism. phNGAL7 can for example be used as the expression vector (cf. FIG. 3) and the expression with phNGAL7 derivatives can be performed in E. coli strains, for example E. coli-TG1. The muteins of hNGAL produced by genetic engineering can be purified by various proteinchemical methods. The hNGAL muteins produced for example with phNGAL7 carry the affinity peptide Strep-Tag II (Schmidt et al., supra) at their C-terminus and can therefore preferably be purified by streptavidin affinity chromatography.

The selection can also be carried out by means of other methods. Many corresponding embodiments are known to the person skilled in the art or are described in the literature. A combination of methods can also be applied. For example, clones selected or at least enriched by "phage display" can additionally be subjected to a "colony screening". This procedure has the advantage that individual clones can directly be isolated with respect to the production of a hNGAL mutein with detectable binding affinity for a target.

In addition to the use of E. coli as host organism in the "phage display" technique or the "colony screening" method, other bacterial strains, yeast or also insect cells or mammalian cells can for example be used for this purpose. In addition to the selection of an hNGAL mutein from a primary library produced starting from a coding nucleic acid sequence for a mutein, comparable methods can also be applied in order to optimize a mutein with respect to the affinity or specificity for the desired target by repeated, optionally limited mutagenesis of its coding nucleic acid sequence.

It is surprising that by use of the method of the invention hNGAL muteins can be isolated which show detectable affinity to a given target (cf. Examples 4, 5).

It is additionally possible to subject the muteins produced to a further, optionally partial random mutagenesis in order to select variants of even higher affinity from the new library thus obtained. A corresponding procedures have already been described for the case of digoxigenin binding muteins of the bilin-binding protein for the purpose of an "affinity maturation" (DE 199 26 068, WO 00/75308; Schlehuber et al., supra) and can also be applied to a mutein disclosed here in a corresponding manner by the person skilled in the art.

The invention is further illustrated by the following non-limiting examples and the attached drawings in which:

FIG. 1 schematically depicts the phasmid vector phNGAL5;

FIG. 2 schematically illustrates the production of the library of lipocalin muteins at the nucleic acid level;

FIG. 3 schematically depicts the expression vector phNGAL7;

FIG. 4 schematically depicts the expression vector pTLpc3;

FIG. 5 depicts the binding of the mutein TlpcA to Tear lipocalin and a corresponding control experiment with hNGAL using ELISA;

FIG. 6 schematically depicts the phasmid vector phNGAL12;

FIG. 7 schematically depicts the expression vector phNGAL15;

Figure 11:
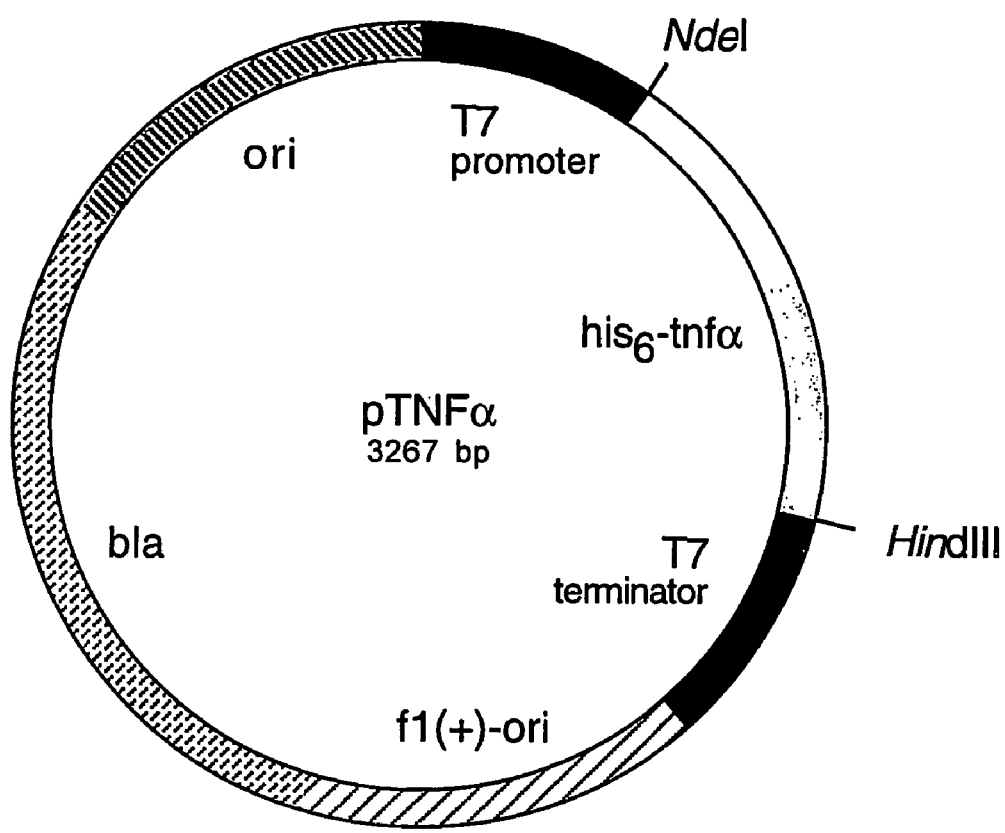
Figure 12:
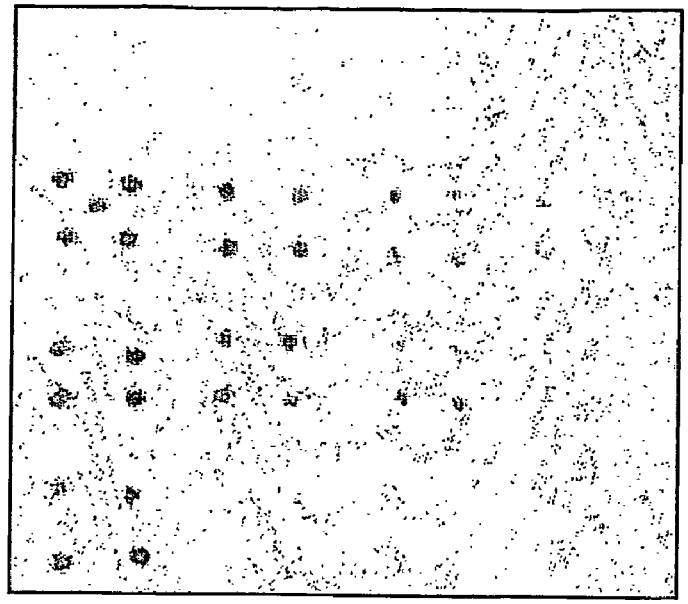

FIG. 11 schematically depicts the expression vector pTNFα;

FIG. 12 depicts the binding of TNFα to the hNGAL muteins TNF-V1 and TNF-V2—together with hNGAL as a control—in a colony spot assay.

Figure 1:
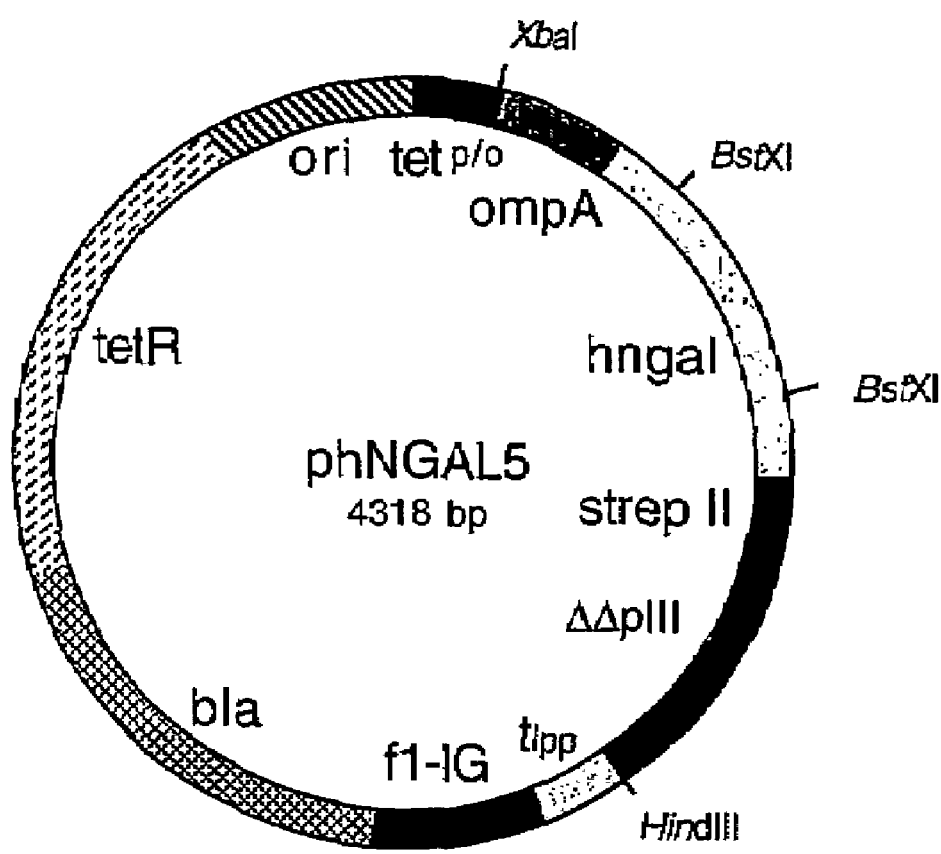

FIG. 1 shows a schematic drawing of phNGAL5. This vector codes for a fusion protein of the OmpA signal sequence, a modified hNGAL with the three amino acid substitutions Gln28 to His, Leu137 to Ile as well as Thr145 to Ala, the Strep-Tag II affinity tag and a shortened form of the M13 coat protein pIII, comprising the amino acids 217 to 406 (pH). The entire structural gene is subject to the transcriptional control of the tetracycline promoter/operator ($tet^{p/o}$) and ends at the lipoprotein transcription terminator ($t_{lpp}$). Further elements of the vector are the origin of replication (ori), the intergenic region of the filamentous bacterophage fl (fl-IG), the ampicillin resistance gene (bla) coding for β-lactamase and the tetracycline repressor gene (tetR). An amber stop codon, which is partially translated into Gln in SupE amber suppressor host strain, is located between the coding region for hNGAL with the OmpA signal sequence and the Strep-Tag II as well as the coding region for the truncated phage coat protein pIII. Both the two BstXI-restriction sites used for the cloning of the mutated gene cassette and the restriction sites flanking the structural gene are labelled. A relevant segment from the nucleic acid sequence of phNGAL5 is reproduced together with the encoded amino acid sequence in the sequence listing as SEQ ID NO:7. The segment begins with an XbaI restriction site and ends with the HindIII restriction site. The vector elements outside this region are identical with those of the vector pASK75, the complete nucleotide sequence of which is given in the German patent publication DE 44 17 598 A1.

Figure 2:
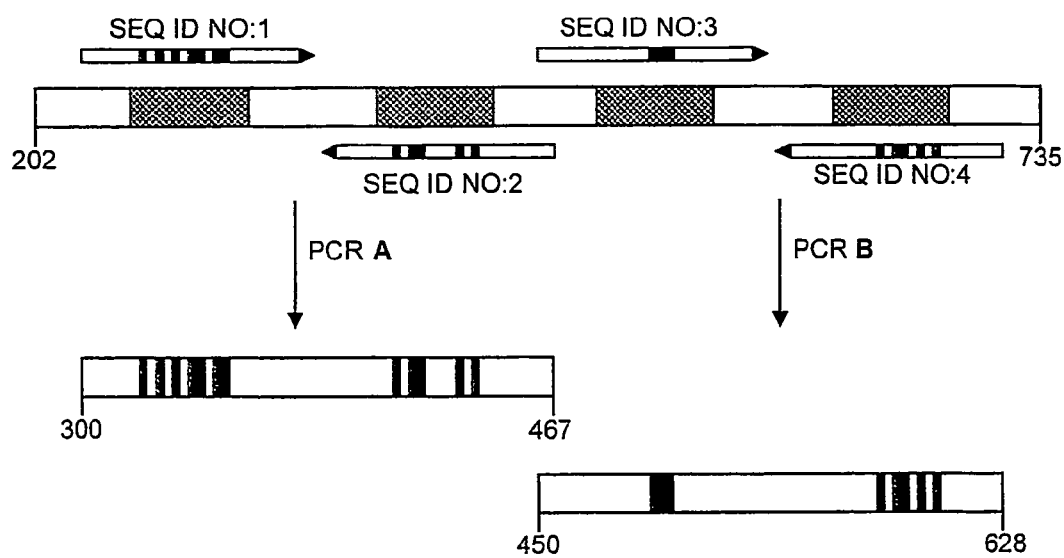
Figure 2:
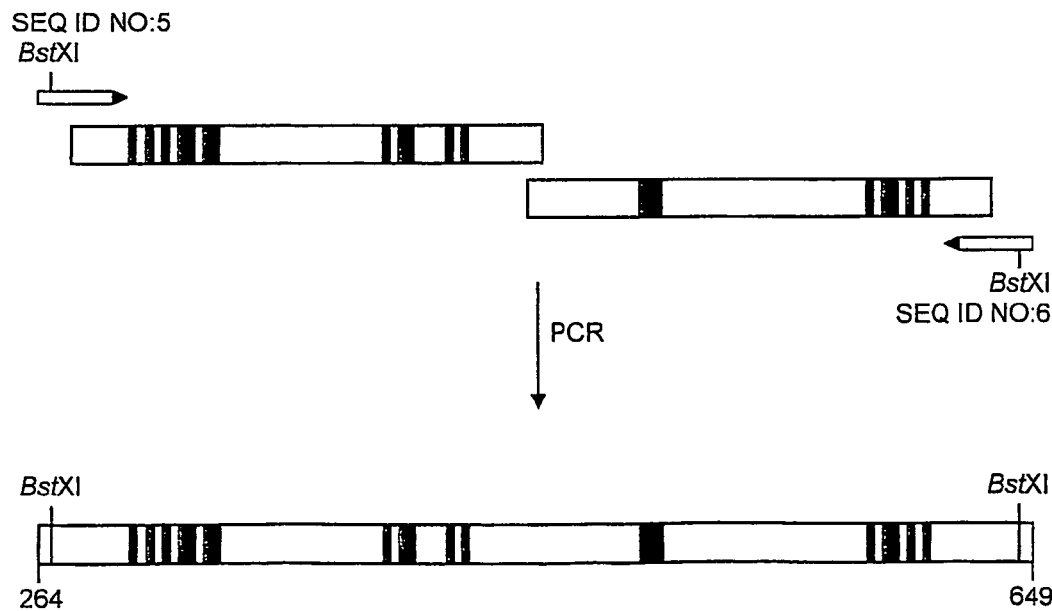

FIG. 2 schematically shows a strategy for the concerted mutagenesis of 20 selected amino acid positions in the hNGAL by repeated application of the polymerase chain reaction (PCR). For each of the four peptide loops in which the amino acids are to be mutated, an oligodeoxynucleotide was synthesized, (SEQ ID NO:1, SEQ ID NO:2, SEQ ID NO:3 and SEQ ID NO:4), wherein the respective mixtures of the nucleotides given in the sequence listing were employed at the mutation sites. Due to the composition chosen, from the altogether three possible stop codons only the amber stop codon, TAG, was allowed at the mutated codons, which is translated as glutamine in the *E. coli* supE-strains XL1-blue (Bullock et al., BioTechniques 5 (1987), 376-378) or TG1 (Sambrook et al., Molecular Cloning. A Laboratory Manual (1989), Cold Spring Harbor Press) that were used for gene expression. For certain applications, for example for gene expression in other bacterial strains or organisms, such a nonsense codon, when it arises in the structural gene for a selected hNGAL mutein, can be substituted by a glutamine-encoding codon by the person skilled in the art, for example via site-directed mutagenesis. A nucleic acid fragment with 168 base pairs was amplified (1. PCR, PCR A)) with the primers SEQ ID NO:1 and SEQ ID NO:2 using the phNGAL3-plasmid-DNA (SEQ ID NO:8) containing the cloned hNGAL cDNA as template. In another PCR, a nucleic acid fragment with 179 base pairs was amplified (1. PCR, PCR B) with the primers SEQ ID NO:3 and SEQ ID NO:4, also using phNGAL3 as template. phNGAL3 differs from phNGAL5 only by two missing BstXI restriction sites at positions 283 and 630 and one further BstXI restriction site at position 675, showing the hNGAL wildtype sequences there. The mixture of both PCR products, which were partially overlapping, served as template in another amplification (2. PCR) with the two flanking PCR primers SEQ ID NO:5 and SEQ ID NO:6, wherein a gene fragment of 386 base pairs was obtained. This fragment contained the mixture of all 20 mutated codons and was subsequently cloned using the two BstX restriction sites on the vector phNGAL5. The use of these two restriction sites, the special arrangement of which led to two non-compatible overhanging DNA ends during the restriction digest, enabled a particularly efficient ligation. The substitution of the amino acids Gln28 to His and Thr145 to Ala with respect to the original sequence as well as a silent mutation in the codon for Ser156 were previously accomplished during the construction of phNGAL5 in order to introduce both of the BstXI restriction sites into the hNGAL structural gene.

Figure 3:
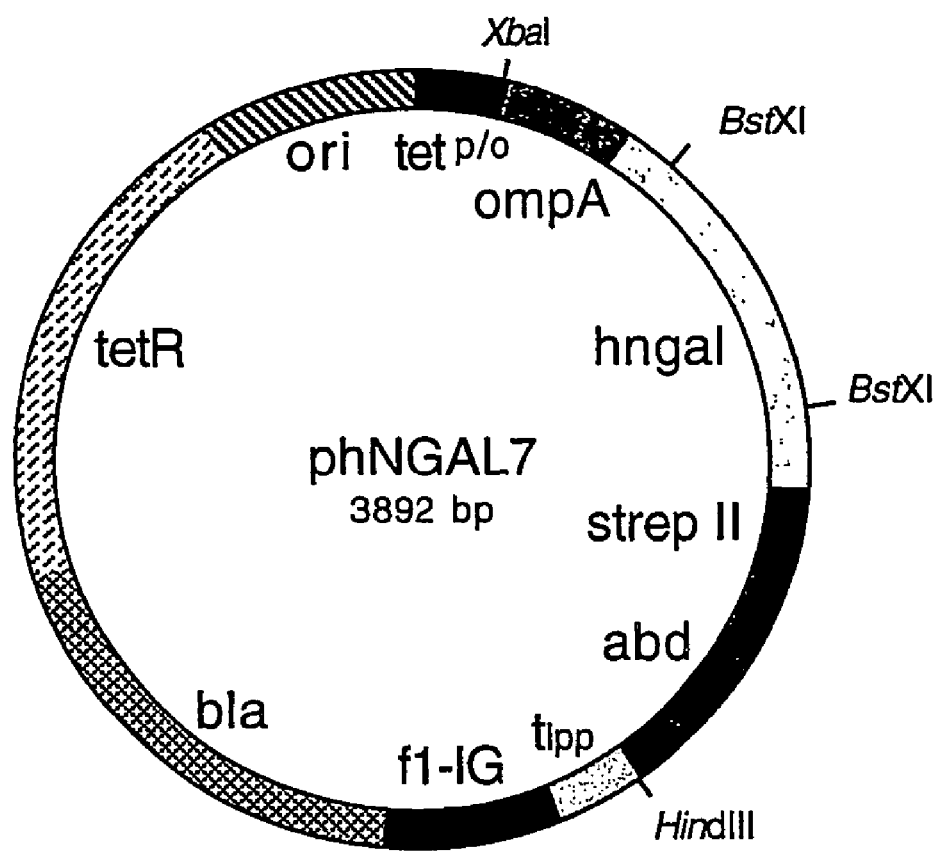

FIG. 3 shows a drawing of phNGAL7. phNGAL7 codes for a fusion protein made of the OmpA-signal sequence, a modified hNGAL according to FIG. 1, the Strep-Tags II affinity tag, and an albumin-binding domain (abd) of protein G from *Streptococcus* (Kraulis et al., FEBS Lett. 378 (1996), 190-194). All further genetic elements are identical with phNGAL5. A relevant segment from the nucleic acid sequence of phNGAL7 is reproduced together with the encoded amino acid sequence in the sequence listing as SEQ ID NO:9. The segment begins with the XbaI-restriction site and ends with the HindIII restriction site. The vector elements outside this region are identical with the vector pASK75, the complete nucleotide sequence of which is given in the German patent publication DE 44 17 598 A1.

Figure 4:
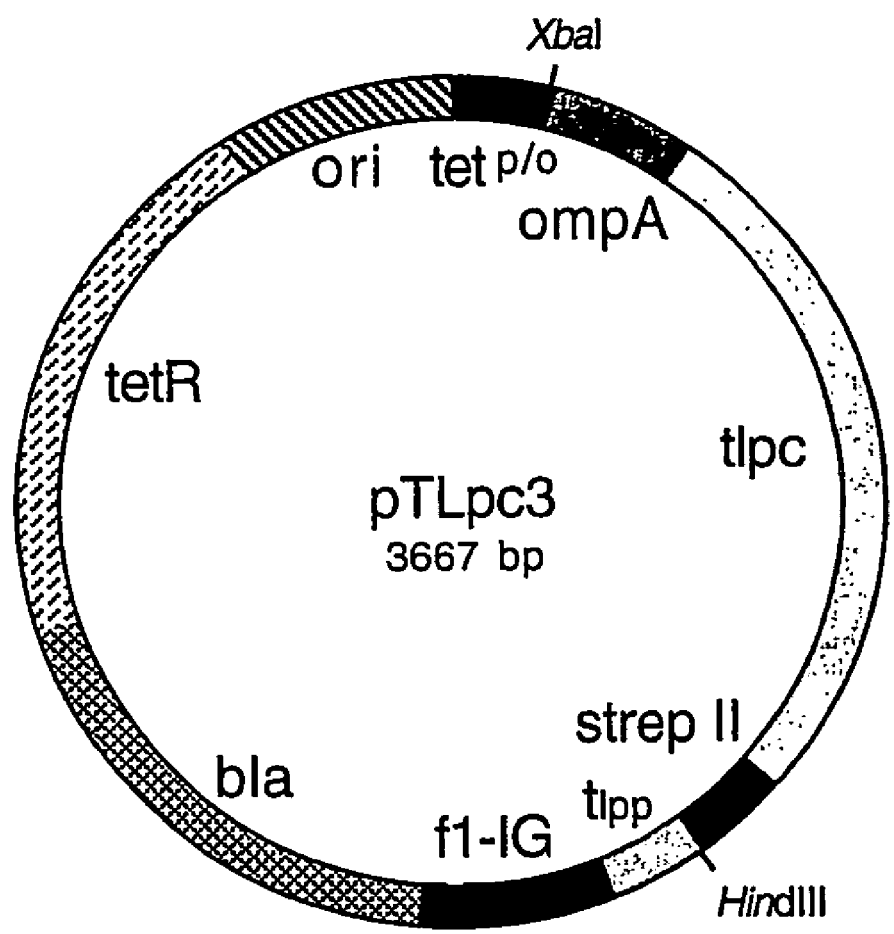

FIG. 4 shows a drawing of pTLpc3. pTLpc3 codes for a fusion protein made of the OmpA-signal sequence, a modified human Tear Lipocalin with the amino acid substitution Cys97 to Ser and, the Strep-Tag® II affinity tag. All further genetic elements are identical with phNGAL5. A relevant segment from the nucleic acid sequence of pTLpc3 is reproduced together with the encoded amino acid sequence in the sequence listing as SEQ ID NO:9. The segment begins with the XbaI-restriction site and ends with the HindIII restriction site. The vector elements outside this region are identical with the vector pASK75, the complete nucleotide sequence of which is given in the German patent publication DE 44 17 598 A1.

Figure 5:
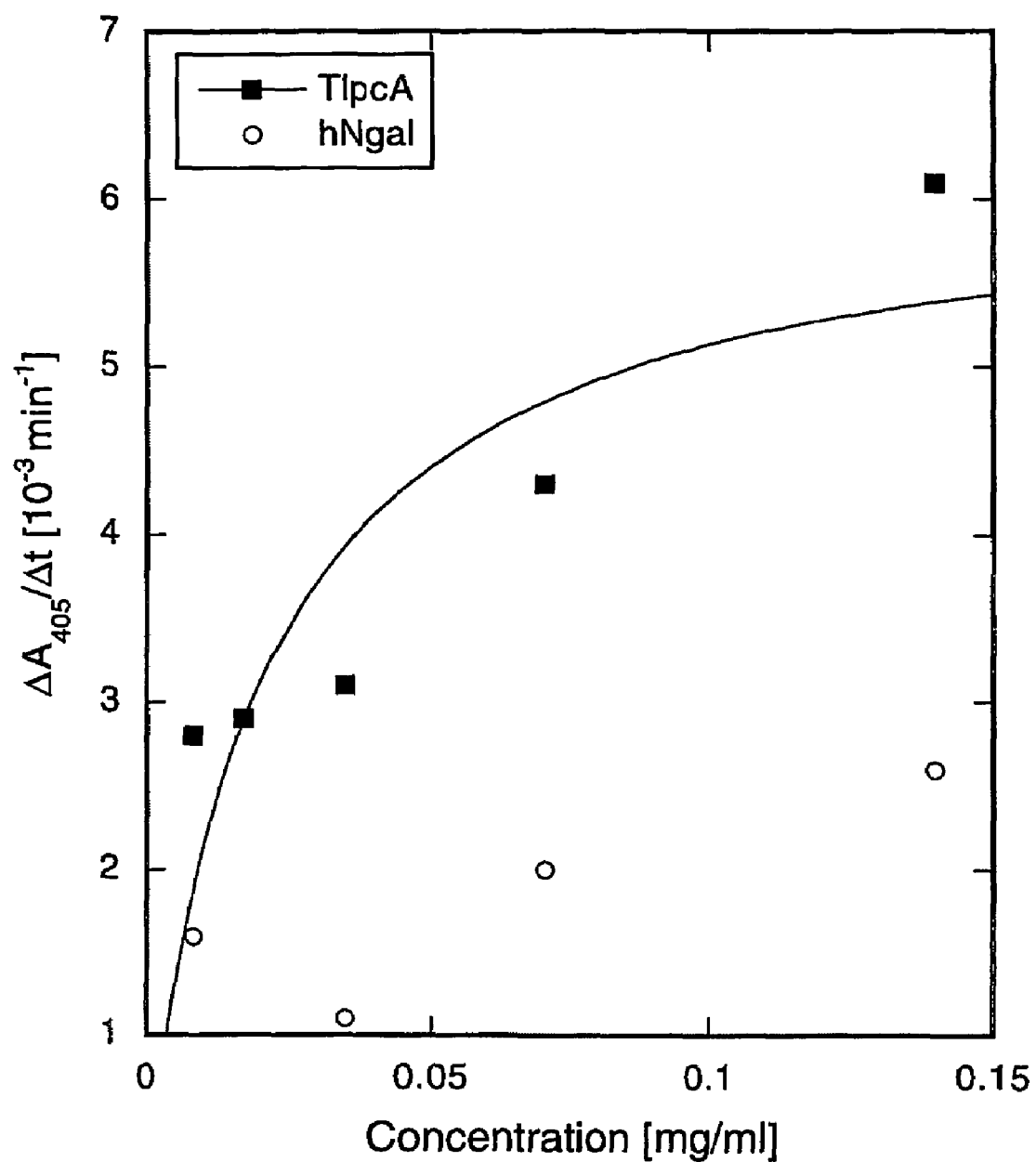

FIG. 5 shows a graphical representation of the data from Example 5, in which binding measurements with the hNGAL mutein TlpcA were performed by Enzyme-linked Immunosorbent Assay (ELISA). Binding of TlpcA and Tear lipocalin (squares) was compared to the interaction of hNGAL and Tear lipocalin (open circles). TlpcA binds Tear lipocalin in a concentration-dependent manner. hNGAL does not show a significant binding signal.

Figure 6:
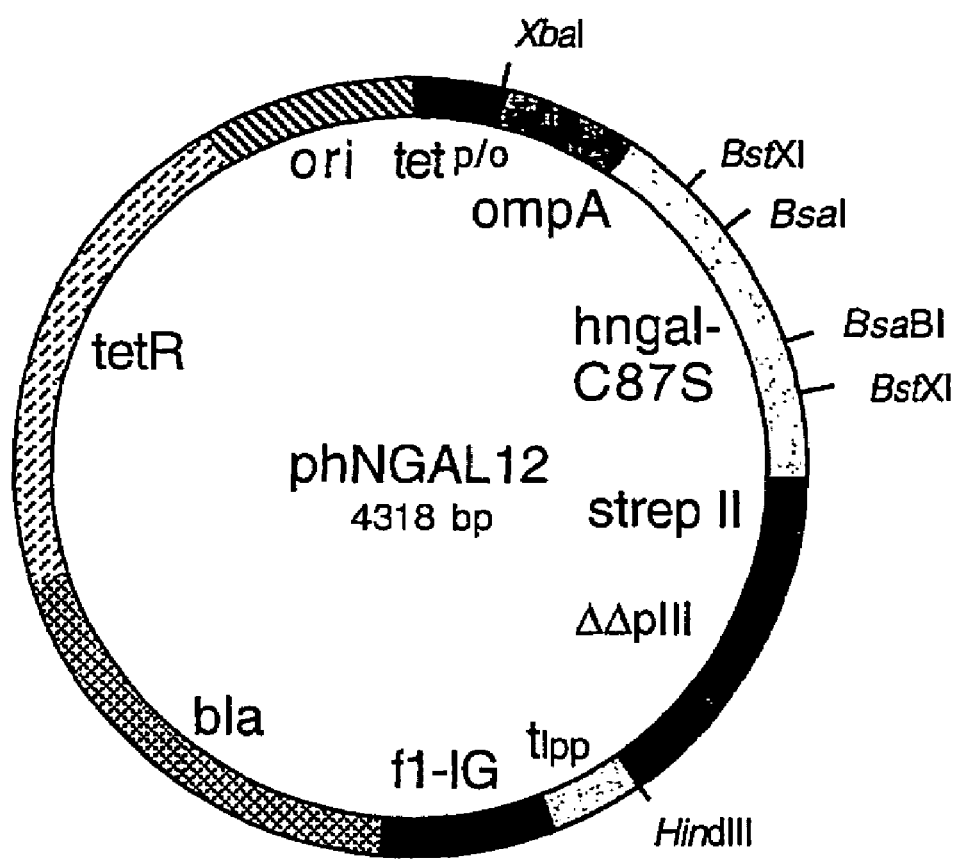

FIG. 6 shows a schematic drawing of phNGAL12. This vector codes for a fusion protein of the OmpA signal sequence, a modified hNGAL with the four amino acid substitutions Gln28 to His, Cys87 to Ser, Leu137 to Ile as well as Thr145 to Ala, the Strep-Tag® II affinity tag and a shortened form of the M13 coat protein pIII, comprising amino acids 217 to 406 (pIII). In addition, phNGAL12 carries two silent mutations within the coding region of the OmpA signal sequence in order to remove an EcoK12 restriction site. The entire structural gene is subject to transcriptional control by the tetracycline promoter/operator ($tet^{p/o}$) and ends at the lipoprotein transcription terminator ($t_{lpp}$). Further elements of the vector comprise the origin of replication (ori), the intergenic region of the filamentous bacteriophage f1 (f1-IG), the ampicillin resistance gene (bla) coding for β-lactamase, and the tetracycline repressor gene (tetR). An amber stop codon, which is partially translated into Gln in supE amber suppressor host strains, is located between the coding region for hNGAL, fused with the OmpA signal sequence and the Strep-Tag® II, and the coding region for the truncated pIII phage coat protein. The two BstXI restriction sites used for the cloning of the mutated gene cassette and the restriction sites flanking the structural gene are labelled. A relevant segment of the nucleic acid sequence of phNGAL12 is reproduced together with the encoded amino acid sequence in the sequence listing as SEQ ID NO:19. The segment begins with the XbaI restriction site and ends with the HindIII restriction site. The vector elements outside this region are identical with the vector pASK75, the complete nucleotide sequence of which is given in the German patent publication DE 44 17 598 A1.

Figure 7:
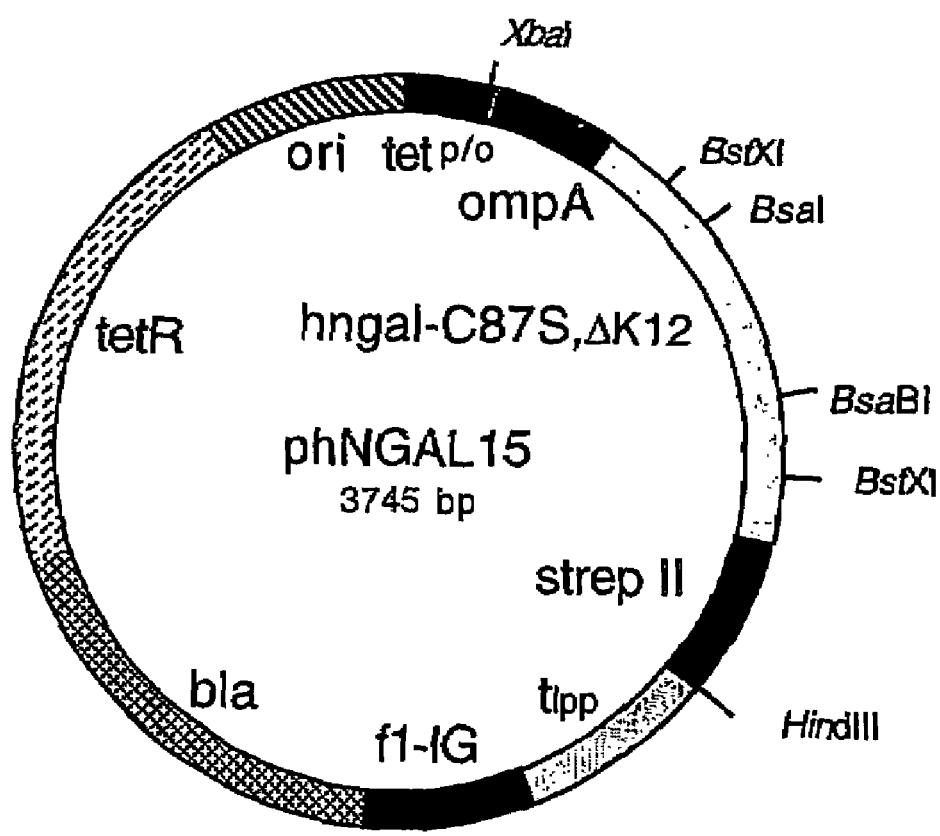

FIG. 7 shows a schematic drawing of phNGAL15. phNGAL15 codes for a fusion protein of the OmpA-signal sequence with a modified hNGAL according to FIG. 6 and the Strep-Tag® II affinity tag. phNGAL15 carries the same silent mutations within the coding region of the OmpA signal sequence as phNGAL12. A relevant segment of the nucleic acid sequence of phNGAL15 is reproduced together with the encoded amino acid sequence in the sequence listing as SEQ ID NO:21. The segment begins with the XbaI restriction site and ends with the HindIII restriction site. The vector elements outside this region are identical with the vector pASK75, the complete nucleotide sequence of which is given in the German patent publication DE 44 17 598 A1.

Figure 8:
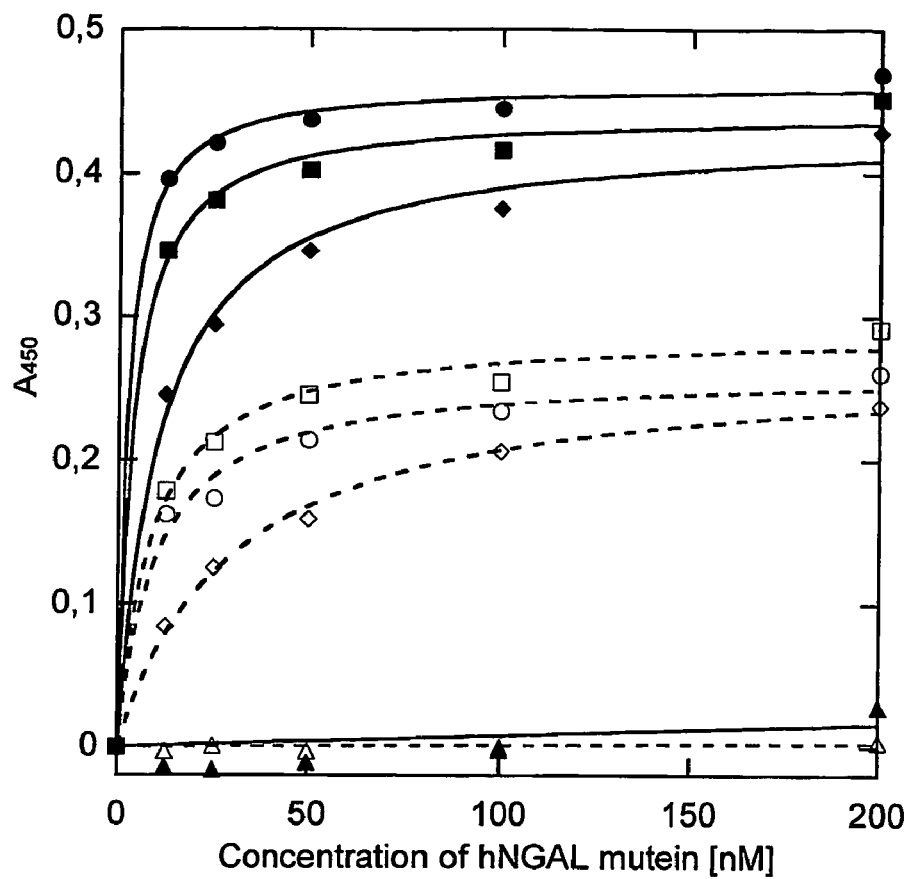
FIG. 8 depicts the binding of the muteins RFY-B, RFY-C, and RFY-E—together with hNGAL as control—to a thrombospondin peptide (SEQ ID NO: 18) in an ELISA.
Figure 8:
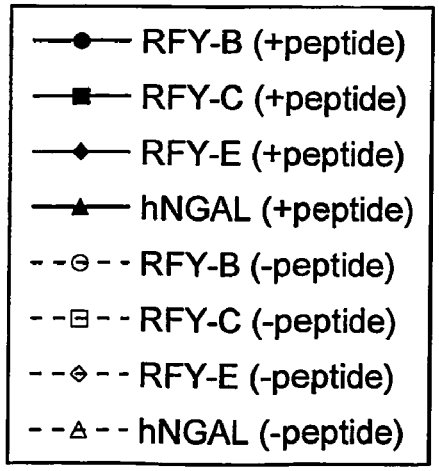

FIG. 8 shows a graphical representation of the data from Example 10, in which binding measurements with the hNGAL muteins and a thrombospondin peptide were performed by Enzyme-linked Immunosorbent Assay (ELISA). Binding of hNGAL muteins RFY-B (circles), RFY-C (squares), and RFY-E (diamonds) to the thrombospondin peptide was compared with the interaction of hNGAL (triangles) and the thrombospondin peptide. The thrombospondin peptide was immobilized to the avidin-coated microtiter plate via a biotin group attached to its C-terminus. The hNGAL muteins bind the thrombospondin peptide in a concentration-dependent manner, whereas hNGAL does not give rise to a significant binding signal. A low level of cross-reactivity between the hNGAL muteins and the avidin was observed in the absence of the peptide (open symbols).

Figure 9:
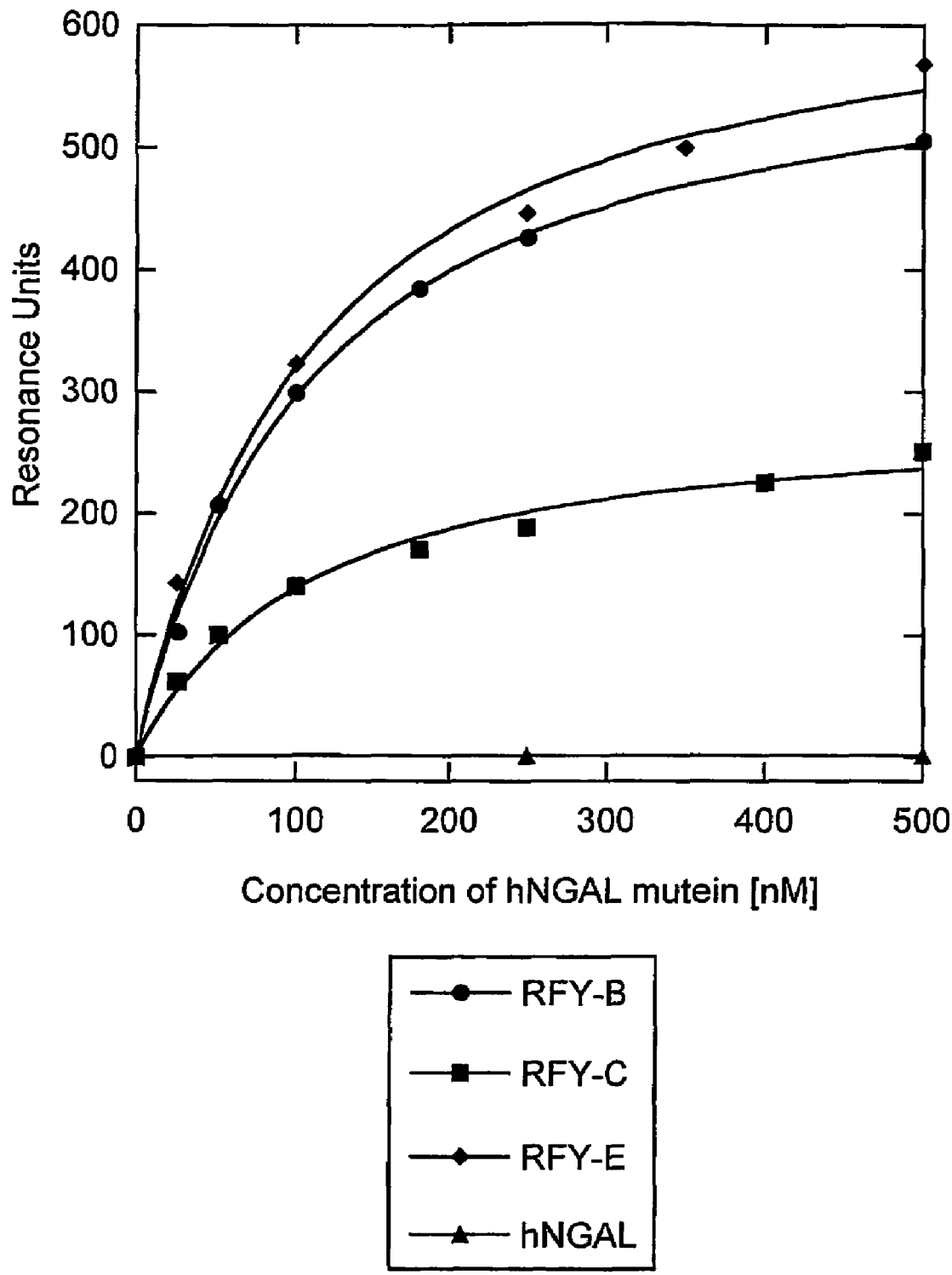
FIG. 9 depicts the binding of the muteins RFY-B, RFY-C, and RFY-E—together with hNGAL as control—to a thrombospondin peptide (SEQ ID NO: 18) according to surface plasmon resonance spectroscopy (SPR)

FIG. 9 shows a graphical representation of the data from Example 11, in which binding measurements with the hNGAL muteins to a thrombospondin peptide were performed employing surface plasmon resonance spectroscopy (SPR). The molecular interactions between hNGAL muteins RFY-B (circles), RFY-C (squares), and RFY-E (diamonds), respectively, with the thrombospondin peptide were compared with the interaction between hNGAL (triangles) and the thrombospondin peptide. The hNGAL muteins bind the thrombospondin peptide in a concentration-dependent manner, whereas hNGAL does not give rise to a significant binding signal. No cross-reactivity of the hNGAL muteins with the sensor chip SA was detected (not shown).

Figure 10:
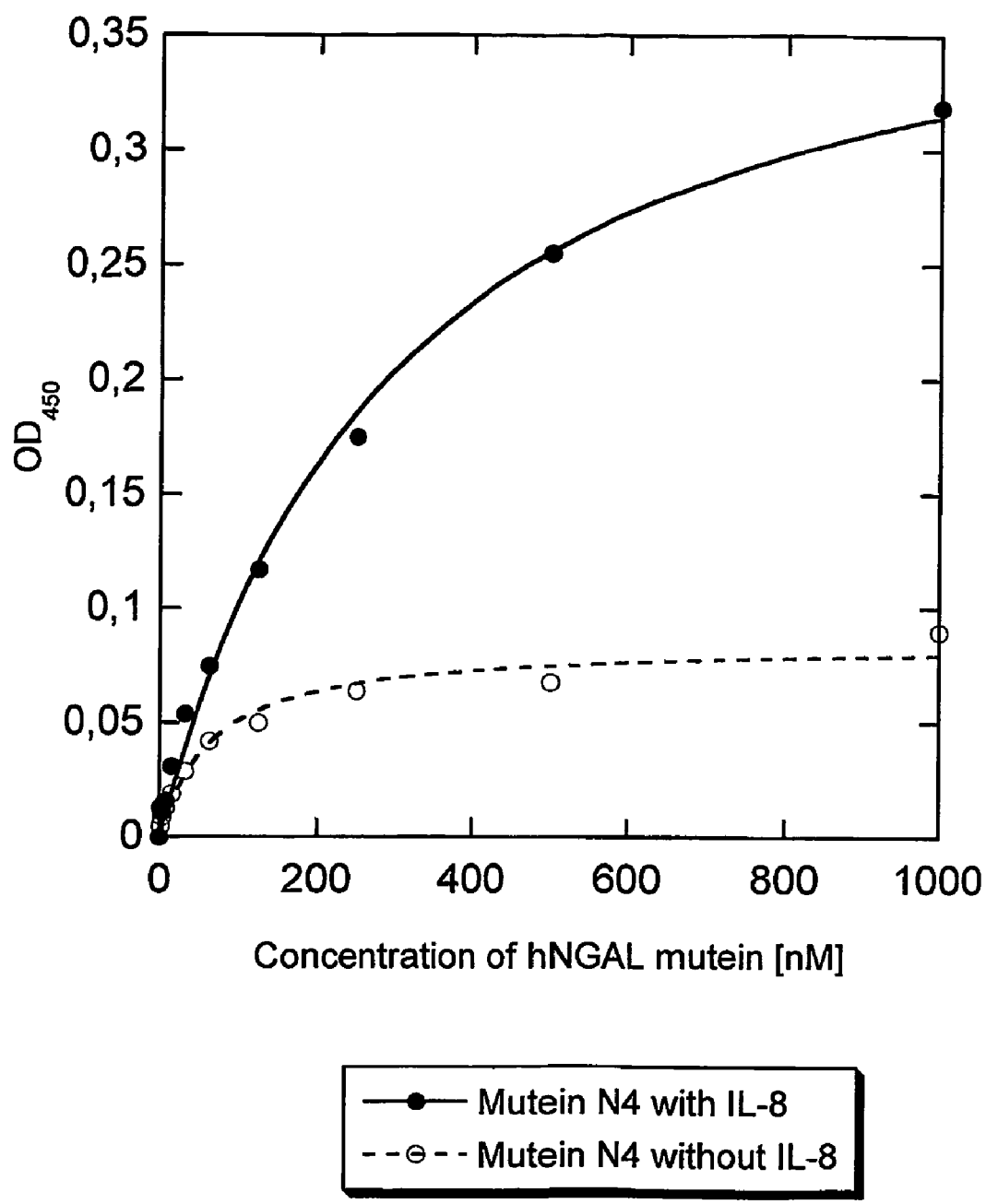
FIG. 10 depicts the binding of the hNGAL mutein N4 to interleukin-8 in an ELISA.

FIG. 10 shows a graphical representation of the data from Example 15, in which binding measurements with the hNGAL mutein N4 were performed by an Enzyme-linked Immunosorbent Assay (ELISA). Interleukin-8 was immobilized on the avidin-coated microtiter plate via biotin groups attached to its lysine residues. Binding of hNGAL mutein N4 to the interleukin-8 (closed circles) was compared with the interaction of hNGAL mutein N4 with avidin alone (open circles). The hNGAL mutein N4 binds interleukin-8 in a concentration-dependent manner, whereas it shows no significant binding signal with avidin alone.

FIG. 11 shows a schematic drawing of the plasmid pTNFα. pTNFα codes for a fusion protein made of the mature form of Tumor Necrosis Factor α (TNFα) as well as a hexahistidine tag at its N-terminus. All further genetic elements are identical with the plasmid pRSET (Schoepfer, Gene 124 (1993), 82-85). A relevant segment from the nucleic acid sequence of pTNFα is reproduced together with the encoded amino acid sequence in the sequence listing as SEQ ID NO:31. The segment begins with the NdeI restriction site and ends with the HindIII restriction site. The vector elements outside this region are identical with the vector pRSET5a, the complete nucleotide sequence of which is given under EMBL access No. X54202.

FIG. 12 (A) shows the result of the colony spot assay from Example 18, in which binding of trimeric TNFα to immobilized muteins of hNGAL was tested. *E. coli* TG1-F⁻ cells expressing the following ABD-fusion proteins were spotted either four or five times on a hydrophilic membrane according to (B): hNGAL, the bilin-binding protein (BBP), two unrelated muteins from the library described in Example 6, 9 clones isolated in the colony screening assay described in Example 17, and—as a control—no protein. The muteins secreted from the respective colonies were immobilized on a HSA-coated hydrophobic membrane as outlined in Example 18. Binding of digoxigenated TNFα was visualized employing an anti-digoxigenin Fab-Alkaline-Phosphatase conjugate. (B) depicts the positions where the respective clones were spotted on the membrane.

EXAMPLES

Example 1

Production of a Library for hNGAL Muteins

Unless otherwise indicated, genetic engineering methods known to the person skilled in the art were used, as for example described in Sambrook et al. (supra).

PCR was applied in multiple steps according to FIG. 2 for the concerted mutagenesis of in total 20 selected amino acid positions in the four peptide loops of hNGAL. The PCR reactions were carried out in a volume of 100 µl in both of the first amplification steps, wherein 20 ng phNGAL3 plasmid DNA was employed as template together with 50 pmol of each of the respective primers (SEQ ID NO:1 and SEQ ID NO:2 or SEQ ID NO:3 and SEQ ID NO:4, respectively), which had been synthesized according to the conventional phosphoramidite method. In addition, the reaction mixture contained 10 µl 10×Taq buffer (100 mM Tris/HCl pH 9,0, 500 mM KCl, 15 mM MgCl$_2$, 1% v/v Triton X-100), 10 µl dNTP-Mix (2 mM dATP, dCTP, dGTP, dTTP). After bringing to volume with water, 5 u Taq DNA-polymerase (5 u/µl, Promega) were added and 20 temperature cycles of 1 minute at 94° C., 1 minute at 60° C. and 1.5 minutes at 72° C. were carried out in a thermocycler with a heated lid (Eppendorf), followed by an incubation for 5 minutes at 60° C. The desired amplification products were isolated by preparative agarose gel electrophoresis from Low Melting Point Agarose (Roche Diagnostics) using the Jetsorb DNA extraction kit (Genomed).

The subsequent amplification step was also carried out in a 100 µl mixture, wherein approximately 6 ng of both of these respective fragments were used as templates, in the presence of 50 pmol of each of the primers SEQ ID NO:5 and SEQ ID NO:6. The remaining components of the PCR mixture were added in the same amounts as in the previous amplification steps. PCR took place with 20 temperature cycles of 1 minute at 94° C., 1 minute at 55° C., 1.5 minutes at 72° C., followed by a subsequent incubation for 5 minutes at 60° C. The PCR product was purified using the E.Z.N.A. Cycle-Pure Kit (PeqLab).

For the cloning of this fragment, which represented the library of the hNGAL muteins in nucleic acid form, it was first cut with the restriction enzyme BstXI (New England Biolabs) according to the instructions of the manufacturer and purified by means of the E.Z.N.A. Cycle-Pure Kit. After a second restriction digest with BstXI, the nucleic acid fragment was purified by preparative agarose gel electrophoresis, resulting in a double stranded DNA-fragment of 347 nucleotides in size. The DNA of the vector phNGAL5 was cut with BstXI in the same manner and the larger of the two resulting fragments (3971 bp) was isolated.

For the ligation, 2.75 µg (12 pmol) of the PCR fragment and 31.45 µg (12 pmol) of the vector fragment was incubated in the presence of 180 Weiss Units T4 DNA ligase (New England Biolabs) in a total volume of 600 µl (50 mM Tris/HCl pH 7.8, 10 mM MgCl$_2$, 10 mM DTT, 1 mM ATP, 50 µg/ml BSA) for four days at 16° C. The DNA was subsequently precipitated by adding 50 µg tRNA from yeast (Boehringer Mannheim), 125 µl 5 M ammonium acetate and 500 µl ethanol per 120 µl of ligation mixture. Incubation at −20° C. for three days was followed by centrifugation (30 minutes, 16000 g, 4° C.). Each precipitate was washed with 750 µl ethanol (70% v/v, −20° C.), centrifuged (5 minutes, 16000 g, 4° C.), and dried under vacuum (2 minutes). The DNA was finally dissolved in 200 µl TE/10 (1 mM Tris/HCl pH 8.0, 0.1 mM EDTA pH 8.0) and adjusted with water to a final volume of 260 µl.

The preparation of electrocompetent cells of the *E. coli* K12 strain XL1-blue (Bullock et al., supra) was carried out according to the methods described by Tung and Chow (Trends Genet. 11 (1995), 128-129) and by Hengen (Trends Biochem. Sci. 21 (1996), 75-76). 1 l LB-medium was adjusted by addition of a stationary XL1-blue overnight culture to an optical density at 600 nm of $OD_{600}$=0.08 and was incubated at 200 rpm and 26° C. in a 2 l Erlenmeyer flask. After reaching an $OD_{600}$=0.6, the culture was cooled for 30 minutes on ice and subsequently centrifuged for 15 minutes at 4000 g and 4° C. The cell sediment was washed twice each with 500 ml ice-cold 10% w/v glycerol and was finally resuspended in 2 ml of ice-cold GYT-medium (10% w/v glycerol, 0.125% w/v yeast extract, 0.25% w/v tryptone).

The Micro Pulser system (BioRad) was used with the cuvettes from the same vendor (electrode separation 2 mm) for the electroporation. All steps were carried out in the cold room at 4° C. Each 5 µl of the DNA solution mentioned above was mixed with 40 µl of the cell suspension, incubated for 1 minute on ice and finally transferred to the cuvette. After the electroporation the suspension was immediately diluted in 2 ml of ice-cold SOC-medium (2% w/v tryptone, 0.5% w/v yeast extract, 10 mM NaCl, 10 mM $MgSO_4$, 10 mM $MgCl_2$) and was shaken for 60 minutes at 37° C. and 200 rpm. The culture was diluted in 2 l 2xYT-medium with 100 µg/ml ampicillin (2YT/Amp) and cultivated until the $OD_{550}$ caused by the replicating cells was raised to 0.64. By employing in total 34.2 µg of the ligated DNA, $7 \times 10^7$ transformants were obtained in this way with 49 electroporation runs. The transformants were further used according to Example 2.

Example 2

Phagemid Presentation and Selection of hNGAL Muteins Against Human Tear Lipocalin 200 ml of the culture, containing the cells which were transformed with the phasmid vectors similar to phNGAL5 coding for the library of the lipocalin muteins as fusion proteins, were transferred to a sterile Erlenmeyer flask. After infection with VCS-M13 helper phage (Stratagene) at a multiplicity of infection of approximately 10 the culture was shaken for additional 30 minutes at 37° C., 160 rpm. Kanamycin (70 µg/ml) was subsequently added, the incubator temperature was lowered to 30° C. and, after 10 minutes, anhydrotetracycline (ACROS Organics) was added at 100 µg/l (200 µl of a 100 µg/ml stock solution in dimethylformamide, DMF) in order to induce gene expression. Incubation continued for another 5 hours at 30° C., 160 rpm.

50 ml were removed from this culture and the cells were sedimented by centrifugation (15 minutes, 12000 g, 4° C.). The supernatant containing the phagemid particles was sterile-filtered (0.45 µm), mixed with ¼ volume (12.5 ml) 20% w/v PEG 8000, 15% w/v NaCl, and incubated overnight at 4° C. After centrifugation (20 minutes, 18000 g, 4° C.) the precipitated phagemid particles were dissolved in 2 ml of cold PBS (4 mM $KH_2PO_4$, 16 mM $Na_2HPO_4$, 115 mM NaCl, pH 7.4). The solution was incubated on ice for 30 minutes and was distributed into two 1.5 ml reaction vessels. After centrifugation of undissolved components (5 minutes, 18500 g, 4° C.) each supernatant was transferred to a new reaction vessel.

Mixture with ¼ volume 20% w/v PEG 8000, 15% w/v NaCl and incubation for 30 to 60 minutes on ice served to reprecipitate the phagemid particles. After centrifugation (20 minutes, 18500 g, 4° C.) the supernatant was removed and the precipitated phagemid particles were dissolved and combined in a total of 400 µl PBS. After incubation for 30 minutes on ice the solution was centrifuged (5 minutes, 18500 g, 4° C.) in order to remove residual aggregates and the supernatant was used directly for the affinity enrichment.

Immuno-sticks (NUNC) were used for the affinity enrichment of the recombinant phagemids carrying the hNGAL mutein fusion proteins. These were coated overnight with 800 µl of human Tear Lipocalin (Tlpc) (450 µg/ml) in PBS.

For the production of recombinant Tlpc, cells of *E. Coli* JM83 (Yanisch-Perron et al., Gene 33 (1985), 103-119) were transformed with the expression plasmid pTLpc3 harbouring the cDNA of Tlpc (for the cDNA of Tlpc, see Holzfeind and Redl, Gene 139 (1994), 177-183) and used for protein production and purification according to example 3. The protein yield was approximately 2.2 mg per 1 l culture volume.

Unoccupied binding sites on the surface of the Immuno-Stick were saturated by incubation with 1.2 ml 2% w/v BSA in PBST (PBS with 0.1% v/v Tween 20) for 2 hours at RT. Afterwards the Immuno-Stick was incubated with a mixture of 250 µl of the phagemid solution and of 500 µl of blocking buffer (3% w/v BSA in PBST) for 1 hour at RT.

For the removal of unbound phagemids, washing was performed eight times, each time with 950 µL PBST for 2 minutes. Adsorbed phagemids were finally eluted by 10 minute treatment of the Immuno-Stick with 950 µl 0.1 M glycine/HCl pH 2.2, followed by immediate neutralisation of the pH of the elution fraction by mixing it with 150 W 0.5 M Tris.

For the amplification, this phagemid solution (1.1 ml, containing between $10^6$ and $10^8$ Colony-forming Units, depending on the selection cycle) was shortly warmed to 37° C., mixed with 3 ml of an exponentially growing culture of *E. coli* XL1-blue ($OD_{550}$=0.5), and incubated for 30 minutes at 37° C., 200 rpm. The cells infected with the phagemids were subsequently sedimented (2 minutes, 4420 g, 4° C.), resuspended in 600 µl of the culture medium, and plated out onto three agar plates with LB-medium containing 100 µg/ml ampicillin (LB/Amp; 140 mm diameter).

After incubation for 14 hours at 32° C., the cells were scraped from the agar plates, each with addition of 10 ml 2xYT/Amp-medium, were transferred to a sterile Erlenmeyer-flask, and were shaken for 20 minutes at 37° C., 200 rpm for complete suspension. 200 ml of 2xYT/Amp-medium prewarmed to 37° C. were inoculated to an $OD_{550}$=0.08 with an appropriate volume of this suspension.

For the repeated production and affinity enrichment of phagemid particles the same procedure as described at the beginning of this example was used. In these cases 50 ml 2xYT/Amp-medium was inoculated with 0.2 to 1 ml of the suspension of the cells grown on the agar plates and phagemids were produced during a period of seven instead of five hours at 30° C. Four further selection cycles with the Tlpc were carried out in this way.

Example 3

Identification of Human Tear Lipocalin-Binding hNGAL Muteins by Use of the "Colony Screening"-Method For the analytical production of the hNGAL muteins as fusion proteins with the Strep-Tag® II as well as with the albumin-binding domain and their characterization by colony screening, the gene cassette between the two BstXI cleavage sites was subcloned from the vector phNGAL5 on phNGAL7.

For this purpose the phasmid DNA was isolated from the mixture of the *E. coli* clones obtained by infection with the phagemids from Example 2 eluted as a result of the last selection cycle, using the Perfectprep Plasmid Midi Kit (Eppendorf). The DNA was cut with the restriction enzyme BstXI and the smaller of the two fragments (347 bp) was purified by preparative agarose-gel electrophoresis as described in Example 1. The DNA of the vector phNGAL7 was cut with BstXI and the larger of the two fragments (3971 bp) was isolated in the same way.

For the ligation, each 100 fmol of the two DNA-fragments were mixed with 1.5 Weiss Units T4 DNA ligase (Promega) in a total volume of 20 µl (30 mM Tris/HCl pH 7.8, 10 mM $MgCl_2$, 10 mM DTT, 1 mM ATP), followed by incubation overnight at 16° C. *E. coli* TG1-F$^-$ (*E. coli* K12 TG1, which had lost its episome through repeated culturing under non-selective conditions) was transformed with 2 µl of this ligation mixture according to the $CaCl_2$-method (Sambrook et al., supra).

A hydrophilic PVDF membrane (Millipore, type GVWP, pore size 0.22 µm), labelled at one position and cut to size, was laid onto an LB/Amp agar plate. 150 µl of the cell suspension from the transformation batch, which had been centrifuged (5000 g, 2 min, 4° C.) and resuspended in 500 µl of the culture medium, were uniformly plated onto this membrane. The agar plate was incubated for 7.5 hours at 37° C. until the colonies had reached a size of approximately 0.5 mm.

In the meantime a hydrophobic membrane (Millipore, Immobilon P, pore size 0.45 µm), also cut to size, was moistened with PBS according to the instructions of the manufacturer. It was subsequently agitated for 4 hours at RT in a solution of 10 mg/ml human serum albumin (HSA, Sigma) in PBS. Remaining binding sites on the membrane were saturated by incubation with 3% w/v BSA, 0.5% v/v Tween 20 in PBS for 2 hours at RT. The membrane was washed twice for 10 minutes each with 20 ml PBS and agitated afterwards for 10 minutes in 10 ml LB/Amp medium, to which 200 µg/l anhydrotetracycline were added. It was subsequently marked at one position and was laid onto a culture plate with LB/Amp agar, which additionally contained 200 µg/l anhydrotetracycline. The hydrophilic membrane on which the colonies were grown was laid onto the hydrophobic membrane in such a way that both of the marks superimposed. The culture plate was incubated with both membranes at 22° C. for 15 hours. During this phase the respective hNGAL muteins were secreted from the colonies and were immobilized via the albumin-binding domain on the HSA on the lower membrane.

After this, the upper membrane with the colonies was transferred to a fresh LB/Amp agar plate and stored at 4° C. The hydrophobic membrane was removed, washed three times for 5 minutes each with 20 ml PBST, and subsequently incubated for 1 hour in 10 ml of a solution of a conjugate (10 µg/ml) from Tear lipocalin and biotin in PBST. For the production of the conjugate, a solution of 0.285 mg D-biotinoyl-ε-amidocaproic acid-N-hydroxysuccinimide ester (Roche) in 9 µl DMSO was slowly added to 2.5 ml of 450 µg/ml Tlpc in 5% w/v $NaHCO_3$ (pH 8.2). After stirring for 1 hour at RT, excess reactant was removed by means of a PD-10 gel filtration column (Pharmacia) using PBS as running buffer.

After incubation with the conjugate, the membrane was washed three times with PBST, followed by incubation for 1 hour with 10 ml avidin-alkaline-phosphatase conjugate (Sigma, dilution 1:40000 in PBST). The membrane was subsequently washed each twice with PBST and once with PBS for 5 minutes and agitated for 10 minutes in AP-buffer (0.1 M Tris/HCl pH 8.8, 0.1 M NaCl, 5 mM $MgCl_2$). For the chromogenic reaction, the membrane was incubated in 10 ml AP-buffer, to which 30 µl 5-bromo-4-chloro-3-indolyl phosphate 4-toluidine salt (Roth, 50 µg/ml in dimethylformamide) and 5 µl nitro blue tetrazolium (Roth, 75 µg/ml in 70% v/v dimethylformamide) were added, until distinct colour signals could be recognized at the positions of some of the colonies. In this way the binding activity for the protein ligand, i.e. Tlpc, of the hNGAL muteins produced by these colonies was detected.

Twelve of the colonies giving rise to colour spots were cultured from the first membrane. Their plasmid DNA was isolated and the hNGAL gene cassette was subjected to sequence analysis by use of the Genetic Analyzer 310 system (Applied Biosystems) according to the instructions of the manufacturer using the oligodeoxynucleotide SEQ ID NO:11 as primer. The twelve sequenced clones exhibited only eight different sequences, which were named TlpcA, TlpcB, TlpcC, TlpcD, TlpcE, TlpcF, TlpcG, TlpcH. The clone TlpcA was found five times. The nucleotide sequences of the clones were translated into amino acid sequences and those amino acids deviating from hNGAL are given in Table 1. The amino acid sequence and the nucleotide sequence of the mutein TlpcA are also given as SEQ ID NO:12 and SEQ ID NO:13. The sequencing revealed amber stop codons, which were suppressed in the employed *E. coli* strains, at different positions in all of the selected variants.

Example 4

Production of the hNGAL Muteins

For the preparative production of hNGAL and its muteins one selected colony as well as the hNGAL originally encoded on phNGAL7, as a control, were produced in the *E. coli* strain TG1-F$^-$.

To this end, 100 ml of LB/Amp-medium were inoculated with a single colony of the TG1-F$^-$ transformant carrying the respective plasmid, and incubated overnight at 30° C., 200 rpm. 2 l of LB/Amp-medium in a 5 l-Erlenmeyer flask were then inoculated with each 40 ml of this preculture and were shaken at 22° C., 200 rpm to an $OD_{550}$=0.5. Induction was performed by adding 200 µg/l anhydrotetracycline (200 µl of a 2 mg/ml stock solution in DMF) followed by shaking for 3 further hours at 22° C., 200 rpm.

The cells from one flask were centrifuged (15 minutes, 4420 g, 4° C.) and, after decanting the supernatant, were resuspended in 20 ml of periplasmic release buffer (100 mM Tris/HCl pH 8.0, 500 mM sucrose, 1 mM EDTA) with cooling for 30 minutes on ice. Subsequently the spheroplasts were removed in two successive centrifugation steps (15 minutes, 4420 g, 4° C. and 15 minutes, 30000 g, 4° C.). The supernatant comprising the periplasmatic protein extract was dialyzed against CP-buffer (100 mM Tris/HCl pH 8.0, 150 mM NaCl, 1 mM EDTA), sterile-filtered, and served for the chromatographic purification.

The purification took place by means of the Strep-Tag® II-affinity tag (Schmidt et al., supra) which was situated between the hNGAL variant and the albumin binding domain. In the present case the streptavidin mutein "1" was employed (German Patent 196 41 876.3; Voss and Skerra, Protein Eng. 10 (1997), 975-982), which was coupled to an NHS-activated sepharose (Pharmacia) yielding 5 mg/ml immobilized streptavidin, relative to the bed volume of the matrix.

A 4 ml bed volume chromatography column filled with this material was equilibrated with 20 ml CP-buffer at 4° C. at a flow rate of 40 ml/h. Chromatography was monitored by measuring the absorption at 280 nm of the eluate in a flow-through photometer. After the application of the periplasmatic protein extract, the column was washed with CP-buffer until the base line was reached and the bound hNGAL mutein was subsequently eluted with 10 ml of a solution of 2.5 mM D-desthiobiotin (Sigma) in CP-buffer. The fractions containing the purified hNGAL mutein were checked via SDS-polyacrylamide gel electrophoresis (Fling und Gregerson, Anal. Biochem. 155 (1986), 83-88) and were pooled. The protein yields were between 30 µg and 70 µg per 1 l culture.

TABLE 1

Sequence characteristics of selected hNGAL muteins

| Pos. | hNGAL | TlpcA | TlpcB | TlpcC | TlpcD | TlpcE | TlpcF | TlpcG | TlpcH |
|---|---|---|---|---|---|---|---|---|---|
| 40 | Ala | Cys | Gly | Leu | Ser | Val | Gly | Arg | Ala |
| 42 | Leu | Val | Tyr | Pro | Val | Leu | Ser | Ser | Cys |
| 44 | Glu | Gln | Tyr | Ile | Phe | Gln* | Phe | Ile | Pro |
| 46 | Lys | Leu | Gln* | Gln* | Gln* | Cys | Arg | Phe | Leu |
| 47 | Asp | Leu | Arg | Ala | Ser | Trp | Phe | Gln* | Phe |
| 49 | Gln | Ser | Trp | Ile | Ser | Cys | Val | Val | Phe |
| 50 | Lys | Met | Ser | Phe | Ala | Pro | Gln | Phe | Leu |
| 70 | Leu | Leu | Leu | Glu | Gly | Asp | Ser | Pro | Gln* |
| 72 | Arg | Met | Arg | Ala | Asn | Glu | Gln* | Ala | Arg |
| 73 | Lys | Asp | Asp | Tyr | Lys | Lys | Gln | Asn | Pro |
| 77 | Asp | Arg | Pro | Val | Asn | Asn | Trp | Ile | Ser |
| 79 | Trp | Tyr | Met | Lys | Thr | Val | Arg | Ala | Arg |
| 101 | Pro | Gly | Leu | Tyr | Tyr | Pro | Phe | Val | Leu |
| 102 | Gly | Ile | Ser | Leu | Trp | Val | Pro | Val | Thr |
| 103 | Leu | Val | Leu | Tyr | Gln* | Leu | Ser | Thr | Met |
| 125 | Lys | Ser | Trp | Leu | Gly | Glu | Arg | Ala | Lys |
| 127 | Ser | Met | Ala | Cys | Arg | Ala | Lys | Lys | Ser |
| 128 | Gln | Thr | Asp | Pro | Met | Ser | Ala | Thr | Asp |
| 130 | Arg | Gln* | Gln | Gly | Glu | Gln | His | Lys | Asp |
| 132 | Tyr | Ala | Trp | Lys | Thr | Leu | Ser | Leu | Ile |
| 55 | Ile |  |  |  |  |  |  | Val° |  |
| 98 | Lys |  |  |  |  |  |  | Asn° |  |

*These glutamine residues were encoded by amber stop codons.
°These amino acid substitutions arose due to random mutations.

Example 5

Measurement of the Affinity of the hNGAL Muteins for Tear Lipocalin

For the detection of binding in an ELISA (Enzyme-linked Immunosorbent Assay) the wells of a microtiter plate (Micro Test III Flexible Assay Plate; Falcon) were filled each with 100 µl of a 20 mg/ml solution HSA in PBST and were incubated for 1 h at room temperature (RT). After washing three times with PBST, 50 µl of a 1 µM solution of the purified fusion protein of the hNGAL mutein TlpcA and of hNGAL from Example 3 were filled into the wells such that the protein was immobilized via complex formation between the abd and HSA. After one hour the solution was removed and washed three times with PBST. Then a dilution series in PBST was prepared of a conjugate of Tear lipocalin and biotin in PBST, starting from 140 µg/ml, (Example 3), followed by 1 hour incubation at RT. After washing three times with PBST, avidin-alkaline phosphate conjugate (Sigma), diluted 1:10000 with PBST, was filled into the wells. Incubation was performed for 1 hour at RT and followed by washing two times with PBST and two times with PBS. Detection of the Tear lipocalin bound to the immobilized hNGAL muteins was thus accomplished via hydrolysis of p-nitrophenyl phosphate, catalyzed by the alkaline phosphatase. For this purpose, 100 µl of a solution of 0.5 mg/ml p-nitrophenyl phosphate (Amresco) in AP-buffer (100 mM NaCl, 5 mM $MgCl_2$, 100 mM Tris/HCl pH 8.8) were filled into the wells and the product formation was monitored by measuring the absorption at 405 nm in a SpectraMax 250 photometer (Molecular Devices).

Example 6

Preparation of a Library with More than 10 Billion Independent hNGAL Muteins

A random library of hNGAL with enhanced diversity was prepared by concerted mutagenesis of in total 20 selected amino acid positions in the four peptide loops using PCR in multiple steps according to FIG. 2. The PCR reactions were performed in a volume of 100 µl in both of the first amplification steps, wherein 10 ng phNGAL5 (FIG. 1) plasmid DNA was employed as template, together with 50 pmol of each pair of primers (SEQ ID NO:1 and SEQ ID NO:2 or SEQ ID NO:3 and SEQ ID NO:4, respectively), which had been synthesized according to the conventional phosphoramidite method. In addition, the reaction mixture contained 10 µl 10×Taq buffer (100 mM Tris/HCl pH 9,0, 500 mM KCl, 15 mM $MgCl_2$, 1% v/v Triton X-100) and 10 µl dNTP-Mix (2 mM dATP, dCTP, dGTP, dTTP). After bringing to volume with water, 5 u Taq DNA-polymerase (5 u/4 µl, Promega) were added and 20 temperature cycles of 1 minute at 94° C., 1 minute at 60° C., and 1.5 minutes at 72° C. were carried out in a thermocycler with a heated lid (Eppendorf), followed by a final incubation for 5 minutes at 60° C. The desired amplification product was isolated in each case by preparative agarose gel electrophoresis from GTQ Agarose (Roth) using the Jetsorb DNA extraction kit (Genomed).

The subsequent amplification step was also carried out in a 100 µl mixture, wherein approximately 6 ng of the two DNA fragments were used as template in the presence of 50 pmol of each of the primers SEQ ID NO:5 and SEQ ID NO:6. Both of these primers carried a biotin group at their 5'-end, in contrast to Example 1. The remaining components of the PCR mixture were added in the same amounts as in the previous amplification steps. PCR was performed with 20 temperature cycles of 1 minute at 94° C., 1 minute at 60° C., 1.5 minutes at 72° C., followed by a subsequent incubation for 5 minutes at 60° C. The PCR product was purified using the E.Z.N.A. Cycle-Pure Kit (PeqLab).

For the cloning of the DNA fragment which represented the library of the hNGAL muteins in nucleic acid form, the 5'-biotinylated PCR product was cut with the restriction enzyme BstXI (Promega) according to the instructions of the manufacturer and the resulting fragment of 347 nucleotides in size was purified by preparative agarose gel electrophoresis as described above. Residual DNA-fragments which were not or incompletely digested were removed via their 5'-biotin tags by incubating their solution with streptavidin-coated paramagnetic beads (Dynal), thus obtaining the doubly cut DNA fragment suitable for the subsequent ligation reaction.

To this end, 100 µl of the commercially available suspension of the paramagnetic particles in a concentration of 10 mg/ml were washed three times with 100 µl TE-buffer. The paramagnetic particles were then drained and mixed with 11 to 22 pmol of the DNA-fragment in 100 µl TE-buffer for 15 min at room temperature. The paramagnetic particles were collected at the wall of the Eppendorf vessel with the aid of a magnet and the supernatant containing the purified DNA fragment was recovered for further use in the following ligation reaction.

The DNA of the vector phNGAL12 (FIG. 6) was cut with BstXI as described above and the larger of the two resulting fragments (3971 bp) was isolated by preparative agarose gel electrophoresis. For the ligation, 6.85 µg (30 pmol) of the PCR fragment and 78.65 µg (30 pmol) of the vector fragment were incubated in the presence of 855 Weiss Units of T4 DNA ligase (Promega) in a total volume of 8550 µl (50 mM Tris/HCl pH 7.8, 10 mM $MgCl_2$, 10 mM DTT, 1 mM ATP, 50 µg/ml BSA) for four days at 16° C. The DNA was then precipitated by adding 110 µg tRNA from yeast (Boehringer Mannheim), 350 µl 5 M ammonium acetate, and 1300 µl ethanol per 350 µl of the ligation mixture. Incubation at −20° C. for two days was followed by centrifugation (30 minutes, 16000 g, 4° C.). Each precipitate was washed with 750 µl ethanol (70% v/v, −20° C.), centrifuged (5 minutes, 16000 g, 4° C.), and dried under vacuum (2 minutes). The DNA was finally dissolved in a total volume of 427.5 µl water to a final concentration of 200 µg/ml.

The preparation of electrocompetent cells of the *E. coli* K12 strain XL1-blue (Bullock et al., supra) was carried out according to the methods described under Example 1.

The Micro Pulser system (BioRad) was used in conjunction with the cuvettes from the same vendor (electrode separation 2 mm) for the electroporation. All steps were carried out in the cold room at 4° C. Each 10 µl of the DNA solution (2 µg) from above was mixed with 100 µl of the cell suspension, incubated for 1 minute on ice, and transferred to the pre-chilled cuvette. Then the electroporation was performed (5 ms, 12.5 kV/cm) and the suspension was immediately diluted in 2 ml of ice-cold SOC-medium followed by shaking for 60 minutes at 37° C. and 200 rpm. The culture was diluted in 1.5 l 2×YT-medium containing 100 µg/ml ampicillin (2YT/Amp) to an $OD_{55}6$ of 0.5 and cultivated at 37° C. until the $OD_{550}$ was raised to 0.7 as caused by the replicating cells. By employing in total 85.5 µg of the ligated DNA, $1.8·10^{10}$ transformants were obtained in this manner using altogether 43 electroporation runs. The transformants were further used according to Example 7.

Example 7

Phagemid Presentation and Selection of hNGAL Muteins Against an Eight-Amino-Acid Peptide from the Cell-Binding Domain of Human Thrombospondin1 ("Thrombospondin Peptide")

The 1500 ml culture, containing the cells which were transformed with the phasmid vectors corresponding to phNGAL12, but coding for the library of the lipocalin muteins as fusion proteins, were infected with VCS-M13 helper phage (Stratagene) at a multiplicity of infection of approximately 10. The culture was shaken for additional 30 minutes at 37° C., 160 rpm. Then the incubator temperature was lowered to 26° C. and Kanamycin (70 µg/ml) was added. After 10 minutes, anhydrotetracycline was added at 25 µg/l (1875 µl of a 20 µg/ml stock solution in DMF) in order to induce gene expression. Incubation continued for another 15 hours at 26° C., 160 rpm.

The cells were sedimented by centrifugation (60 minutes, 12500 g, 4° C.). The supernatant containing the phagemid particles was sterile-filtered (0.45 µm), mixed with ¼ volume (375 ml) ice-cold 20% w/v PEG 8000, 15% w/v NaCl, and incubated for one hour at 4° C. After centrifugation (30 minutes, 18500 g, 4° C.) the precipitated phagemid particles were dissolved in 60 ml of cold PBS. The solution was incubated on ice for 60 minutes and was distributed into two SS34 centrifugation tubes. After centrifugation of undissolved components (5 minutes, 18500 g, 4° C.) each supernatant was transferred to a new centrifugation tube.

The phagemid particles were reprecipitated by mixing with ¼ volume 20% w/v PEG 8000, 15% w/v NaCl, followed by incubation for 60 minutes on ice. The phagemids were aliquoted (2 ml) and 1 mM EDTA and 50 mM benzamidine (Sigma) were added for long term storage at −20° C.

The biotinylated synthetic thrombospondin peptide derived from the cell binding domain of human Thrombospondin1 (Tulasne et al., Blood 98 (2001), 3346-3352; H$_2$N-Arg-Phe-Tyr-Val-Val-Met -Trp-Lys-Aca-Aca-Lys-Biotin-COOH, SEQ ID NO:18, Aca: amino caproic acid) was used together with Streptavidin-coated paramagnetic particles (Dynal) as target for affinity enrichment from the library of phagemids representing the hNGAL muteins.

For this purpose a 2 ml aliquot of the precipitated phagemids from above was centrifuged (20 minutes, 18500 g, 4° C.), the supernatant was removed, and the sedimented phagemid particles were dissolved in 1 ml PBS. After incubation for 30 minutes on ice the solution was centrifuged (5 minutes, 18500 g, 4° C.) to remove residual aggregates and the supernatant was directly used for the affinity enrichment.

In order to enrich peptide-binding phagemids, 40 µl of a 825 nM solution (33 pmol) of the biotinylated thrombospondin peptide in PBS (prepared by mixing 100 µl of a 10 µM solution of the synthetic peptide in DMF with 1112 µl PBS) was mixed with 260 µl of a solution of the freshly prepared phagemids (between $2 \cdot 10^{12}$ and $5 \cdot 10^{12}$ colony forming units, cfu) and incubated at RT for 1 h so that complex formation between the peptide and the muteins presented by the phagemids was able to occur. Then, 100 µl of a solution of 8% w/v BSA, 0.4% v/v Tween 20 in PBS was added.

Parallel thereto, 100 µl of the commercially available suspension of streptavidin-paramagnetic particles (Dynal) were washed three times with 100 µl PBS. Herein, the particles were kept suspended for 1 min by rotating the 1.5 ml Eppendorf vessel and then collected at the wall of the vessel with the aid of a magnet, and the supernatant was stripped off. In order to saturate unspecific binding sites, the paramagnetic particles were incubated with 100 µl of 2% w/v BSA in PBST at RT for 1 h.

After removing the supernatant, the mixture of the biotinylated thrombospondin peptide and the phagemids was added to the paramagnetic particles, and the particles were resuspended and incubated at RT for 10 min. Finally, free biotin-binding sites of streptavidin were saturated by adding 10 µl of a 4 mM D-desthiobiotin (Sigma) solution in PBS to the mixture and incubating said mixture at RT for 5 min. This step served for preventing the Strep-tag® II—as part of the fusion protein of the muteins and the phage coat protein pIII fragment—from forming a complex with streptavidin.

Unbound phagemids were removed by washing the paramagnetic particles eight times with 1 ml of fresh PBST containing 1 mM D-desthiobiotin. Each time the particles were collected with the aid of the magnet and the supernatant was stripped off. Finally the bound phagemids were eluted by resuspending the particles in 950 µl of 0.1 M glycine/HCl pH 2.2 and incubation for 15 minutes. After collecting the particles with the magnet, the supernatant was recovered and immediately neutralized by addition of 150 µl of 0.5 M Tris.

For the purpose of amplification, this phagemid solution (1.1 ml, containing between $10^7$ and $10^{10}$ cfu, depending on the selection cycle) was shortly warmed to 37° C., mixed with 3 ml of an exponentially growing culture of E. coli XL1-blue (OD$_{550}$=0.5 at 37° C.), and incubated for 30 minutes at 37° C., 200 rpm. The cells infected with the phagemids were subsequently sedimented (2 minutes, 4420 g, 4° C.), resuspended in 600 µl of the culture medium, and plated out onto three agar plates with LB-medium containing 100 µg/ml ampicillin (LB/Amp; 140 mm diameter).

After incubation for 14 hours at 32° C., the cells were scraped from the agar plates, each with addition of 10 ml 2×YT/Amp-medium, were transferred to a sterile Erlenmeyer-flask, and were shaken for 20 minutes at 37° C., 200 rpm for complete resuspension.

For another cycle of production and affinity enrichment of the phagemid particles 50 ml of 2×YT/Amp medium prewarmed to 37° C. were inoculated with 0.2 to 1 ml of said suspension so that the cell density was OD$_{550}$=0.08. This culture was incubated at 37° C., 160 rpm to a cell density of OD$_{550}$=0.5. Then the culture was infected with VCS-M13 helper phage (Stratagene) at a multiplicity of infection of approximately 10 and the culture was shaken for further 30 minutes at 37° C., 160 rpm. Kanamycin (70 µg/ml) was subsequently added, the incubator temperature was lowered to 26° C. and, after 10 minutes, anhydrotetracycline was added to 25 µg/l to induce gene expression. Incubation continued for another 15 hours at 26° C., 160 rpm.

The cells were sedimented by centrifugation (15 minutes, 12000 g, 4° C.). The supernatant containing the phagemid particles was sterile-filtered (0.45 µm), was mixed with 1/4 volume (12.5 ml) 20% w/v PEG 8000, 15% w/v NaCl, and was incubated for 1 h on ice. After centrifugation (20 minutes, 18000 g, 4° C.) the precipitated phagemid particles were dissolved in 2 ml of cold PBS. The solution was incubated on ice for 30 minutes and was distributed into two 1.5 ml reaction vessels. After centrifugation of undissolved components (5 minutes, 18500 g, 4° C.) each supernatant was transferred to a new reaction vessel.

The phagemid particles were reprecipitated by mixing with ¼ volume 20% w/v PEG 8000, 15% w/v NaCl, followed by incubation for 60 minutes on ice. After centrifugation (20 minutes, 18500 g, 4° C.) the supernatant was removed and the precipitated phagemid particles were dissolved in 1 ml PBS. After incubation for 30 minutes on ice the solution was centrifuged (5 minutes, 18500 g, 4° C.) and the supernatant was used directly for the affinity enrichment. Five further selection cycles with the thrombospondin peptide were carried out in this way.

Example 8

Identification of Thrombospondin Peptide-Binding hNGAL Muteins by Use of the "Colony Screening" Method For the analytical production of the hNGAL muteins as fusion proteins with the Strep-Tag® II and the albumin-binding domain the gene cassette between the two BstXI cleavage sites was subcloned from the vector phNGAL12 on phNGAL7.

For this purpose the phasmid DNA was isolated from the mixture of the *E. coli* clones obtained by infection with the phagemids from Example 7, eluted as a result of the fourth and the fifth selection cycle, using the Plasmid Midi Kit (Qiagen). The DNA of both preparations was cut with the restriction enzyme BstXI and in each case the smaller of the two fragments (347 bp) was purified by preparative agarose gel electrophoresis as described in Example 6. The DNA of the vector phNGAL7 was cut with BstXI and the larger of the two fragments (3971 bp) was isolated in the same way.

For the ligation, each 100 fmol of the isolated small DNA-fragments was mixed with 100 fmol of the large DNA-fragment and with 1.5 Weiss Units T4 DNA ligase (Promega) in a total volume of 20 μl (30 mM Tris/HCl pH 7.8, 10 mM $MgCl_2$, 10 mM DTT, 1 mM ATP), followed by incubation overnight at 16° C. *E. coli* TG1-F⁻ (*E. coli* K12 TG1, which had lost its episome through repeated culturing under non-selective conditions) was transformed with 2 μl of each of this ligation mixtures according to the $CaCl_2$-method (Sambrook et al., supra), obtaining 2.0 ml of a cell suspension. 100 μl of this suspension were plated out on an agar plate containing LB/Amp medium and incubated at 37° C. for 14 h.

Two hydrophilic PVDF membranes (Millipore, type GVWP, pore size 0.22 μm), labelled at one position and cut to size, were laid onto LB/Amp agar plates. 150 μl of the cell suspension from the transformation batches, which had been centrifuged (5000 g, 2 min, 4° C.) and resuspended in 500 μl of the culture medium, were uniformly plated onto these membranes. The agar plates were incubated for 7.5 hours at 37° C. until the colonies had reached a size of approximately 0.5 mm.

In the meantime two hydrophobic membranes (Millipore, Immobilon P, pore size 0.45 μm), also cut to size, were moistened with PBS according to the instructions of the manufacturer. They were then each agitated for 4 hours at room temperature in 10 ml of a solution of 10 mg/ml human serum albumin (HSA, Sigma) in PBS. Remaining binding sites on the membranes were saturated by incubation with 20 ml 3% w/v BSA, 0.5% V/v Tween 20 in PBS for 2 hours at RT. The membranes were washed twice for 10 minutes each with 20 ml PBS and immersed afterwards for 10 minutes in 10 ml LB/Amp medium, to which 200 μg/l anhydrotetracycline was added.

Finally, they were marked at one position and were laid onto culture plates with LB/Amp agar, which additionally contained 200 μg/l anhydrotetracycline. The hydrophilic membranes from above, on which the colonies were grown, were laid onto the hydrophobic membranes in such a way that both of the marks superimposed. The culture plates were incubated each with a stack of both membranes at 22° C. for 15 hours. During this phase the respective hNGAL muteins were secreted from the colonies on the upper membrane and were immobilized via their albumin-binding domain on the HSA on the lower membranes.

After this, the upper membranes with the colonies were transferred to fresh LB/Amp agar plates and stored at 4° C. The hydrophobic membranes were removed, washed three times for 5 minutes each with 20 ml PBST.

For analysis of the binding activity of the immobilized hNGAL muteins the membranes were then incubated for 1 hour in 10 ml of a 10 μg/ml solution of the biotinylated thrombospondin peptide in PBST (a 1 mM stock solution of the biotinylated peptide in DMF was therefore 1:100 diluted in PBST). The membranes were washed three times with PBST, followed by incubation for 1 hour with 10 ml avidin-alkaline phosphatase conjugate (Sigma, dilution 1:40,000 in PBST) for detection of bound peptides via their biotin groups. The membranes were washed twice with PBST and once with PBS, each for 5 minutes, and agitated for 10 minutes in AP-buffer (0.1 M Tris/HCl pH 8.8, 0.1 M NaCl, 5 mM $MgCl_2$). For the chromogenic reaction, the membranes were incubated in 10 ml AP-buffer, to which 30 μl 5-bromo-4-chloro-3-indolyl phosphate 4-toluidine salt (Roth, dissolved at 50 μg/ml in dimethylformamide) and 5 μl nitro blue tetrazolium (Roth, 75 μg/ml in 70% v/v dimethylformamide) were added, until distinct colour signals could be recognized at the positions of some of the colonies.

19 of the colonies (9 isolated from panning cycle four and 10 from cycle five) giving rise to intense colour spots on the hydrophobic membranes were cultured from the corresponding hydrophilic membranes. Their plasmid DNA was isolated and the hNGAL gene cassette was subjected to sequence analysis by use of the Genetic Analyzer 310 system with Big Dye Terminator Cycle Sequencing Kit (Applied Biosystems) according to the instructions of the manufacturer and using the oligodeoxynucleotide SEQ ID NO:11 as primer.

The 19 sequenced clones exhibited only twelve different sequences, which were named RFY-A, RFY-B, RFY-C, RFY-D, RFY-E, RFY-F, RFY-G, RFY-H, RFY-I, RFY-J, RFY-K and RFY-L. The clone RFY-B was found twice and the clone RFY-C was found six times. The clone RFY-J exhibited a deletion of 3 nucleotides, resulting in the deletion of one amino acid situated within peptide loop No. 4 at position 125. An amber stop codon, which is translated into the amino acid glutamine in a supE suppressor strain, was identified in clone RFY-L.

The nucleotide sequences of the clones were translated into amino acid sequences and those amino acids which deviate from the original hNGAL protein are given in Table 2a,b. The nucleotide sequences of the muteins RFY-B, RFY-C, and RFY-E are also given as SEQ ID NO:23, SEQ ID NO:25 and SEQ ID NO:27 in the sequence listing. The amino acid sequences of these muteins are given as SEQ ID NO:24, SEQ ID NO:26 and SEQ ID NO:28 in the sequence listing.

The muteins RFY-B and RFY-C, which were found twice and six times respectively were chosen for detailed characterization of their binding activity. In addition the mutein RFY-E was chosen, because its amino acid composition in the randomized regions appeared to be largely unique.

TABLE 2a

Sequence characteristics of selected hNGAL muteins

| Pos. | hNGAL | RFY-A | RFY-B | RFY-C | RFY-D | RFY-E | RFY-F | RFY-G | RFY-H |
|------|-------|-------|-------|-------|-------|-------|-------|-------|-------|
| 40   | Ala   | Phe   | Gly   | Gly   | Thr   | Gly   | Leu   | Ser   | Met   |

TABLE 2a-continued

Sequence characteristics of selected hNGAL muteins

| Pos. | hNGAL | RFY-A | RFY-B | RFY-C | RFY-D | RFY-E | RFY-F | RFY-G | RFY-H |
|---|---|---|---|---|---|---|---|---|---|
| 42 | Leu | Glu | Thr | His | Pro | Thr | Phe | Gly | Val |
| 44 | Glu | Leu | Tyr | Leu | Leu | Val | Ala | Pro | Leu |
| 46 | Lys | Ser | Arg | Asn | Val | Thr | Leu | Ser | Ile |
| 47 | Asp | Arg | Leu | Val | Leu | Leu | Phe | Leu | Pro |
| 49 | Gln | Phe | Ser | Pro | Thr | Ser | His | Arg | Asn |
| 50 | Lys | Thr | Val | Asn | Glu | Arg | Arg | Leu | Val |
| 70 | Leu | Met | Asp | Asp | Ile | Pro | Thr | His | Pro |
| 72 | Arg | Phe | Trp | Leu | Met | Met | Ser | Lys | Pro |
| 73 | Lys | Ser | Ala | Met | Asp | Gly | Ser | Asn | Ser |
| 77 | Asp | Leu | Asn | Pro | Leu | Lys | Ser | Pro | Gly |
| 79 | Trp | Leu | Lys | Phe | Pro | Lys | Lys | Lys | Glu |
| 101 | Pro | Phe | Leu | Pro | Asp | Met | Pro | Cys | Arg |
| 102 | Gly | Leu | Gly | Phe | Ala | Ser | Phe | Val | Gly |
| 103 | Leu | Asp | Leu | Leu | Leu | Asn | Ser | Ala | Asp |
| 125 | Lys | Asn | Pro | Asn | Pro | Gln | Pro | Glu | Arg |
| 127 | Ser | Ser | Gly | Pro | Lys | His | Ile | Leu | Leu |
| 128 | Gln | Gln | Gly | Arg | Asn | Lys | Ser | Asn | Lys |
| 130 | Arg | Arg | Ile | Tyr | Trp | Pro | Pro | Pro | Gln |
| 132 | Tyr | Tyr | Trp | Glu | Lys | Ser | Pro | Leu | Ile |
| 106 | | | Phe° | | | | | | |

TABLE 2b

Sequence characteristics of selected hNGAL muteins

| Pos. | hNGAL | RFY-I | RFY-J | RFY-K | RFY-L |
|---|---|---|---|---|---|
| 40 | Ala | Cys | Arg | Gln | Ser |
| 42 | Leu | Gly | Leu | Pro | Pro |
| 44 | Glu | Leu | Cys | Lys | Ser |
| 46 | Lys | Ser | Pro | His | Leu |
| 47 | Asp | Phe | Phe | Leu | Ala |
| 49 | Gln | Asn | Val | Ser | Gly |
| 50 | Lys | Gly | Arg | Leu | Gln* |
| 70 | Leu | Lys | Lys | Pro | Thr |
| 72 | Arg | His | Glu | Lys | Asn |
| 73 | Lys | Gly | Arg | Met | Ala |
| 77 | Asp | Arg | Ala | Pro | Ser |
| 79 | Trp | Thr | His | Ile | Arg |
| 101 | Pro | Gly | Lys | Ala | Asn |
| 102 | Gly | Ser | Phe | Trp | Phe |
| 103 | Leu | Cys | Ser | Glu | Ser |
| 125 | Lys | Met | ΔΔΔ | Thr | Lys |
| 127 | Ser | Leu | Pro | Gly | Lys |
| 128 | Gln | Asn | Ser | Thr | Lys |
| 130 | Arg | Asn | Ile | Pro | Asp |
| 132 | Tyr | Ser | Glu | Thr | Pro |
| 106 | Tyr | | | Ser° | |
| 126 | Val | | Pro° | | |

*This glutamine residue was encoded by an amber stop codon.
°These amino acid substitutions arose due to accidental mutations outside the randomized positions.
Δ This amino acid deletion arose due to an accidental mutation outside the randomized positions.

Example 9

Production of the hNGAL Muteins

For preparative production of the hNGAL muteins RFY-B, RFY-C, and RFY-E obtained from Example 8 the mutagenized coding region between the two BstXI cleavage sites was subcloned from the phNGAL7 vector on the expression plasmid phNGAL15 (FIG. 7). The plasmid thus obtained encoded a fusion protein of the mutein with the OmpA signal sequence, at the amino terminus and the Strep-Tag® II affinity tag at the carboxy terminus.

For subcloning, the plasmid DNA coding for the relevant mutein was cut with the restriction enzyme BstXI, and the smaller of the two fragments (347 bp) was purified by preparative agarose gel electrophoresis as described in Example 6. In the same manner, phNGAL15 vector DNA was cut with BstXI, and the larger of the two fragments (3398 bp) was isolated.

1.5 Weiss units of T4 DNA ligase (Promega) were added to 50 fmol of each of the two DNA fragments in a total volume of 20 µl (30 mM Tris/HCl pH 7.8, 10 mM MgCl$_2$, 10 mM DTT, 1 mM ATP) and for ligation the mixture was incubated at 16° C. for 16 h. 5 µl of the ligation mixture were then used to transform *E. coli* JM83 (Yanisch-Perron et al., Gene 33 (1985), 103-119) according to the CaCl$_2$ method, obtaining 2.0 ml of a cell suspension. 100 µl of this suspension were plated out on an agar plate containing LB/Amp medium and incubated at 37° C. for 14 h.

A single colony of the *E. coli*-JM83 transformants was used for inoculating 100 ml of LB/Amp-medium, followed by incubation overnight at 30° C., 200 rpm. 2 l of LB/Amp-medium in a 5 l-Erlenmeyer flask were then inoculated with 40 ml of this preculture and were shaken at 22° C., 200 rpm to an OD$_{550}$=0.5. Induction was performed by adding 200 µg/l anhydrotetracycline (200 µl of a 2 mg/ml stock solution in DMF) followed by shaking for 3 further hours at 22° C., 200 rpm.

The cells from one flask were centrifuged (15 minutes, 4420 g, 4° C.) and, after removing the supernatant, were resuspended in 20 ml of pre-chilled periplasmic release buffer (100 mM Tris/HCl pH 8.0, 500 mM sucrose, 1 mM EDTA) and incubated for 30 minutes on ice. The spheroplasts were then removed in two successive centrifugation steps (15 minutes, 4420 g, 4° C. and 15 minutes, 30000 g, 4° C.). The supernatant comprising the periplasmatic protein extract was dialyzed against CP-buffer (100 mM Tris/HCl pH 8.0, 150 mM NaCl, 1 mM EDTA), sterile-filtered, and used for the chromatographic purification of the hNGAL mutein.

The purification method was based on the C-terminal Strep-Tag® II-affinity tag (Schmidt et al., supra). In the present case the streptavidin mutein "1" was employed (German Patent 196 41 876.3; Voss and Skerra, supra), which was coupled to an NHS-activated sepharose (Pharmacia) yielding 5 mg/ml immobilized streptavidin per 1 ml of the bed volume of the matrix.

A 4 ml bed volume chromatography column filled with this material was equilibrated with 20 ml CP-buffer at 4° C. at a flow rate of 40 ml/h. Chromatography was monitored by measuring the absorption at 280 nm of the eluate in a flow-through photometer. After the application of the periplasmatic protein extract, the column was washed with CP-buffer until the base line was reached and the bound hNGAL mutein was subsequently eluted with 10 ml of a solution of 2.5 mM D-desthiobiotin (Sigma) in CP-buffer. The fractions containing the purified hNGAL mutein were checked via SDS-polyacrylamide gel electrophoresis (Fling and Gregerson, supra) and were pooled. To obtain suitable protein concentrations and buffer conditions for further applications the mutein pools were concentrated to a final volume of ca 500 µl using centricon tubes YM 10 (MW-cutoff 1000, Millipore) for ultrafiltration and subsequently dialysed against HBS-buffer (150 mM NaCl, 10 mM HEPES pH 7.4, 3 mM EDTA). The protein yields for RFY-B, RFY-C, and RFY-E were 70 µg, 60 µg and 200 µg respectively per 1 l of culture. In this manner both the original hNGAL and its muteins RFY-B, RFY-C, and RFY-E were prepared.

Example 10

Measurement of the Affinity of the hNGAL Muteins for the Thrombospondin Peptide in ELISA For the detection of binding in an ELISA (Enzyme-linked Immunosorbent Assay) the wells of a microtiter plate (Maxisorb, Nunc) were filled each with 50 µl of a 50 µg/ml solution of Avidin (Fluka) in PBS and were incubated over night at room temperature (RT). After washing three times with PBST, 50 µl of a 1 µM solution of the biotinylated thrombospondin peptide SEQ ID NO:18 in PBST were filled into the wells and the peptide was immobilized via complex formation between biotin and the preadsorbed avidin. After incubation for one hour the solution was removed and the wells of the microtiter plate were washed three times with PBST. In order to saturate unspecific binding sites, the wells were filled with 100 µl of 4% w/v BSA in PBST and incubated for one hour at RT, followed by three times washing with PBST.

Then a dilution series of the muteins from Example 9 was prepared, starting from 100 nM concentration, and followed by 1 hour incubation at RT. As a control for unspecific binding to avidin, a similar dilution series of hNGAL and its muteins was applied to wells where the thrombospondin peptide had been omitted. After washing three times with PBST, Anti-strepII-antibody-HRP-conjugate (IBA), diluted 1:8000 with PBST, was applied to the wells. Incubation was performed for 1 hour at RT and followed by washing three times with PBST and twice with PBS.

Detection of bound hNGAL muteins was accomplished using 3,3',5,5'-tetramethylbenzidine and H$_2$O$_2$ as substrates for horseradish-peroxidase. For this purpose, 100 µl of a ready-to-use HRP-substrate solution (Biochem Immunosystems) was filled into the wells and the colour development was stopped after a few minutes by adding 100 µl of 0.3 M sulphuric acid. Product formation was measured via the endpoint absorption at 450 nm in a SpectraMax 250 photometer (Molecular Devices).

The curve was fitted by non-linear least squares regression with the help of the computer program Kaleidagraph (Synergy software) according to the equation $[P \cdot L]=([P]_t[L]_t)/(K_D+[P]_t)$. Thereby $[P]_t$ is the total concentration of immobilized thrombospondin peptide (in A$_{450}$ units), $[L]_t$ is the concentration of the applied mutein or hNGAL, respectively, $[P \cdot L]$ is the concentration of the formed complex (in A$_{450}$ units), and $K_D$ is the apparent dissociation constant.

The resulting binding curves are depicted in FIG. 8. The values obtained for the apparent dissociation constants of the complexes between the hNGAL muteins and the thrombospondin peptide are summarized in the following table:

| hNGAL variant | K$_D$ [nM] |
| --- | --- |
| hNGAL: | —* |
| RFY-B: | 4.3 ± 0.2 |
| RFY-C: | 4.6 ± 0.6 |
| RFY-E: | 8.2 ± 0.8 |

*no detectable binding activity

Example 11

Measurement of the Affinity of the hNGAL Muteins for the Thrombospondin Peptide Using SPR The binding affinity of the hNGAL muteins to the thrombospondin peptide SEQ ID NO: 18 was determined by surface plasmon resonance (SPR) using the BIAcore X system (BIACORE). First 35 µl of the biotinylated thrombospondin peptide at a concentration of 1 µg/ml (prepared by mixing 1 µl of a 200 µg/ml peptide solution in DMF with 199 µl HBS buffer containing 150 mM NaCl, 10 mM HEPES pH 7.4, 3 mM EDTA) was immobilized to the surface of one flow channel of a streptavidin-coated sensor chip SA (BIACORE) according to the instructions of the manufacturer, resulting in an amount of ca. 400 response units (RU). Binding curves of the hNGAL muteins were then measured by applying 35 µl of each purified muteins from Example 9 in HBS buffer at concentrations between 500 nM and 25 nM using HBS-EP (HBS containing 0.005% Surfactant P20) as a running buffer and a continuous flowrate of 5 µl/min.

Steady state resonance values were measured at the end of the injection phase for the channel with the immobilized thrombospondin peptide for each protein concentration applied. Only negligible buffer effects were detected in the second channel of the sensor chip, which served as a control. These values were directly plotted against the concentration of the hNGAL mutein.

The curve was fitted by non-linear least squares regression with the help of the computer program Kaleidagraph (Synergy software) according to the equation $[P \cdot L] = ([P]_t [L]_t)/(K_D + [P]_t)$. Thereby $[P]_t$ is the total concentration of immobilized thrombospondin peptide (in RU), $[L]_t$ is the concentration of the applied mutein or hNGAL, respectively, $[P \cdot L]$ is the concentration of the formed complex (in RU), and $K_D$ is the dissociation constant under equilibration conditions.

The resulting binding curves are depicted in FIG. 9. The values obtained from SPR measurements for the dissociation constants of the complexes between the hNGAL muteins and the thrombospondin peptide are summarized in the following table:

| hNGAL variant | $K_D$ [nM] |
| --- | --- |
| hNGAL: | —* |
| RFY-B: | 105.4 ± 6.5 |
| RFY-C: | 106.1 ± 15.7 |
| RFY-E: | 107.2 ± 11.4 |

*no detectable binding activity

Example 12

Selection of hNGAL Muteins Against Human Interleukin-8 (IL-8)

The recombinant human cytokine interleukin-8 (Baggiolini and Clark-Lewis, FEBS Lett. 397, (1992), 97-101; H$_2$N-AVLPRSAKELRCQCIKTYSKPFHPK-FIKELRVIESGPHCANTEIIVKLSDGRELCLDP KEN-WVQRVVEKFLKRAENS-COOH; SEQ ID NO:29) was conjugated with biotin groups and used as a target for affinity enrichment from the library of phagemids representing the hNGAL muteins in the presence of streptavidin-coated paramagnetic particles (Dynal).

The conjugate was prepared by mixing 5.6 nmol (12.5 µg) of sulfosuccinimidyl-2-(biotinamido)ethyl-1,3-dithiopropionate (NHS-SS-Biotin, Pierce) dissolved in 3.4 µl H$_2$O with 1.4 nmol (12.5 µg) human recombinant IL-8 (Promocell) dissolved in 50 µl H$_2$O, 36.6 µl H$_2$O and with 10 µl 10× concentrated PBS/NaOH pH 8.5. The mixture was incubated under stirring at room temperature (RT) for 1 h. Excess reagent was then removed from the IL-8 conjugate by means of a PD-10 gel filtration column (Pharmacia) according to the manufacturer's instructions using PBS/NaOH pH 8.5 as running buffer. Biotinylated IL-8 eluted from the PD-10 column was adjusted to a final concentration of 1 µM with the same buffer resulting in a total volume of 1.24 ml. Labelled IL-8 was stored in aliquots at −80° C. and thawed directly prior to use.

For the isolation of phagemids displaying a mutein with affinity for IL-8, one aliquot of the precipitated phagemids, obtained as in Example 7, which were kept at −20° C. for long term storage, was thawed and the phagemids were pelleted (20 minutes, 18500 g, 4° C.). After removal of the supernatant, the sedimented phagemid particles were dissolved in 270 µl PBS, incubated for 30 minutes on ice and finally centrifuged (5 minutes, 18500 g, 4° C.) to remove residual aggregates.

In order to enrich IL-8-binding phagemids, 30 µl of a 1 µM solution (30 pmol) of biotinylated interleukin-8 was mixed with 270 µl of the phagemids in PBS (ca. $10^{13}$ cfu) and incubated at RT for 1 h so that complex formation between the cytokine and the muteins presented by the phagemids was allowed to occur. Then, 100 µl of a solution of 8% w/v BSA, 0.4% v/v Tween 20 in PBS was added.

Parallel thereto, 100 µl of the commercially available suspension of streptavidin-paramagnetic particles (Dynal) was washed three times with 1 ml PBS. Herein, the particles were kept suspended for 1 min by rotating the 1.5 ml Eppendorf vessel and then collected at the wall of the vessel with the aid of a magnet, and the supernatant was pipetted off. In order to saturate unspecific binding sites, the paramagnetic particles were incubated with 1 ml of 2% (w/v) BSA in PBST at RT for 1 h.

After removing the supernatant as above, the mixture of the biotinylated IL-8 and the phagemids was added to the paramagnetic particles, and the particles were resuspended and incubated at RT for 10 min. Finally, free biotin-binding sites of streptavidin were saturated by adding 10 µl of a 4 mM D-desthiobiotin (Sigma) solution in PBS to the mixture and incubating said mixture at RT for 5 min. This step served for preventing the Strep-tags II—as part of the fusion protein of the muteins and the phage coat protein pIII fragment—from forming a complex with streptavidin.

Unbound phagemids were removed by washing the paramagnetic particles eight times for 1 min with 1 ml of fresh PBST containing 1 mM D-desthiobiotin. Each time the particles were collected with the aid of the magnet and the supernatant was pipetted off. Finally, the bound phagemids were eluted under reducing conditions by resuspending the particles in 1 ml PBST containing 1 mM desthiobiotin and 100 mM DTT. The solution was incubated at 37° C. for 1 h to reduce the disulfide bond contained in the linker molecule between interleukin-8 and biotin, thus releasing phagemids specifically bound to IL-8 from the beads.

For the purpose of amplification, the eluted phagemid solution (1.0 ml, containing between $10^7$ and $10^8$ cfu, depending on the selection cycle) was shortly brought to 37° C., mixed with 3 ml of an exponentially growing culture of

*E. coli* XL1-blue (OD$_{550}$=0.5 at 37° C.), and was shaken at 200 rpm for 30 minutes at 37° C. The infected cells were sedimented (2 minutes, 4420 g, 4° C.), resuspended in 600 µl of culture medium, and plated out onto three agar plates with LB-medium containing 100 µg/ml ampicillin (LB/Amp; 140 mm diameter).

After incubation for 14 hours at 32° C., the lawn of colonies was scraped from the agar plates, each with addition of 10 ml 2×YT/Amp-medium. The suspension was transferred to a sterile Erlenmeyer-flask and shaken for 20 minutes at 37° C., 200 rpm.

For another cycle of production and affinity enrichment of the phagemid particles, 50 ml of 2×YT/Amp medium prewarmed to 37° C. was inoculated with 0.2 to 1 ml of said suspension so that the cell density was OD$_{550}$=0.08. This culture was incubated at 37° C., 160 rpm until a cell density of OD$_{550}$=0.5 was reached. Then, the culture was infected with VCS-M13 helper phage (Stratagene) at a multiplicity of infection of approximately 10 and the culture was shaken for further 30 minutes at 37° C., 160 rpm. Kanamycin (70 µg/ml) was subsequently added, the incubator temperature was lowered to 26° C. and, after 10 minutes, anhydrotetracycline was added to 25 µg/l to induce gene expression. Incubation continued for another 15 hours at 26° C., 160 rpm.

The cells were sedimented by centrifugation (15 minutes, 12000 g, 4° C.). The supernatant containing the phagemid particles was sterile-filtered (0.45 µm), was mixed with 1/4 volume (12.5 ml) 20% w/v PEG 8000, 15% w/v NaCl, and was incubated for 1 h on ice. After centrifugation (20 minutes, 18000 g, 4° C.) the precipitated phagemid particles were dissolved in 2 ml of cold PBS. The solution was incubated on ice for 30 minutes and was distributed into two 1.5 ml reaction vessels. After centrifugation of undissolved components (5 minutes, 18500 g, 4° C.) each supernatant was transferred to a new reaction vessel.

The phagemid particles were reprecipitated by mixing with ¼ volume 20% w/v PEG 8000, 15% w/v NaCl, followed by incubation for 60 minutes on ice. After centrifugation (20 minutes, 18500 g, 4° C.) the supernatant was removed and the precipitated phagemid particles were dissolved in 270 µl PBS. After incubation for 30 minutes on ice the solution was centrifuged (5 minutes, 18500 g, 4° C.) and the supernatant was used directly for the affinity enrichment. Four further selection cycles with IL-8 were carried out in this way.

Example 13

Identification of hNGAL Muteins Binding Interleukin-8 by Use of the "Colony Screening" Method For the analytical production of the hNGAL muteins as fusion proteins with the Strep-Tag® II and the albumin-binding domain as described in Example 3, the gene cassette between the two BstXI cleavage sites was subcloned from the vector phNGAL12 on phNGAL7.

For this purpose the phasmid DNA was isolated from the mixture of the *E. coli* clones obtained by infection with the phagemids from Example 12, eluted after the fifth selection cycle, using the Plasmid Midi Kit (Qiagen). The DNA was cut with the restriction enzyme BstXI and the smaller one of the two fragments (347 bp) was purified by preparative agarose gel electrophoresis as described in Example 6. The DNA of the vector phNGAL7 was cut with BstXI and the larger one of the two fragments (3971 bp) was isolated in the same way.

For the ligation, 100 fmol of the isolated small DNA-fragment was mixed with 100 fmol of the large DNA-fragment and incubated with 1.5 Weiss Units of T4 DNA ligase (Promega) in a total volume of 20 µl (30 mM Tris/HCl pH 7.8, 10 mM MgCl$_2$, 10 mM DTT, 1 mM ATP), followed by incubation overnight at 16° C. *E. coli* TG1-F$^-$ (*E. coli* K12 TG1, which had lost its episome through repeated culturing under non-selective conditions) was transformed with 4 µl of this ligation mixture according to the CaCl$_2$-method (Sambrook et al., supra), obtaining 2.0 ml of a cell suspension. The cell suspension was centrifuged (5000 g, 2 min, 4° C.), resuspended in 100 µl of the culture medium, plated on an agar plate containing LB/Amp medium and incubated at 37° C. for 14 h to determine the transformation efficiency.

A hydrophilic PVDF membrane (Millipore, type GVWP, pore size 0.22 µm), labelled at one position and cut to size, was laid onto an LB/Amp agar plate. The cell suspension from a fresh transformation batch, which had been transformed with 5-10 µl of the ligation mixture described above, was centrifuged (5000 g, 2 min, 4° C.), resuspended in 100 µl of the culture medium, and uniformly plated onto this membrane in order to obtain 400 to 500 colonies. The agar plate was incubated for 7.5 hours at 37° C. until the colonies had reached a size of approximately 0.5 mm.

In the meantime, a hydrophobic membrane (Millipore, Immobilon P, pore size 0.45 µm), also cut to size, was moistened with PBS according to the instructions of the manufacturer. Coating with HSA was achieved by agitation for 4 hours at RT in 10 ml of a solution of 10 mg/ml HSA (Sigma) in PBS. Remaining binding sites on the membrane were saturated by incubation with 20 ml 3% (w/v) BSA, 0.1% (v/v) Tween-20 in PBS for 2 hours at RT. The membrane was washed twice for 10 minutes with 20 ml PBS and immersed afterwards for 10 minutes in 10 ml LB/Amp medium, to which 200 µg/l anhydrotetracycline was added.

Finally, it was marked at one position and laid onto a culture plate with LB/Amp agar, which additionally contained 200 µg/l anhydrotetracycline. The hydrophilic membrane from above, on which the colonies were grown, was laid onto the hydrophobic membrane in such a way that both marks superimposed. The culture plate was incubated with the stack of both membranes at 22° C. for 15 hours. During this phase the respective hNGAL muteins were secreted from the colonies on the upper membrane and were immobilized via their albumin-binding domain via the HSA at the lower membrane.

After this, the upper membrane with the colonies was transferred to a fresh LB/Amp agar plate and stored at 4° C. The hydrophobic membrane was removed and washed three times for 5 minutes each with 20 ml PBST.

For analysis of the binding activity of the immobilized hNGAL muteins, the membrane was incubated for 1 hour in 3.5 ml of a solution of 100 nM digoxigenated IL-8 in PBS.

The conjugate was prepared by mixing 14 nmol (9.2 µg) of digoxigenin-3-O-methylcarbonyl-ε-aminocaproic acid N-hydroxysuccinimide ester (DIG-NHS, Roche) dissolved in 2.3 µl DMSO with 1.4 nmol (12.5 µg) human recombinant IL-8 (Promocell) dissolved in 50 µl H$_2$O, 37.7 µl H$_2$O and with 10 µl 10× concentrated PBS/NaOH pH 8.5. The mixture was incubated under stirring at RT for 1 h. Excess reagent was removed from the IL-8 conjugate by means of a PD-10 gel filtration column (Pharmacia) according to the manufacturer's instructions using PBS/NaOH pH 8.5 as running buffer. Digoxigenated IL-8 eluted from the PD-10 column was adjusted to a final concentration of 1 μM with the same buffer resulting in a total volume of 1.56 ml. Labelled IL-8 was stored in aliquots at −80° C. and thawed directly prior to use.

The membrane was washed three times with PBST, followed by incubation for 1 hour with 10 ml anti-digoxigenin Fab-Alkaline-Phosphatase conjugate diluted 1:1000 in PBST for detection of bound IL-8 via its digoxigenin groups. The membrane was washed twice with PBST and once with PBS, each for 5 minutes, and agitated for 10 minutes in AP-buffer. For the chromogenic reaction, the membrane was incubated in 10 ml AP-buffer, to which 30 μl 5-bromo-4-chloro-3-indolyl phosphate 4-toluidine salt (Roth, dissolved at 50 μg/ml in dimethylformamide) and 5 μl nitro blue tetrazolium (Roth, 75 μg/ml in 70% v/v dimethylformamide) were added, until distinct colour signals could be recognized at the positions of some of the colonies.

From 200 colonies which appeared on the membrane 9 gave rise to an intense colour spot on the hydrophobic membrane and were cultured from the corresponding hydrophilic membrane. Their plasmid DNA was isolated and the hNGAL gene cassette was subjected to sequence analysis by use of the Genetic Analyzer 310 system with Big Dye Terminator Cycle Sequencing Kit (Applied Biosystems) according to the instructions of the manufacturer and using the oligodeoxynucleotide SEQ ID NO:5 as primer.

All 9 clones exhibited the identical sequence, indicating that a single mutein was preferentially enriched during the selection procedure. This mutein was named variant N4.

The nucleotide sequences of the clone N4 was translated into its amino acid sequence and those amino acid residues which deviate from the original hNGAL protein are given in Table 3. The nucleotide sequence and the full amino acid sequence of the mutein N4 is also given as SEQ ID NO:30 and SEQ ID NO: 34.

TABLE 3

Sequence characteristics of hNGAL mutein N4

| Pos. | hNGAL | N4 |
| --- | --- | --- |
| 40 | Ala | Asp |
| 42 | Leu | Tyr |
| 44 | Glu | Ala |
| 46 | Lys | Ser |
| 47 | Asp | Leu |
| 49 | Gln | Gly |
| 50 | Lys | Leu |
| 70 | Leu | Val |
| 72 | Arg | Tyr |
| 73 | Lys | Asp |
| 77 | Asp | Val |
| 79 | Trp | Ser |
| 101 | Pro | Glu |
| 102 | Gly | Ala |

TABLE 3-continued

Sequence characteristics of hNGAL mutein N4

| Pos. | hNGAL | N4 |
| --- | --- | --- |
| 103 | Leu | Val |
| 125 | Lys | Asp |
| 127 | Ser | Arg |
| 128 | Gln | Pro |
| 130 | Arg | Ser |
| 132 | Tyr | Glu |

Example 14

Production of the hNGAL Mutein N4

For preparative production of the hNGAL mutein N4 obtained from Example 13, the BstXI cassette was isolated from the variant in phNGAL7 and subcloned onto the expression plasmid phNGAL15 (FIG. 7). The resulting plasmid encodes a fusion protein of the mutein N4 with the OmpA signal sequence at the amino terminus and the Strep-Tag® II affinity tag at the carboxy terminus.

For subcloning, the phNGAL7 plasmid DNA coding for the relevant mutein was cut with the restriction enzyme BstXI, and the smaller one of the two fragments (347 bp) was purified by preparative agarose gel electrophoresis as described in Example 6. In the same manner, phNGAL15 vector DNA was cut with BstXI, and the larger one of the two fragments (3398 bp) was isolated.

1.5 Weiss units of T4 DNA ligase (Promega) were added to 50 fmol of each of the two DNA fragments in a total volume of 20 μl (30 mM Tris/HCl pH 7.8, 10 mM MgCl$_2$, 10 mM DTT, 1 mM ATP) and for ligation the mixture was incubated at 16° C. for 16 h. 5 μl of the ligation mixture was then used to transform E. coli JM83 (Yanisch-Perron et al., supra) according to the CaCl$_2$ method, obtaining 2.0 ml of a cell suspension. 100 μl of this suspension were plated on agar containing LB/Amp medium and incubated at 37° C. for 14 h.

A single colony of the E. coli JM83 transformants was used to inoculate 100 ml of LB/Amp-medium, followed by incubation overnight at 30° C. and 200 rpm. 2 l of LB/Amp-medium in a 5 l-Erlenmeyer flask were then inoculated with 40 ml of this preculture and were shaken at 22° C. and 200 rpm until an OD$_{550}$=0.5 was reached. Expression of the mutein N4 was induced by adding 200 μg/l anhydrotetracycline (200 μl of a 2 mg/ml stock solution in DMF) and incubation was continued for another 3 hours.

The cells from one flask were centrifuged (15 minutes, 5571 g, 4° C.) and, after removing the supernatant, were resuspended in 20 ml of pre-chilled periplasmic release buffer (100 mM Tris/HCl pH 8.0, 500 mM sucrose, 1 mM EDTA) and incubated for 30 minutes on ice. The spheroplasts were then removed in two successive centrifugation steps (15 minutes, 2988 g, 4° C. and 15 minutes, 25000 g, 4° C.). The supernatant comprising the periplasmatic protein extract was dialyzed against CP-buffer (100 mM Tris/HCl pH 8.0, 150 mM NaCl, 1 mM EDTA), sterile-filtered, and used for the chromatographic purification of the hNGAL mutein.

The purification method was based on the C-terminal Strep-Tag® II affinity tag (Schmidt et al., supra) employing Strep-Tactin® Superflow-material (IBA). A 4 ml bed volume chromatography column filled with of this material was equilibrated with 20 ml CP-buffer at 4° C. at a flow rate of 2 ml/min. Chromatography was monitored by measuring the absorption at 280 nm in a flow-through photometer. After application of the periplasmatic protein extract (flow rate 0.8 ml/min) the column was washed with CP-buffer at a flow rate of 2 ml/min until the base line was reached. Bound hNGAL mutein was eluted with a solution of 2.5 mM D-desthiobiotin (Sigma) in CP-buffer at a flow rate of 1 ml/min. The fractions (2.5 ml each) containing the purified hNGAL mutein were pooled, concentrated to a final volume of approximately 500 µl using YM 10 centricon tubes (MW-cutoff 10 kDa, Millipore) and analysed on a 15% SDS-polyacrylamide gel (Fling and Gregerson, supra). Finally, the material was sterilized by filtration (0.22 µm) and stored at 4° C.

Example 15

Measurement of the Affinity of the hNGAL Mutein N4 for IL-8 in an ELISA Assay

For the detection of binding in an ELISA experiment two rows (12 wells each) of a 96 microtiter plate (Maxisorb, Nunc) were coated with 50 µl of a 50 µg/ml solution of Avidin (Fluka) in PBS overnight at 4° C. After washing three times with PBST, one row was treated with 50 µl/well of a 1 µM solution of biotinylated IL-8 in PBST, whereas the second row was incubated with PBST as a control. After 1 hour at RT, all wells were washed three times with PBST and unspecific binding sites were saturated with 100 µl of 4% w/v skimmed milk powder in PBST for 1 hour at RT.

To determine the $K_D$ value of the mutein N4 for IL-8, a dilution series of the N4 protein from Example 14 was prepared in PBST, starting from a concentration of 1 µM. As a control for unspecific binding to avidin, a similar dilution series of the mutein N4 was applied to wells where the IL-8 had been omitted. Complex formation was allowed for 1 hour at RT, followed by three washes with PBST and incubation at RT for 1 hour with anti-strepII-antibody-HRP-conjugate (IBA) diluted 1:8000 in PBST.

Detection of bound mutein N4 was accomplished using 3,3',5,5'-tetramethylbenzidine and $H_2O_2$ as substrates for horseradish-peroxidase. For this purpose, all wells were filled with 100 µl of a ready-to-use HRP-substrate solution (Biochem Immunosystems). The colour development was stopped after a few minutes by adding 100 µl of 0.3 M sulphuric acid. Product formation was measured via end-point absorption at 450 nm in a SpectraMax 250 photometer (Molecular Devices).

The curve was fitted by non-linear least squares regression with the help of the computer program Kaleidagraph (Synergy software) according to Example 10. The resulting binding curves are depicted in FIG. 10. The value obtained for the apparent dissociation constant of the complex between the hNGAL mutein N4 and IL-8 is 300±34 nM.

Example 16

Selection of hNGAL Muteins Against Biotinylated TNFα

Recombinant human Tumor Necrosis Factor α (TNFα, SEQ ID NO:31, SEQ ID NO: 35) was conjugated with biotin groups and used as a target for affinity enrichment from the library of phagemids representing the hNGAL muteins obtained as described in Example 7 in the presence of Streptavidin-coated paramagnetic particles (Dynal).

For the production of recombinant TNF□, cells of *E. coli* BL21 [DE3] were transformed with the expression plasmid pTNF□ encoding the cytokine TNF□ (Wang et al., Science 228 (1985), 149-154) with an N-terminal Arg-Gly-Ser-His (6)-Gly(3)-tag. Expression of TNF□ was performed as described by Schmidt and Skerra (Schmidt and Skerra., J Chromatogr. 676 (1994), 103-119) except that the production of the recombinant cytokine was induced at 30° C. for 4 hours. Under these conditions, TNFα accumulates as soluble protein in the cytoplasm and can be released by subsequently freezing and thawing the cell pellet of 1 l culture medium in 30 ml lysis buffer (50 mM $NaH_2PO_4$/NaOH pH 8.0, 300 mM NaCl, 10 mM imidazole). TNFα was purified from that solution in its trimeric form (Lohrengel et al., Cytokine 12 (1999), 573-577) by subsequently employing Immobilized Metal Affinity Chromatography (IMAC; Porath et al., Nature 258, (1975) 598-599) and size exclusion chromatography. The protein yield was approximately 1.5 mg per 1l culture volume.

The conjugate was prepared by reacting 40 nmol (24.3 µg) of NHS-SS-Biotin (Pierce) dissolved in 25 µl $H_2O$ with 10 nmol (187.7 µg) human recombinant TNF□ dissolved in 235 µl PBS/NaOH pH 8.5 in a total volume of 1 ml PBS/NaOH pH 8.5. The mixture was incubated with stirring at room temperature (RT) for 1 h. Excess reagent was then removed from the TNF□ conjugate by means of a PD-10 gel filtration column (Pharmacia) according to the manufacturer's instructions with PBS as running buffer.

For the isolation of phagemids displaying a mutein with affinity for TNFα, one aliquot of the precipitated phagemids obtained as in Example 7, which were kept at −20° C. for long term storage, was thawed and the phagemids were pelleted (20 minutes, 18500 g, 4° C.). After removal of the supernatant, the sedimented phagemid particles were dissolved in 270 µl PBS, incubated for 30 minutes on ice and finally centrifuged (5 minutes, 18500 g, 4° C.) to remove residual aggregates.

30 µl of a 1 µM solution (30 pmol) of biotinylated TNFα (prepared by mixing 200 µl of a 2.5 µM solution of the biotinylated cytokine in PBS with 300 µl PBS) was mixed with 270 µl of the phagemids in PBS (ca. $10^{13}$ cfu) and incubated at RT for 1 h so that complex formation between the cytokine and the muteins presented by the phagemids was allowed to occur. Then, 100 µl of a solution of 8% w/v BSA, 0.4% v/v Tween 20 in PBS was added.

Parallel thereto, 100 µl of the commercially available suspension of streptavidin-paramagnetic particles (Dynal) was washed three times with 1 ml PBS. Herein, the particles were kept suspended for 1 min by rotating the 1.5 ml Eppendorf vessel and then collected at the wall of the vessel with the aid of a magnet, and the supernatant was pipetted off. In order to saturate unspecific binding sites, the paramagnetic particles were incubated with 1 ml of 2% (w/v) BSA in PBST at RT for 1 h.

After removing the supernatant as above, the mixture of the biotinylated TNF□ and the phagemids was added to the paramagnetic particles, and the particles were resuspended and incubated at RT for 10 min. Finally, free biotin-binding sites of streptavidin were saturated by adding 10 µl of a 4 mM D-desthiobiotin (Sigma) solution in PBS to the mixture and incubating said mixture at RT for 5 min. This step served for preventing the Strep-tag® II—as part of the fusion protein of the muteins and the phage coat protein pIII fragment—from forming a complex with streptavidin.

Unbound phagemids were removed by washing the paramagnetic particles eight times for 1 min with 1 ml of fresh PBST containing 1 mM D-desthiobiotin. Each time the particles were collected with the aid of the magnet and the supernatant was pipetted off. Finally, the bound phagemids were eluted under reducing conditions by resuspending the particles in 1 ml PBST containing 1 mM desthiobiotin and 100 mM DTT. The solution was incubated at 37° C. for 1 h to reduce the disulfide bond contained in the linker molecule between TNF☐ and biotin, thus releasing phagemids specifically bound to TNF☐ from the beads.

For the purpose of amplification, the eluted phagemid solution (1.0 ml, containing between $10^7$ and $10^9$ cfu, depending on the selection cycle) was shortly brought to 37° C., mixed with 3 ml of an exponentially growing culture of E. coli XL1-blue ($OD_{550}$=0.5 at 37° C.), and was shaken at 200 rpm for 30 minutes at 37° C. The infected cells were sedimented (2 minutes, 4420 g, 4° C.), resuspended in 600 µl of culture medium, and plated out onto three agar plates with LB-medium containing 100 µg/ml ampicillin (LB/Amp; 140 mm diameter).

After incubation for 14 hours at 32° C., the lawn of colonies was scraped from the agar plates, each with addition of 10 ml 2×YT/Amp-medium. The suspension was transferred to a sterile Erlenmeyer-flask and was shaken for 20 minutes at 37° C., 200 rpm.

For another cycle of production and affinity enrichment of the phagemid particles 50 ml of 2×YT/Amp medium pre-warmed to 37° C. was inoculated with 0.2 to 1 ml of said suspension so that the cell density was $OD_{550}$=0.08. This culture was incubated at 37° C., 160 rpm until a cell density of $OD_{550}$=0.5 was reached. Then the culture was infected with VCS-M13 helper phage (Stratagene) at a multiplicity of infection of approximately 10 and the culture was shaken for further 30 minutes at 37° C., 160 rpm. Kanamycin (70 µg/ml) was subsequently added, the incubator temperature was lowered to 26° C. and, after 10 minutes, anhydrotetracycline was added to 25 µg/l to induce gene expression. Incubation continued for another 15 hours at 26° C., 160 rpm.

The cells were sedimented by centrifugation (15 minutes, 12000 g, 4° C.). The supernatant containing the phagemid particles was sterile-filtered (0.45 µm), was mixed with 1/4 volume (12.5 ml) 20% w/v PEG 8000, 15% w/v NaCl, and was incubated for 1 h on ice. After centrifugation (20 minutes, 18000 g, 4° C.) the precipitated phagemid particles were dissolved in 2 ml of cold PBS. The solution was incubated on ice for 30 minutes and was distributed into two 1.5 ml reaction vessels. After centrifugation of undissolved components (5 minutes, 18500 g, 4° C.) each supernatant was transferred to a new reaction vessel.

The phagemid particles were reprecipitated by mixing with 1/4 volume 20% w/v PEG 8000, 15% w/v NaCl, followed by incubation for 60 minutes on ice. After centrifugation (20 minutes, 18500 g, 4° C.) the supernatant was removed and the precipitated phagemid particles were dissolved in 270 µl PBS. After incubation for 30 minutes on ice the solution was centrifuged (5 minutes, 18500 g, 4° C.) and the supernatant was used directly for the affinity enrichment. Four further selection cycles with TNF☐ peptide were carried out in this way.

Example 17

Identification of hNGAL Muteins Binding TNFα by Use of the "Colony Screening" Method For the analytical production of the hNGAL muteins as fusion proteins with the Strep-Tag® II and the albumin-binding domain as described in Example 3, the gene cassette between the two BstXI cleavage sites was subcloned from the vector phNGAL12 on phNGAL7.

For this purpose the phasmid DNA was isolated from the mixture of the E. coli clones obtained by infection with the phagemids from Example 16, eluted after the fifth selection cycle, using the Plasmid Midi Kit (Qiagen). The DNA was cut with the restriction enzyme BstXI and the smaller one of the two fragments (347 bp) was purified by preparative agarose gel electrophoresis as described in Example 6. The DNA of the vector phNGAL7 was cut with BstXI and the larger one of the two fragments (3971 bp) was isolated in the same way.

For the ligation, 100 fmol of the isolated small DNA-fragment was mixed with 100 fmol of the large DNA-fragment and incubated with 1.5 Weiss Units of T4 DNA ligase (Promega) in a total volume of 20 µl (30 mM Tris/HCl pH 7.8, 10 mM $MgCl_2$, 10 mM DTT, 1 mM ATP), followed by incubation overnight at 16° C. E. coli TG1-F⁻ (E. coli K12 TG1, which had lost its episome through repeated culturing under non-selective conditions) was transformed with 4 µl of this ligation mixture according to the $CaCl_2$-method (Sambrook et al., supra), obtaining 2.0 ml of a cell suspension. The cell suspension was centrifuged (5000 g, 2 min, 4° C.), resuspended in 100 µl of the culture medium, plated on an agar plate containing LB/Amp medium and incubated at 37° C. for 14 h to determine the transformation efficiency.

A hydrophilic PVDF membrane (Millipore, type GVWP, pore size 0.22 µm), labelled at one position and cut to size, was laid onto an LB/Amp agar plate. The cell suspension from a fresh transformation batch, which had been transformed with 3-6 µl of the above described ligation mixture, was centrifuged (5000 g, 2 min, 4° C.), resuspended in 100 µl of the culture medium, and uniformly plated onto this membrane in order to obtain 400 to 500 colonies. The agar plate was incubated for 7.5 hours at 37° C. until the colonies had reached a size of approximately 0.5 mm.

In the meantime a hydrophobic membrane (Millipore, Immobilon P, pore size 0.45 µm), also cut to size, was moistened with PBS according to the instructions of the manufacturer. Coating with HSA was achieved by agitation for 4 hours at RT in 10 ml of a solution of 10 mg/ml HSA (Sigma) in PBS. Remaining binding sites on the membrane were saturated by incubation with 20 ml 4% (w/v) skimmed milk powder, 0.1% (v/v) Tween-20 in PBS for 2 hours at RT. The membrane was washed twice for 10 minutes with 20 ml PBS and immersed afterwards for 10 minutes in 10 ml LB/Amp medium, to which 200 µg/l anhydrotetracycline was added.

Finally, it was marked at one position and laid onto a culture plate with LB/Amp agar, which additionally contained 200 µg/l anhydrotetracycline. The hydrophilic membrane from above, on which the colonies were grown, was laid onto the hydrophobic membrane in such a way that both of the marks superimposed. The culture plate was incubated with the stack of both membranes at 22° C. for 15 hours. During this phase the respective hNGAL muteins were secreted from the colonies on the upper membrane and were immobilized via their albumin-binding domain via the HSA on the lower membrane.

After this, the upper membrane with the colonies was transferred to a fresh LB/Amp agar plate and stored at 4° C. The hydrophobic membrane was removed and washed three times for 5 minutes each with 20 ml PBST.

For analysis of the binding activity of the immobilized hNGAL muteins the membrane was then incubated for 1 hour in 3.5 ml of a solution of 100 nM digoxigenated TNFα in PBST containing 0.5% w/v skimmed milk powder.

The conjugate was prepared by reacting 40 nmol (27.5 µg) of DIG-NHS (Roche) dissolved in 27 µl DMSO with 10 nmol (187.7 µg) TNFα dissolved in 235 µl PBS/NaOH pH 8.5 in a total volume of 1 ml PBS/NaOH pH 8.5. The mixture was incubated with stirring at room temperature (RT) for 1 h. Excess reagent was then removed from the TNFα conjugate by means of a PD-10 gel filtration column (Pharmacia) according to the manufacturer's instructions with PBS as running buffer.

The membrane was washed three times with PBST, followed by incubation for 1 hour with 10 ml anti-digoxigenin Fab-Alkaline-Phosphatase conjugate diluted 1:1000 in PBST for detection of bound TNFα via its digoxigenin groups. The membrane was washed twice with PBST and once with PBS, each for 5 minutes, and agitated for 10 minutes in AP-buffer. For the chromogenic reaction, the membrane was incubated in 10 ml AP-buffer, to which 30 µl 5-bromo-4-chloro-3-indolyl phosphate 4-toluidine salt (Roth, dissolved at 50 µg/ml in dimethylformamide) and 5 µl nitro blue tetrazolium (Roth, 75 µg/ml in 70% v/v dimethylformamide) were added, until distinct colour signals could be recognized at the positions of some of the colonies.

From 1800 colonies which appeared on the membranes of multiple colony screening experiments 14 giving rise to intense colour spots on the hydrophobic membrane were cultured from the corresponding hydrophilic membrane. Their plasmid DNA was isolated and the hNGAL gene cassette was subjected to sequence analysis by use of the Genetic Analyzer 310 system with Big Dye Terminator Cycle Sequencing Kit (Applied Biosystems) according to the instructions of the manufacturer and using the oligodeoxynucleotide SEQ ID NO:5 as primer.

From these 14 muteins, 13 exhibited the same sequence, which was denominated TNF-V1, whereas the fourteenth sequence was different and was designated TNF-V2.

The nucleotide sequences of the clones TNF-V1 and TNF-V2 were translated into their amino acid sequences and those amino acid residues which deviate from the original hNGAL protein are given in Table 4. The nucleotide sequences of the muteins TNF-V1 and TNF-V2 are also given as SEQ ID NO:32 and SEQ ID NO:33, respectively. The full amino acid sequences of these two muteins are given as SEQ ID NO: 36 and SEQ ID NO: 37, respectively.

TABLE 4

Sequence characteristics of hNGAL muteins TNF-V1 and TNF-V2

| Pos. | hNGAL | TNF-V1 | TNF-V2 |
| --- | --- | --- | --- |
| 40 | Ala | Phe | Gly |
| 42 | Leu | Phe | Phe |
| 44 | Glu | Leu | Val |
| 46 | Lys | Leu | Phe |
| 47 | Asp | Glu | Asn |
| 49 | Gln | Phe | Ile |
| 50 | Lys | Phe | Ser |
| 70 | Leu | Thr | Asp |
| 72 | Arg | Leu | Ala |
| 73 | Lys | Glu | Asn |
| 77 | Asp | Phe | Ala |
| 79 | Trp | Glu | Arg |
| 80 | Ile | ΔΔΔ* | Ile |
| 101 | Pro | Lys | Gly |
| 102 | Gly | His | Asn |
| 103 | Leu | Gly | Val |
| 125 | Lys | Asp | Gly |
| 127 | Ser | Ser | Asp |
| 128 | Gln | Gln | Ser |
| 130 | Arg | Arg | Asn |
| 132 | Tyr | Asn | Arg |

*Mutein TNF-V1 lacks the isoleucine residue at position 80 due to a deletion of nucleotides 238 to 240.

Example 18

Confirmation of the Binding Activity of Selected hNGAL Muteins for TNFα by Use of the "Colony Spot Assay"

The colony spot assay was conducted in a similar manner as the colony screening assay outlined in Example 17 except that single colonies of E. coli harbouring the corresponding expression plasmids were spotted from a master plate onto the hydrophilic membrane—marked with a grid—instead of plating a suspension of transformed cells. Each respective clone was spotted with a sterile tooth pick either four or five times onto a hydrophilic membrane (Millipore, type GVWP, pore size 0.22 µm) that was placed on a culture plate with LB/Amp agar. Cells were grown at 37° C. for 5 hours.

In the meantime a hydrophobic membrane (Millipore, Immobilon P, pore size 0.45 µm) was moistened with PBS according to the instructions of the manufacturer. Coating with HSA was achieved by agitation for 4 hours at RT in 10 ml of a solution of 10 mg/ml HSA (Sigma) in PBS. Remaining binding sites on the membrane were saturated by incubation with 20 ml 3% (w/v) BSA, 0.1% (v/v) Tween-20 in PBS for 2 hours at RT. The membrane was washed twice for 10 minutes with 20 ml PBS and immersed afterwards for 10 minutes in 10 ml LB/Amp medium, to which 200 µg/l anhydrotetracycline was added.

Finally, it was marked at one position and laid onto a culture plate with LB/Amp agar, which additionally contained 200 µg/l anhydrotetracycline. The hydrophilic membrane from above, on which the colonies were grown, was laid onto the hydrophobic membrane in such a way that both of the marks superimposed. The culture plate was incubated with the stack of both membranes at 22° C. for 15 hours. During this phase the respective hNGAL muteins were secreted from the colonies on the upper membrane and were immobilized via their albumin-binding domain on the HSA on the lower membrane.

After this, the upper membrane with the colonies was transferred to a fresh LB/Amp agar plate and stored at 4° C. The hydrophobic membrane was removed and washed three times for 5 minutes each with 20 ml PBST.

To confirm the binding activity of the spotted muteins towards TNFα the membrane was then incubated for 1 hour in 3.5 ml of a solution of 100 nM digoxigenated TNFα in PBST containing 0.5% w/v skimmed milk powder (a 1.5 µM stock solution of the digoxigenated TNFα in PBS was therefore 1:15 diluted in PBST containing skimmed milk powder).

The membrane was washed three times with PBST, followed by incubation for 1 hour with 10 ml anti-digoxigenin Fab-Alkaline-Phosphatase conjugate diluted 1:1000 in PBST for detection of bound TNFα via its digoxigenin groups. The membrane was washed twice with PBST and once with PBS, each for 5 minutes, and agitated for 10 minutes in AP-buffer. For the chromogenic reaction, the membranes were incubated in 10 ml AP-buffer, to which 30 µl 5-bromo-4-chloro-3-indolyl phosphate 4-toluidine salt (Roth, dissolved at 50 µg/ml in dimethylformamide) and 5 µl nitro blue tetrazolium (Roth, 75 µg/ml in 70% v/v dimethylformamide) were added. Distinct colour signals could be recognized at those positions where the muteins TNF-V1 and TNF-V2 were spotted, whereas no binding signal could be observed for hNGAL wildtype (encoded by phNGAL7), bilin-binding protein (encoded by the vector pBBP22; Schlehuber et al. J. Mol. Biol. 297 (2000), 1105-1120), two unrelated muteins from the library of hNGAL muteins described in Example 6 (both subcloned on phNGAL7), and for the clone expressing no protein (harbouring pBluescript (Stratagene) as a plasmid), confirming the binding activity of TNF-V1 and TNF-V2 to TNFα (FIG. 12).

The invention claimed is:

1. A method for generating a mutein of a protein selected from the group consisting of human neutrophil gelatinase-associated lipocalin (hNGAL), rat $\alpha_2$-microglobulin-related protein (A2m) and mouse 24p3/uterocalin (24p3), said mutein having detectable affinity to a given target, comprising:

subjecting the protein to mutagenesis at one or more of the sequence positions which correspond to the sequence positions 40 to 50, 70 to 79, 101 to 103, and 125 to 132 of hNGAL, resulting in one or more mutein(s) of the protein.

2. The method of claim 1 further comprising:

enriching at least one resulting mutein having binding affinity for a given target from the one or more muteins by selection and/or isolating said at least one mutein.

3. The method of claim 1 wherein the mutagenesis results in a plurality of muteins of the protein.

4. The method according to claim 1 wherein the protein is subjected to mutagenesis at one or more of the sequence positions which correspond to the sequence positions 40, 42, 44, 46, 47, 49, 50, 70, 72, 73, 77, 79, 101, 102, 103, 125, 127, 128, 130, and 132 of hNGAL.

5. The method according to claim 1, wherein a nucleic acid coding for the one or more mutein(s) of the protein, which nucleic acid results from mutagenesis, is operably fused at the 3' end with a gene coding for the coat protein pIII of a filamentous bacteriophage of the M13-family or for a fragment of this coat protein, in order to select at least one mutein for the binding of the given target.

6. A mutein derived from a protein selected from the group consisting of: human neutrophil gelatinase-associated lipocalin (hNGAL), rat $\alpha_2$-microglobulin-related protein (A2m) and mouse 24p3/uterocalin (24p3), wherein the mutein comprises a mutation at one or more of the sequence positions corresponding to sequence positions 40 to 50, 70 to 79, 101 to 103, and 125 to 132 of hNGAL, and wherein the mutein has detectable binding affinity for a given target.

7. A mutein according to claim 6, wherein the mutein comprises a mutation at one or more of the sequence positions, which correspond to the sequence positions 40, 42, 44, 46, 47, 49, 50, 70, 72, 73, 77, 79, 101, 102, 103, 125, 127, 128, 130, and 132 of hNGAL.

8. The hNGAL mutein to claim 6, wherein Cys87 is substituted and/or wherein the mutein carries one or more of the amino acid substitutions Glu28→His, Thr145→Ala compared to hNGAL.

9. The hNGAL mutein according to claim 6 having an amino acid sequence selected from the group consisting of SEQ ID NO: 17, SEQ ID NO: 24, SEQ ID NO: 26 and SEQ ID NO: 28.

10. A mutein according to claim 6, which is conjugated to a label selected from the group consisting of an organic molecule, an enzyme label, radioactive label, fluorescent label, chromogenic label, luminescent label, a hapten, digoxigenin, biotin, metal complexes, metals, and colloidal gold.

11. A fusion protein comprising a mutein selected from the group consisting of hNGAL, A2m and 24p3 according to claim 6, wherein at least one fusion partner is selected from the group consisting of an enzyme, a protein, a protein domain, a peptide, a signal sequence, and an affinity tag operably fused to the amino terminus or the carboxy terminus of the mutein.

12. A nucleic acid molecule comprising a sequence encoding a mutein of a protein selected from the group consisting of hNGAL, A2m, and 24p3, as defined in claim 6.

13. A pharmaceutical composition comprising a mutein of a protein selected from the group consisting of hNGAL, A2m, and 24p3 as defined in claim 6 and a pharmaceutically acceptable carrier.

14. A method for producing a mutein of a protein selected from the group consisting of hNGAL, A2m, and 24p3 as defined in claim 6, wherein the mutein is produced starting from the nucleic acid encoding the mutein by means of genetic engineering methods in a bacterial or eukaryotic host organism and is isolated from this host organism or its culture.

15. A method for detecting a given target, comprising contacting a mutein selected from the group consisting of hNGAL, A2m, and 24p3 as defined in claim 6 with a sample suspected of containing the given target under suitable conditions, thereby allowing formation of a complex between the mutein and the given target, and determining the complexed mutein by a suitable signal.

16. The method of claim 15, wherein the given target is a protein, a protein domain, a peptide, a nucleic acid molecule, an organic molecule, or a metal complex, and the detection is effective to validate the given target as pharmacological drug target.

* * * * *